(12) United States Patent
Wyrick et al.

(10) Patent No.: US 7,575,869 B2
(45) Date of Patent: *Aug. 18, 2009

(54) GENOME WIDE LOCATION AND FUNCTION OF DNA BINDING PROTEINS

(75) Inventors: John Wyrick, Pasadena, CA (US); Richard A. Young, Weston, MA (US); Bing Ren, La Jolla, CA (US); Robert Francois, Boston, MA (US); Itamar Simon, Brighton, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 37 days.

This patent is subject to a terminal disclaimer.

(21) Appl. No.: 11/897,841

(22) Filed: Aug. 31, 2007

(65) Prior Publication Data

US 2008/0125328 A1 May 29, 2008

Related U.S. Application Data

(63) Continuation of application No. 10/032,281, filed on Dec. 21, 2001, now Pat. No. 7,470,507, and a continuation-in-part of application No. 09/654,409, filed on Sep. 1, 2000, now Pat. No. 6,410,243.

(60) Provisional application No. 60/323,620, filed on Sep. 20, 2001, provisional application No. 60/257,455, filed on Dec. 21, 2000, provisional application No. 60/151,972, filed on Sep. 1, 1999.

(51) Int. Cl.
*C12Q 1/68* (2006.01)
*C12P 19/34* (2006.01)

(52) U.S. Cl. .......................... 435/6; 435/91.2

(58) Field of Classification Search .................... 435/6, 435/91.2

See application file for complete search history.

(56) References Cited

U.S. PATENT DOCUMENTS

| 5,424,188 | A | 6/1995 | Schneider et al. |
| 6,046,165 | A | 4/2000 | Laughon et al. |
| 6,066,452 | A | 5/2000 | Weissman et al. |
| 6,109,776 | A | 8/2000 | Haas |
| 6,410,233 | B2 | 6/2002 | Mercola et al. |
| 6,410,243 | B1 | 6/2002 | Wyrick et al. |
| 6,982,145 | B1 | 1/2006 | Mercola et al. |

FOREIGN PATENT DOCUMENTS

| WO | WO0116378 A2 | 3/2001 |
| WO | WO0214550 A2 | 2/2002 |
| WO | WO2004053106 A2 | 6/2004 |
| WO | WO2004087965 A2 | 10/2004 |
| WO | WO2004097577 A2 | 11/2004 |
| WO | WO2005054461 A2 | 6/2005 |

OTHER PUBLICATIONS

Aparicio et al., "Components and dynamics of DNA replication complexes in *S. cerevisiae*: redistribution of MCM proteins and Cdc45p during S phase," 1997, Cell, 91(3):59-69.

(Continued)

*Primary Examiner*—Kenneth R. Horlick
(74) *Attorney, Agent, or Firm*—James S. Keddie; Bozicevic, Field & Francis LLP

(57) ABSTRACT

The present invention relates to a method of identifying a region (one or more) of a genome of a cell to which a protein of interest binds. In the methods described herein, DNA binding protein of a cell is linked (e.g., covalently crosslinked) to genomic DNA of a cell. The genomic DNA to which the DNA binding protein is linked is removed and combined or contacted with DNA comprising a sequence complementary to genomic DNA of the cell under conditions in which hybridization between the identified genomic DNA and the sequence complementary to genomic DNA occurs. Region(s) of hybridization are region(s) of the genome of the cell to which the protein of binds. A method of identifying a set of genes where cell cycle regulator binding correlates with gene expression and of identifying genomic targets of cell cycle transcription activators in living cells is also encompassed.

11 Claims, 24 Drawing Sheets

OTHER PUBLICATIONS

Barany, "The ligase chain reaction in a PCR world," 1991, PCR Methods Appl., 1(1):5-16.

Barany, "The Ligase Chain Reaction In A PCR World," Department Of Microbiology, Heart Microbiology Research Center, Cornell University Medical College, New York, NY 10021, pp. 1-12, (1992).

Bar-Joseph et al., "Computational discovery of gene modules and regulatory networks", Nat. Biotechnol., 2003, 21(11):1337-1342.

Bigler et al., "Isolation of a thyroid hormone-responsive gene by immunoprecipitation of thyroid hormone receptor-DNA complexes," 1994, Mol. Cell Biol., 14(11):7621-7632

Bigler et al., "Novel location and function of a thyroid hormone response element," 1995, EMBO J., 14(22):5710-5723.

Blat et al., "Cohesins bind to preferential sites along yeast chromosome III, with differential regulation along arms versus the centric region," 1999, Cell, 98(2):249-259.

Chee et al., "Accessing Genetic Information with High-Density DNA Arrays," Science, 1996, 274(5287):610-614.

Cohen-Kaminsky et al., "Chromatin immunoselection defines a TAL-1 target gene," 1998, EMBO J., 17(17):5151-5160.

De Risi et al., "Exploring the metabolic and genetic control of gene expression on a genomic scale," 1997, Science, 278(5338):680-686.

Deveaux et al., "p45 NF-E2 regulates expression of thromboxane synthase in megakaryocytes," 1997, EMBO J, 16(18):5654-5661.

Gould et al., "Connectin, a target of homeotic gene control in *Drosophila*," 1992, Development, 116(4):1163-1174.

Gould et al., "Targets of homeotic gene control in *Drosophila*" 1990, Nature, 348(6299):308-312.

Graba et al., "*Drosophila* Hox complex downstream targets and the function of homeotic genes," 1997, BioEssays, 19(5):379-388.

Graba et al., "DWnt-4, a novel *Drosophila* Wnt gene acts downsteam of homeotic complex genes in the visceral mesoderm," 1995, Development, 121(1):209-218.

Graba et al., "Homeotic control in *Drosophila*; the scabrous gene is an in vivo target of Ultrabithorax proteins," 1992, EMBO J., 11(9):3375-3384.

Grandori et al., "Myc-Max heterodimers activate a Dead box gene and interact with multiple E box-related sites in vivo," 1996, EMBO J., 15(16):4344-4357.

Hacia et al., "Two color hydridization analysis using high density oligonucleotide arrays and energy transfer dyes," Nucleic Acids Res., 1998, 26(16):3865-3866.

Hallahan et al., "C-jun and Egr-1 participate in DNA synthesis and cell survival in response to ionizing radiation exposure," 1995, J. Biol. Chem. 270(51):30303-30309.

Hartemink et al., "Combining location and expression data for principled discover of genetic regulatory network models," 2002, Pac Symp. Biocomput., 437-449.

Hecht et al., "Spreading of transcriptional repressor SIR3 from telomeric heterochromatin," 1996, Nature, 383(6595):92-96.

Holstege et al., "Dissecting the regulatory circuitry of a eukaryotic genome," 1998, Cell, 95(5):717-728.

Kohwi-Shigematsu et al., "Identification of base-unpairing region-binding proteins and characterization of their in vivo binding sequences," 1998, Methods Cell Biol., 53:323-354.

Landes Bioscience, "Transcription of Cell Cycle Genes," http://www.ncbi.nlm.nih.gov/books/bv.fcgi?rid=eurekah.section.11998, (1990).

Lee et al., "Transcriptional regulatory networks in *Saccharomyces cerevisiae*," 2002, Science, 298(5594):799-804.

Lipshutz et al., "High Density Synthetic Oligonucleotide Arrays," Nat. Genet., 1999, 21(1 Suppl):20-24.

Mukherjee et al., "Rapid analysis of the DNA-binding specificities of transcription factors with DNA microarrays ," 2004, Nat. Genet., 36(12):1331-1339.

Nickerson et al., "The nuclear matrix revealed by eluting chromatin from a cross-linked nucleus," 1997, Proc. Natl. Acad. Sci. USA, 94(9):4446-4450.

Odom et al., "Control of pancreas and liver gene expression by HNF transcription factors," 2004, Science, 303(5662):1378-1381.

Orlando et al., "Analysis of chromatin structure by in vivo formaldehyde cross-linking," 1997, Methods, 11(2):205-214.

Orlando et al., "Mapping Polycomb-repressed domains in the bithorax complex using in vivo formaldehyde cross-linked chromatin," 1993, Cell, 75(6):1187-1198.

Orlando, "Mapping chromosomal proteins in vivo by formaldehyde-crosslinked-chromatin immunoprecipitation," 2000, Trends Biochem. Sci., 25(3):99-104.

Pradel et al., "From selectors to realizator," 1998, Int. J. Dev. Biol. 42(3):417-421.

Reid et al., "Coordinate regulation of yeast ribosomal protein genes is associated with targeted recruitment of Esa1 histone acetylase," 2000, Mol. Cell, 6(6):1297-1307.

Ren et al., "Genome-wide location and function of DNA binding proteins," 2000, Science, 290(5500):2306-2309.

Roberts et al., "Signaling and Circuitry of Multiple MAPK Pathways Revealed by a Matrix of Global Gene Expression Profiles," Science, 2000, 287(5454):873-880.

Schena et al., "Microarrays: biotechnology's discovery platform for functional genomics," 1998, Trends Biotechnol., 16(7):301-306.

Schouten, "Hybridization selection of covalent nucleic acid-protein complexes. 2. Cross-linking of proteins to specific *Escherichia coli* mRNAs and DNA sequences by formaldehyde treatment of intact cells," 1985, J. Biol. Chem., 260(17):9929-9935.

Secko, "Messages from intergenic space," The Scientist, 2004, http://www.the-scientist.com/news/20040603/01.

Solomon et al., "Formaldehyde-mediated DNA-protein crosslinking: a probe for in vivo chromatin structures," 1985, Proc. Natl. Acad. Sci. USA, 82(19):6470-6474.

Solomon et al., "Mapping protein-DNA interactions in vivo with formaldehyde: evidence that histone H4 is retained on a highly transcribed gene," 1988, Cell, 53(6):937-947.

Strutt et al., "Co-localization of Polycomb protein and GAGA factor on regulatory elements responsible for the maintenance of homeotic gene expression," EMBO J., 1997, 16(12):3621-3631.

Takahashi et al., "Application of the chromatin immunoprecipitation method to identify in vivo protein-DNA associations in fission yeast," 2000, Sci. STKE, 2000(56): PL1.

Tanabe et al., "Evaluation of a whole-genome amplification method based on adaptor-ligation PCR of randomly sheared genomic DNA," Genes, Chromosomes Cancer, 2003, 38(2):168-176.

Tanaka et al., "Loading of an Mcm protein onto DNA replication origins is regulated by Cdc6p and CDKs," 1997, Cell, 90(4):649-660.

Tomotsune et al., "A mouse homologue of the *Drosophila* tumour-suppressor gene I(2)gI controlled by Hox-C8 in vivo," 1993, Nature, 365(6441):69-72.

Walter et al., "Measurement of in vivo DNA binding by sequence-specific transcription factors using UV cross-linking," 1997, Methods, 11(2):215-224.

Weinmann et al., "Isolating human transcription factor targets by coupling chromatin immunoprecipitation and CpG island microarray analysis," 2002, Genes Dev., 16(2):235-244.

Wyrick et al., "Deciphering gene expression regulatory networks," 2002, Curr. Opin. Genet. Dev., 12(2):130-136.

Yoshioka et al., "Quantitative analysis of the usage of human T cell receptor alpha and beta chain variable regions by reverse dot blot hybridization ," J Immunol. Methods, 1997, 201(2):145-155.

Interests:
RNA Polymerase II
SRB/Mediator Complex
General Transcription Factors
SWI/SNF Complex
SAGA
ORC complex
DNA Polymerase

| | Binding | | | | Expression | |
|---|---|---|---|---|---|---|
| Name | Glucose | | Galactose | | Ratio | Description |
| | Ratio | p-value | Ratio | p-value | Gal/Glu | |
| GAL2 | 2.0 | 2.5X10-02 | 9.5 | 1.5X10-10 | 168.6 | Galactose permease |
| GAL3 | 1.4 | 5.4X10-01 | 6.6 | 3.3X10-10 | 16.2 | Regulatory protein required for rapid induction of galactose pathway |
| GAL7 | 0.4 | 2.0X10+00 | 8.2 | 6.4X10-10 | 170.1 | UDP-glucose–hexose-1-phosphate uridylyltransferase |
| GAL1 | 1.3 | 6.0X10-01 | 7.8 | 1.5X10-09 | 271.3 | Galactokinase, first step in galactose metabolism |
| GAL10 | 1.3 | 6.0X10-01 | 7.8 | 1.5X10-09 | 110.8 | UDP-glucose 4-epimerase |
| FUR4 | 0.9 | 2.0X10+00 | 4.6 | 4.3X10-08 | 4.6 | Uracil permease (adjacent to GAL1) |
| GCY1 | 0.9 | 1.2X10+00 | 4.3 | 1.3X10-07 | 93.1 | Galactose-induced oxidoreductase |
| MTH1 | 0.9 | 1.2X10+00 | 4.0 | 2.4X10-07 | 21.6 | Repressor of hexose transport genes |
| GAL80 | 0.5 | 1.3X10+00 | 3.7 | 7.0X10-07 | 4.0 | Negative regulator for expression of galactose-induced genes |
| PCL10 | 0.6 | 1.8X10+00 | 3.0 | 6.8X10-06 | 2.6 | Cyclin that associates with Pho85p, involved in glycogen accumulation |
| YBR012W | 3.7 | 1.7X10-07 | 10.4 | 1.2X10-10 | 1.5 | Unknown function (adjacent to GAL1) |
| YDR042C | 1.4 | 5.5X10-01 | 8.2 | 3.5X10-10 | 1.5 | Unknown function (share intergenic region with GAL3) |
| GSY1 | 2.7 | 2.9X10-02 | 6.0 | 4.8X10-10 | 1.0 | Suppressor of the Gal(-) phenotype of snf1 mep1 snf4/10/11 cells |
| TLC1 | 0.6 | 1.9X10+00 | 4.2 | 1.2X10-07 | 1.0 | RNA subunit of telomerase |
| PDX3 | 0.6 | 1.9X10+00 | 4.2 | 1.7X10-07 | 1.6 | Pyridoxine phosphate oxidase |
| RK11 | 0.9 | 1.2X10+00 | 4.3 | 1.3X10-07 | 1.4 | Unknown function (share intergenic region with GCY1) |
| YMR044 | 2.3 | 6.0X10-02 | 4.0 | 3.4X10-07 | 1.7 | Unknown function |
| SRO2 | 0.8 | 1.1X10+00 | 3.5 | 1.1X10-06 | 0.6 | Drug efflux pump involved in resistance to multiple drugs (adjacent to GAL3) |
| YDR010C | 0.9 | 1.1X10+00 | 3.5 | 1.1X10-06 | 1.0 | Unknown function (adjacent to GAL3) |
| APC9 | 1.9 | 1.9X10-01 | 3.6 | 2.0X10-06 | 1.2 | Component of the anaphase-promoting complex (APC) |
| CSG2 | 0.3 | 1.9X10+00 | 3.3 | 2.4X10-06 | 1.3 | Required for synthesis of the mannosylated sphingolipids |
| RPL4B | 0.9 | 1.3X10+00 | 3.3 | 2.6X10-06 | 0.8 | Ribosomal protein L4, 60s (adjacent to PCL10) |
| YGL132W | 0.6 | 1.8X10+00 | 3.0 | 9.1X10-06 | 1.0 | Unknown function (adjacent to PCL10) |
| CHA4 | 1.5 | 4.1X10-01 | 3.1 | 9.6X10-06 | 1.0 | Zinc-finger protein required for transcriptional activation of CHA1 |

FIGURE 6A

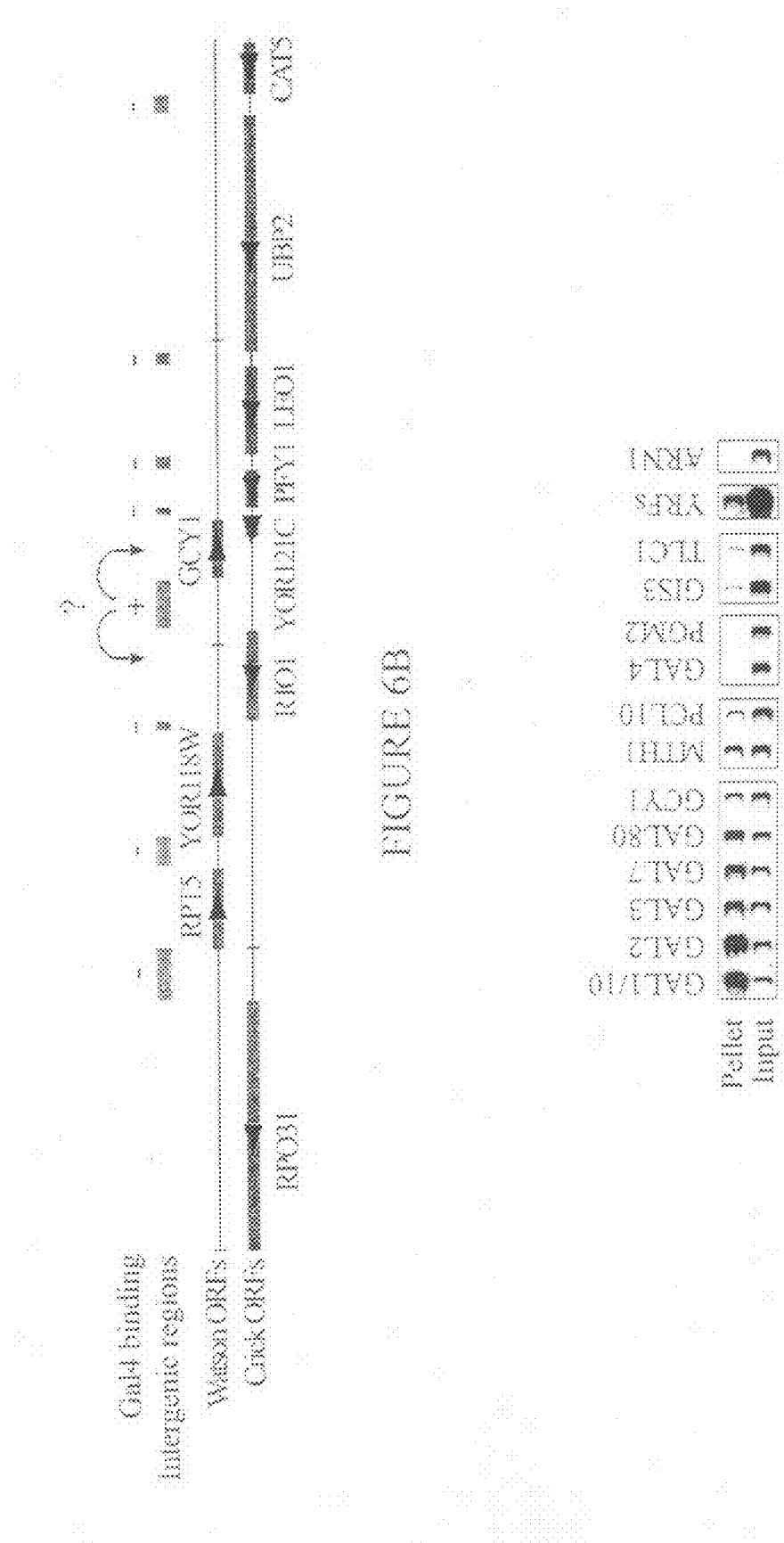

| Name | Binding before ratio | Binding before p-value | Binding after ratio | Binding after p-value | Description |
|---|---|---|---|---|---|
| PRM1 | 2.7 | 1.3E-04 | 6.2 | 4.5E-05 | Pheromone-regulated membrane protein |
| ERG24 | 2.7 | 1.3E-04 | 6.2 | 4.5E-05 | C-14 sterol reductase |
| FCL2 | 3.3 | 4.2E-05 | 6.0 | 5.8E-05 | Cyclin partly in association with Pho85p |
| FR2 | 2.6 | 2.2E-04 | 5.6 | 9.5E-05 | Protein involved in mating induction |
| STE12 | 4.1 | 1.4E-06 | 4.1 | 3.1E-04 | Transcription factor required for mating |
| FUS1 | 5.0 | 2.8E-07 | 4.1 | 5.6E-04 | Protein required for cell fusion during mating |
| CDC48 | 2.9 | 1.9E-04 | 4.6 | 1.0E-03 | Required for cell division and homotypic membrane fusion |
| YCR072C | 2.4 | 5.8E-04 | 3.2 | 1.5E-03 | Protein involved in growth regulation |
| FUS3 | 3.3 | 3.9E-05 | 5.4 | 2.0E-03 | MAPK mediating mating pheromone signaling |
| PEP1 | 3.3 | 3.9E-05 | 5.4 | 2.0E-03 | Receptor for vacuolar sorting of soluble vacuolar proteins |
| MET2 | 2.1 | 4.8E-03 | 2.8 | 3.2E-03 | Homoserine O-acetyltransferase |
| YOR123C | 0.7 | 1.0E+00 | 5.2 | 1.0E-04 | Protein of unknown function |
| UTH1 | 1.7 | 2.9E-02 | 5.2 | 1.0E-04 | Protein involved in the aging process |
| AFR1 | 1.9 | 8.6E-01 | 5.1 | 1.0E-04 | Protein involved in morphogenesis of the mating projection |
| GIC2 | 1.4 | 1.1E-01 | 5.0 | 1.2E-04 | Putative effector of Cdc42p, important for bud emergence |
| YNR046W | 1.9 | 7.6E-03 | 4.0 | 1.4E-04 | Protein of unknown function |
| MSS11 | 1.0 | 8.1E-01 | 4.9 | 1.8E-04 | Protein involved in regulation of starch metabolism |
| YOR343C | 1.1 | 7.0E-01 | 3.9 | 4.1E-04 | Protein of unknown function |
| CHS1 | 0.9 | 1.0E+00 | 4.1 | 4.2E-04 | Chitin synthase I, functions during cell separation |
| SCH9 | 1.3 | 2.1E-01 | 4.2 | 4.5E-04 | Serine/threonine protein kinase that is activated by cAMP |

FIGURE 7A

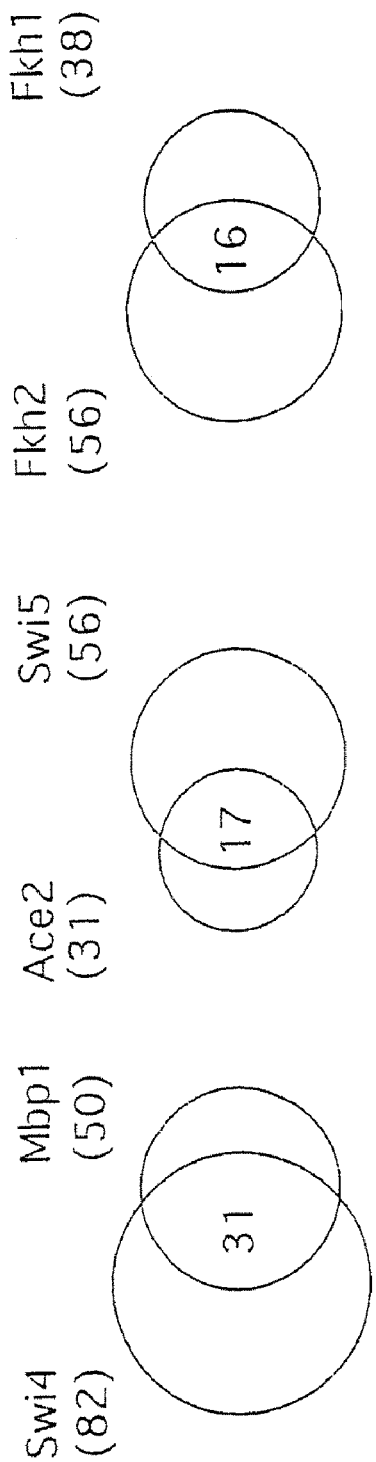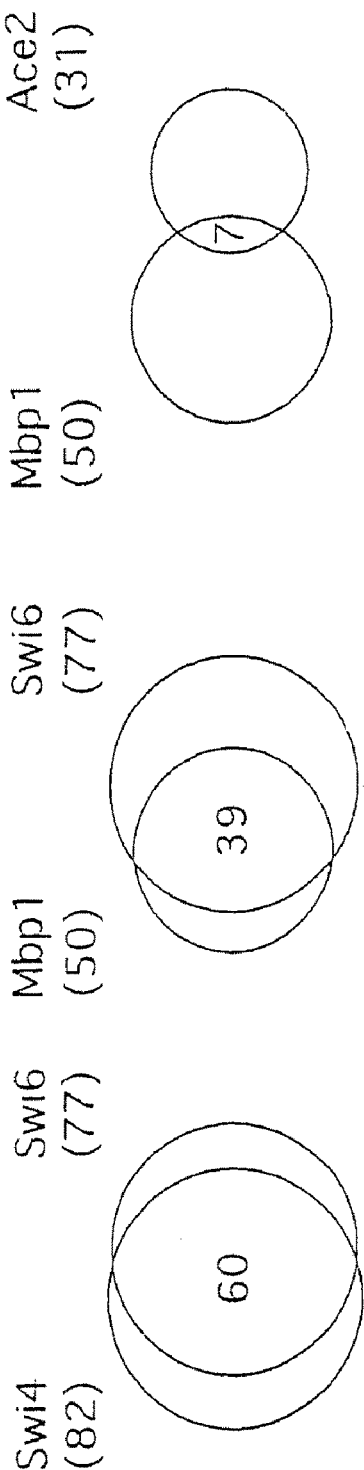
Figure 14A
Figure 14B
Figure 14C

SEQUENCE LISTING

```
<160> NUMBER OF SEQ ID NOS: 32

<210> SEQ ID NO 1
<211> LENGTH: 12
<212> TYPE: DNA
<213> ORGANISM: Artificial Sequence
<220> FEATURE:
<223> OTHER INFORMATION: Mbp 1 consensus binding motifs
<220> FEATURE:
<221> NAME/KEY: misc_feature
<222> LOCATION: 2, 4, 12
<223> OTHER INFORMATION: n = A,T,C or G

<400> SEQUENCE: 1
wnrnrwcgcg hn                                                           12

<210> SEQ ID NO 2
<211> LENGTH: 12
<212> TYPE: DNA
<213> ORGANISM: Artificial Sequence
<220> FEATURE:
<223> OTHER INFORMATION: Swi4 consensus binding motifs
<220> FEATURE:
<221> NAME/KEY: misc_feature
<222> LOCATION: 1, 2, 3, 4
<223> OTHER INFORMATION: n = A,T,C or G

<400> SEQUENCE: 2
nnnncrcsaa aw                                                           12

<210> SEQ ID NO 3
<211> LENGTH: 24
<212> TYPE: DNA
<213> ORGANISM: Artificial Sequence
<220> FEATURE:
<223> OTHER INFORMATION: Mcm1/Fkh2 consensus binding motifs
<220> FEATURE:
<221> NAME/KEY: misc_feature
<222> LOCATION: 1, 2, 3, 4, 7, 8, 9, 10, 11, 12, 15, 20
<223> OTHER INFORMATION: n = A,T,C or G

<400> SEQUENCE: 3
nnnnyynnnn nngsnaawwn ryma                                              24

<210> SEQ ID NO 4
<211> LENGTH: 16
<212> TYPE: DNA
<213> ORGANISM: Artificial Sequence
<220> FEATURE:
<223> OTHER INFORMATION: Mcm1 consensus binding motifs
<220> FEATURE:
<221> NAME/KEY: misc_feature
<222> LOCATION: 7, 11
<223> OTHER INFORMATION: n = A,T,C or G
```

```
<400> SEQUENCE: 4
wwtwccnraw nrrgwa                                                    16

<210> SEQ ID NO 5
<211> LENGTH: 9
<212> TYPE: DNA
<213> ORGANISM: Artificial Sequence
<220> FEATURE:
<223> OTHER INFORMATION: Ace2 consensus binding motifs
<220> FEATURE:
<221> NAME/KEY: misc_feature
<222> LOCATION: (1)...(9)
<223> OTHER INFORMATION: n = A,T,C or G

<400> SEQUENCE: 5 rancmmgca                                                             9

<210> SEQ ID NO 6
<211> LENGTH: 16
<212> TYPE: DNA
<213> ORGANISM: Artificial Sequence
<220> FEATURE:
<223> OTHER INFORMATION: Ace2 consensus binding motifs
<220> FEATURE:
<221> NAME/KEY: misc_feature
<222> LOCATION: 6, 7, 8, 11, 14, 16
<223> OTHER INFORMATION: n = A,T,C or G

<400> SEQUENCE: 6
agggannnwk nwrnkn                                                    16

<210> SEQ ID NO 7
<211> LENGTH: 14
<212> TYPE: DNA
<213> ORGANISM: Artificial Sequence
<220> FEATURE:
<223> OTHER INFORMATION: Swi5 consensus binding motifs
<220> FEATURE:
<221> NAME/KEY: misc_feature
<222> LOCATION: 2, 3, 4, 7, 8
<223> OTHER INFORMATION: n = A,T,C or G

<400> SEQUENCE: 7
gnnnggnnsc agma                                                      14

<210> SEQ ID NO 8
<211> LENGTH: 13
<212> TYPE: DNA
<213> ORGANISM: Artificial Sequence
<220> FEATURE:
<223> OTHER INFORMATION: Swi5 consensus binding motifs
<220> FEATURE:
<221> NAME/KEY: misc_feature
<222> LOCATION: 2, 3, 8, 12
<223> OTHER INFORMATION: n = A,T,C or G

<400> SEQUENCE: 8
gnnatgrntg gnk                                                       13

<210> SEQ ID NO 9
<211> LENGTH: 8
<212> TYPE: DNA
<213> ORGANISM: Artificial Sequence
<220> FEATURE:
<223> OTHER INFORMATION: Fkh1/Fkh2 consensus binding motifs

<400> SEQUENCE: 9 rtaaacaa                                                              8
```

<210> SEQ ID NO 10
<211> LENGTH: 19
<212> TYPE: DNA
<213> ORGANISM: Artificial Sequence
<220> FEATURE:
<223> OTHER INFORMATION: Fkh1 consensus binding motifs
<220> FEATURE:
<221> NAME/KEY: misc_feature
<222> LOCATION: 2, 5, 8, 9, 10, 12, 13, 14
<223> OTHER INFORMATION: n = A,T,C or G

<400> SEQUENCE: 10
rngsngsnnn gnnnssssy                                           19

<210> SEQ ID NO 11
<211> LENGTH: 12
<212> TYPE: DNA
<213> ORGANISM: Artificial Sequence
<220> FEATURE:
<223> OTHER INFORMATION: Fkh1 consensus binding motifs
<220> FEATURE:
<221> NAME/KEY: misc_feature
<222> LOCATION: 5, 11
<223> OTHER INFORMATION: n = A,T,C or G

<400> SEQUENCE: 11
ttykngagaa nt                                                  12

<210> SEQ ID NO 12
<211> LENGTH: 13
<212> TYPE: DNA
<213> ORGANISM: Artificial Sequence
<220> FEATURE:
<223> OTHER INFORMATION: Fkh1 consensus binding motifs
<220> FEATURE:
<221> NAME/KEY: misc_feature
<222> LOCATION: 4
<223> OTHER INFORMATION: n = A,T,C or G

<400> SEQUENCE: 12
kkcnsrssmk ssk                                                 13

<210> SEQ ID NO 13
<211> LENGTH: 67
<212> TYPE: DNA
<213> ORGANISM: Artificial Sequence
<220> FEATURE:
<223> OTHER INFORMATION: Z1372 MBP1 18 myc forward primer

<400> SEQUENCE: 13
ataagggcgc agaacagatc atcacaatct caaacgcgaa tagtcatgca tccggttctg    60
ctgctag                                                            67

<210> SEQ ID NO 14
<211> LENGTH: 67
<212> TYPE: DNA
<213> ORGANISM: Artificial Sequence
<220> FEATURE:
<223> OTHER INFORMATION: Z1372MBP1 18 myc backward primer

<400> SEQUENCE: 14 ctattttca gtatatggat acatgtaaag ttcctctatt tatgtatatt cctcgaggcc    60
agaagac                                                            67

<210> SEQ ID NO 15

```
<211> LENGTH: 67
<212> TYPE: DNA
<213> ORGANISM: Artificial Sequence
<220> FEATURE:
<223> OTHER INFORMATION: Z1335 SWI4 18 myc forward primer

<400> SEQUENCE: 15
acattgactc aaaattggac gatatagaaa aggatttgag ggcaaacgca tccggttctg    60
ctgctag                                                              67

<210> SEQ ID NO 16
<211> LENGTH: 67
<212> TYPE: DNA
<213> ORGANISM: Artificial Sequence
<220> FEATURE:
<223> OTHER INFORMATION: Z1335 SWI4 18 myc backward primer

<400> SEQUENCE: 16
aaaaactctg ataatatagt aaaaattatt ggtacattgt gaattaaaat cctcgaggcc    60
agaagac                                                              67

<210> SEQ ID NO 17
<211> LENGTH: 67
<212> TYPE: DNA
<213> ORGANISM: Artificial Sequence
<220> FEATURE:
<223> OTHER INFORMATION: Z1373 SWI6 18 myc forward primer

<400> SEQUENCE: 17
aagacattga cactgacgaa atgcaagatt ttttaaaaaa gcatgcttca tccggttctg    60
ctgctag                                                              67

<210> SEQ ID NO 18
<211> LENGTH: 67
<212> TYPE: DNA
<213> ORGANISM: Artificial Sequence
<220> FEATURE:
<223> OTHER INFORMATION: Z1373 SWI16 18 myc backward primer

<400> SEQUENCE: 18
aataacttca aataaagtca taaaagttaa tgcaatgaaa tcacatgccc cctcgaggcc    60
agaagac                                                              67

<210> SEQ ID NO 19
<211> LENGTH: 67
<212> TYPE: DNA
<213> ORGANISM: Artificial Sequence
<220> FEATURE:
<223> OTHER INFORMATION: Z1448 FKH1 9 myc forward primer

<400> SEQUENCE: 19
catccatgga cgtaacaaca aacgcaaacg tgaacaattc ctctctgagt tccggttctg    60
ctgctag                                                              67

<210> SEQ ID NO 20
<211> LENGTH: 67
<212> TYPE: DNA
<213> ORGANISM: Artificial Sequence
<220> FEATURE:
<223> OTHER INFORMATION: Z1448 FKH1 9 myc backward primer

<400> SEQUENCE: 20
ctttgttctt tattgtttaa taatacatat gggttcgacg acgctgaatt cctcgaggcc    60
``` agaagac 67

<210> SEQ ID NO 21
<211> LENGTH: 67
<212> TYPE: DNA
<213> ORGANISM: Artificial Sequence
<220> FEATURE:
<223> OTHER INFORMATION: Z1370 FKH2 18 myc forward primer

<400> SEQUENCE: 21
aggaactaat actagatacg gatggtgcaa agatcagtat tatcaacaac tccggttctg   60
ctgctag   67

<210> SEQ ID NO 22
<211> LENGTH: 67
<212> TYPE: DNA
<213> ORGANISM: Artificial Sequence
<220> FEATURE:
<223> OTHER INFORMATION: Z1370 FKH2 18 myc backward primer

<400> SEQUENCE: 22
ccatttctca ttcatttctt tagtcttagt gattcacctt gtttcttgtc cctcgaggcc   60
agaagac   67

<210> SEQ ID NO 23
<211> LENGTH: 67
<212> TYPE: DNA
<213> ORGANISM: Artificial Sequence
<220> FEATURE:
<223> OTHER INFORMATION: Z1369 NDD1 18 myc forward primer

<400> SEQUENCE: 23
caaggaaaag ctgtaattct aaatctaatg gaaatttatt caattcacag tccggttctg   60
ctgctag   67

<210> SEQ ID NO 24
<211> LENGTH: 67
<212> TYPE: DNA
<213> ORGANISM: Artificial Sequence
<220> FEATURE:
<223> OTHER INFORMATION: Z1369 NDD1 18 myc backward primer

<400> SEQUENCE: 24
gcttgaaatt tcgattaaaa aaaaaaggtg agatgcaagt ttggttaata cctcgaggcc   60
agaagac   67

<210> SEQ ID NO 25
<211> LENGTH: 67
<212> TYPE: DNA
<213> ORGANISM: Artificial Sequence
<220> FEATURE:
<223> OTHER INFORMATION: Z1321 MCM1 18 myc forward primer

<400> SEQUENCE: 25
agaatgctgc ctaccaacaa tactttcaag aaccgcaaca aggccaatac tccggttctg   60
ctgctag   67

<210> SEQ ID NO 26
<211> LENGTH: 67
<212> TYPE: DNA
<213> ORGANISM: Artificial Sequence
<220> FEATURE:

<223> OTHER INFORMATION: Z1321 MCM1 18 myc backward primer

<400> SEQUENCE: 26 cttttcctc ttaatgctcg tctatgaatt atatacggaa atcgataaga cctcgaggcc    60
agaagac    67

<210> SEQ ID NO 27
<211> LENGTH: 67
<212> TYPE: DNA
<213> ORGANISM: Artificial Sequence
<220> FEATURE:
<223> OTHER INFORMATION: Z1371 ACE2 18 myc forward primer

<400> SEQUENCE: 27
cgcacgagca aaactcgaac cgcacccttt caaacgaaac tgatgctctc tccggttctg    60
ctgctag    67

<210> SEQ ID NO 28
<211> LENGTH: 67
<212> TYPE: DNA
<213> ORGANISM: Artificial Sequence
<220> FEATURE:
<223> OTHER INFORMATION: Z1371 ACE2 18 myc backward primer

<400> SEQUENCE: 28
tattgttact attatttatt atgttaatat catgcataga taaatgttcg cctcgaggcc    60
agaagac    67

<210> SEQ ID NO 29
<211> LENGTH: 25
<212> TYPE: DNA
<213> ORGANISM: Artificial Sequence
<220> FEATURE:
<223> OTHER INFORMATION: oJW102 primer

<400> SEQUENCE: 29
gcggtgaccc gggagatctg aattc    25

<210> SEQ ID NO 30
<211> LENGTH: 11
<212> TYPE: DNA
<213> ORGANISM: Artificial Sequence
<220> FEATURE:
<223> OTHER INFORMATION: oJW103 primer

<400> SEQUENCE: 30
gaattcagat c    11

<210> SEQ ID NO 31
<211> LENGTH: 8
<212> TYPE: DNA
<213> ORGANISM: Artificial Sequence
<220> FEATURE:
<223> OTHER INFORMATION: Forkhead binding motif

<400> SEQUENCE: 31 gtaaacaa    8

<210> SEQ ID NO 32
<211> LENGTH: 17
<212> TYPE: DNA
<213> ORGANISM: Artificial Sequence
<220> FEATURE:
<223> OTHER INFORMATION: Gal 4 activator consensus binding motif

```
<220> FEATURE:
<221> NAME/KEY: misc_feature
<222> LOCATION: 4, 5, 6, 7, 8, 10, 12, 13, 14
<223> OTHER INFORMATION: n = A,T,C or G

<400> SEQUENCE: 32
cggnnnnntn bnnnccg                                                    17
```

GENOME WIDE LOCATION AND FUNCTION OF DNA BINDING PROTEINS

RELATED APPLICATION(S)

This application is a continuation of U.S. application Ser. No. 10/032,281, filed Dec. 21, 2001, U.S. Pat. No. 7,470,507, which claims the benefit of U.S. Provisional Application Nos. 60/323,620, filed on Sep. 20, 2001, and 60/257,455, filed on Dec. 21, 2000. Application Ser. No. 10/032,281 is a continuation-in-part of U.S. application Ser. No. 09/654,409, filed Sep. 1, 2000, U.S. Pat. No. 6,410,243, which claims the benefit of U.S. Provisional Application No. 60/151,972, filed on Sep. 1, 1999.

The entire teachings of the above application(s) are incorporated herein by reference.

GOVERNMENT SUPPORT

The invention was supported, in whole or in part, by a grant GM34365 from the National Institutes of Health. The Government has certain rights in the invention.

BACKGROUND OF THE INVENTION

Many proteins involved in regulating genome expression, chromosomal replication and cellular proliferation function trough their ability to bind specific sites in the genome. Transcriptional activators, for example, bind to specific promoter sequences and recruit chromatin modifying complexes and the transcription apparatus to initiate RNA synthesis. The remodeling of gene expression that occurs as cells move through the cell cycle, or when cells sense changes in their environment, is effected in part by changes in the DNA-binding status of transcriptional activators. Distinct DNA-binding proteins are also associated with centromeres, telomeres, and origins of DNA replication, where they regulate chromosome replication and maintenance. Although considerable knowledge of many fundamental aspects of gene expression and DNA replication has been obtained from studies of DNA-binding proteins, an understanding of these proteins and their functions is limited by our knowledge of their binding sites in the genome.

In addition, regulation of the cell cycle clock is effected through a controlled pro gram of gene expression and oscillations in the activity of the cyclin-dependent (CDK) family of protein kinases. Much is known about the control of stage-specific functions by CDKs and their regulators during the cell cycle (Mendenhall and Hodge, 1998; Morgan, 1997; Nurse, 2000). A more complete understanding of cell cycle regulation is constrained, however, by our limited knowledge of the transcriptional regulatory network that controls the clock. Additional knowledge of cell cycle regulation would make it clearer how the transcriptional and post-transcriptional regulatory networks that control the complex and highly regulated processes are involved in the cell cycle and make it possible to produce a genetic/regulatory network map and to not only identify steps in the pathway, but also connect the cell cycle with other cellular functions.

Proteins which bind to a particular region of DNA can be detected using known methods. However, a need exists for a method which allows examination of the binding of proteins to DNA across the entire genome of an organism.

SUMMARY OF THE INVENTION

The present invention relates to a method of identifying a region (one or more) of a genome of a cell to which a protein of interest binds. In the methods described herein, DNA binding protein of a cell is linked (e.g., covalently crosslinked) to genomic DNA of a cell. The genomic DNA to which the DNA binding protein is linked is identified and combined or contacted with DNA comprising a sequence complementary to genomic DNA of the cell (e.g., all or a portion of a cell's genomic DNA such as one or more chromosome or chromosome region) under conditions in which hybridization between the identified genomic DNA and the sequence complementary to genomic DNA occurs. Region(s) of hybridization are region(s) of the genome of the cell to which the protein of interest binds. The methods of the present invention are preferably performed using living cells.

In one embodiment, proteins which bind DNA in a cell are crosslinked to the cellular DNA. The resulting mixture, which includes DNA bound by protein and DNA which is not bound by protein is subject to shearing conditions. As a result, DNA fragments of the genome crosslinked to DNA binding protein are generated and the DNA fragment (one or more) to which the protein of interest is bound is removed from the mixture. The resulting DNA fragment is then separated from the protein of interest and amplified, using sown methods. The DNA fragment is combined with DNA comprising a sequence complementary to genomic DNA of the cell, under conditions in which hybridization between the DNA fragment and a region of the sequence complementary to genomic DNA occurs; and the region of the sequence complementary to genomic DNA to which the DNA fragment hybridizes is identified. The identified region (one or more) is a region of the genome of the cell, such as a selected chromosome or chromosomes, to which the protein of interest binds.

In a particular embodiment, the present invention relates to a method of identifying a region of a genome (such as a region of a chromosome) of a cell (test sample) to which a protein of interest binds, wherein the DNA binding protein of the cell is crosslinked to genomic DNA of the cell using formaldehyde. DNA fragments of the crosslinked genome are generated and the DNA fragment to which the protein of interest is bound is removed or separated from the mixture, such as through immunoprecipitation using an antibody that specifically binds the protein of interest. This results in separation of the DNA-protein complex. The DNA fragment in the complex is separated from the protein of interest, for example, by subjecting the complex to conditions which reverse the crosslinks. The separated DNA fragment is amplified (e.g., non-specifically) using ligation-mediated polymerase chain reaction (LM-PCR), and then fluorescently labeled. The labeled DNA fragment is contacted with a DNA microarray comprising a sequence complementary to genomic DNA of the cell, under conditions in which hybridization between the DNA fragment and a region of the sequence complementary to genomic DNA occurs. The region of the sequence complementary to genomic DNA to which the DNA fragment hybridizes is identified by measuring fluorescence intensity, and the fluorescence intensity of the region of the sequence complementary to genomic DNA to which the DNA fragment hybridizes is compared to the fluorescence intensity of a control. Fluorescence intensity in a region of the sequence complementary to genomic DNA which is greater than the fluorescence intensity of the control in that region of the sequence complementary to genomic DNA marks the region of the genome in the cell to which the protein of interest binds.

Also encompassed by the present invention is a method of determining a function of a protein of interest which binds to the genomic DNA of a cell. In this method, DNA binding protein of the cell is crosslinked to the genomic DNA of the cell. DNA fragments of the genome crosslinked to DNA binding protein are then generated, as described above, and the DNA fragment (one or more) to which the protein of interest is bound is removed from the mixture. The resulting DNA fragment is then separated from the protein of interest and amplified. The DNA fragment is combined with DNA comprising a sequence complementary to genomic DNA of the cell, under conditions in which hybridization between the DNA fragment and a region of the sequence complementary to genomic DNA occurs; and the region of the sequence complementary to genomic DNA to which the DNA fragment hybridizes is identified. This identified region is a region of the genome of the cell to which the protein of interest binds. The identified region is characterized and the characteristic of the identified region indicates the function of the protein of interest (e.g., a regulatory protein such as a transcription factor; an oncoprotein).

The present invention also relates to a method of determining whether a protein of interest which binds to genomic DNA of a cell functions as a transcription factor. In one embodiment, DNA binding protein of the cell is crosslinked to the genomic DNA of the cell. DNA fragments of the crosslinked genome are generated and the DNA fragment to which the protein of interest is bound is removed from the mixture. The resulting DNA fragment is separated from the protein of interest and amplified. The DNA fragment is combined with DNA comprising a sequence complementary to genomic DNA of the cell, under conditions in which hybridization between the DNA fragment and a region of the sequence complementary to genomic DNA occurs. The region of the sequence complementary to genomic DNA to which the DNA fragments hybridizes is identified; wherein if the region of the genome is a regulatory region, then the protein of interest is a transcription factor.

The present invention also relates to a method of identifying a set of genes, the members of which are genes for which cell cycle regulator binding correlates with gene expression. The method comprises identifying a set of genes that is bound in vivo by at least one cell cycle regulator (e.g., transcriptional activator) in a selected cell type (e.g., mammalian cell, yeast cell); comparing the set of genes identified with genes whose expression levels vary in a periodic manner during the cell cycle of the selected cell type; and identifying genes that are bound by one or more of the cell cycle regulators, thus identifying a set of genes, the members of which are genes whose expression levels vary in a periodic manner during the cell cycle and are bound by at least one cell cycle regulator, wherein the set identified is referred to as a set of genes, the members of which are genes for which cell cycle regulator binding correlates with gene expression.

The methods described herein facilitate the dissection of the cells regulatory network of gene expression across the entire genome and aid in the identification of gene function. Work described herein provides the basis for constructing a complete map of the transcriptional regulatory network that controls the cell cycle. In one embodiment, it forms the foundation for a complete map of the transcriptional regulatory network that controls the yeast cell cycle.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 6A shows the set of 24 genes whose promoter regions are most likely to be bound by Gal4 by the analysis criteria described herein.

FIG. 6B is a schematic of the Gal4 binding intergenic regions.

FIG. 6C shows the results of conventional CHIP analysis.

FIG. 9A depicts the stages of the cell cycle together with yeast cell morphology (brown) and transcriptional regulators (blue); the transcriptional regulators are positioned at the stage during which they have been reported to function (Breedon et al., Curr. Biol., 10:R586-R588 (2000), Mendenhall et al., Mol. Biol. Reap., 62:1191-1243 (1998)).

FIG. 9B is a scatter plot of Cy5 versus Cy3 intensities for a control experiment in which aliquots of whole cell extract (WCE) were independently labeled with Cy3 and Cy5 and hybridized to a DNA microarray containing all yeast intergenic regions. The red and blue lines border the regions with confidence levels of p<0.001 and p<0.01, respectively.

FIG. 9C is a scatter plot of an experiments in which the Fkh2, IP-enriched DNA was labeled with Cy5 and the WCE was labeled with Cy3. The red and blue lines border the regions with confidence levels of p<0.001 and p<0.01, respectively. The cpols whose values have confidence levels of p<0.001 represent promoters most likely bound by the Fkh2 factor.

FIG. 10A show the 213 of the 800 cell cycle genes whose promoter regions were bound by a myc-tagged version of at least one of the nine cell cycle transcription factors (p<0.001) are represented as horizontal lines. The weight-averaged binding ratios are displayed using a blue and white color scheme (genes with p values<0.001 are displayed in blue). The expression ratios of an a factor synchronization time course from Spellman et al., *Mol. Cell. Biol. Cell,* 9:3.273-3297 (1998) are displayed using a red (induced) and green (repressed) color scheme.

FIG. 10B is a schematic in which the circle represents a smoothed distribution of the transcription timing (phase) of the 800 cell cycle genes (Spellman et al., *Mol. Cell Biol. Cell,* 9:3273-3297 (1998)). The intensity of the red color, normalized by the maximum intensity value for each factor, represents the fraction of genes expressed at that point that are bound by a specific activator. The similarity in the distribution of color for specific factors (with Swi4, Swi6, and Mbp1, for example) shows that these factors bind to genes that are expressed during the same time frame.

FIG. 11A shows a summary of previous evidence for regulation of cell cycle transcription factor genes and CLN3 transcriptional regulators (Althoefer et al., *Mol. Cell Biol.,* 15:5917-5928 (1998); Foster et al. *Mol. Cell Biol.,* 13:3792-3801 (1993); Koranda et al., *Nature,* 406:94-98 (2000); Kumar et al. *Curr. Biol.,* 10:896-906 (2000); Kuo et al., *Mol. Cell Biol.,* 14:3348-359 (1994); Loy et al. *Mol. Cell Biol.,* 19:3312-3327 (1999); Mackay et al. *Mol. Cell Biol.,* 21.4140-4148 (2001); McInerny et al. *Genes Dev.,* 11:1277-1288 (1997); Pic et al. *Embo J.,* 19:3750-3761 (2000); Zhu et al. *Nature,* 406:90-94 (2000)). The relationships between the transcription factors and their target genes are indicated by red arrows; solid lines represent evidence for direct regulation by these factors; and dashed lines represent inferences from indirect evidence. The blue arrows represent posttranscriptional regulation by Cln3/Cdc28 (Dirick et al. *Embo. J,* 14:4803-4813 (1995)).

FIG. 11B is a model for the closed regulatory circuit produced by cell cycle transcriptional regulators based on genome-wide binding data. The genome-wide location data indicate that each group of transcriptional activators regulates activators acting in the next cell cycle stage. The red arrows represent binding of a transcription factor to the promoter of another regulatory factor. The blue arrows represent post-translational regulation.

FIG. 12A shows a summary of previous evidence for transcriptional regulation of genes encoding the cyclins (green) and cyclin/CDK regulators (red) by the cell cycle transcription factors (Althoefer et al. *Mol. Cell Biol.,* 15:5917-5928 (1998); Dirick et al. *Nature,* 357:508-513 (1992); Hollenhorst et al. *Genetics,* 154:1533-1548 (2000'; Iyer et al. *Nature,* 409:533-536 (2001); Knapp et al. *Mol. Cell Biol.,* 16:5701-5707 (1998); Koch et al. *Science,* 261:1551-1557 (1993); Koranda et al. *Science,* 261:1551-1557 (1993); Kumar et al. *Curr. Biol.,* 10:896-906 (2000); Kuo et al., *Mol. Cell. Biol.,* 14:3348-359 (1994); Loy et al. *Mol. Cell Biol.,* 19:3312-3327 (1999); Mackay et al. *Mol. Cell Biol.,* 21:4140-4148 (2001); McBride et al. *J. Biol. Chem.,* 274:21029-21036 (1999); McInerny et al. *Genes Dev.,* 11:1277-1288 (1997); Nasmyth et al. *Genes Dev.,* 11:1277-1288 (1997); Oehlen et al. *Mol. Cell Biol.,* 16:2830-2837 (1996); Ogas et al. *Cell,* 66:1015-1025 (1991); Partridge et al. *J. Biol. Chem.,* 272:9071-9077 (1997); Pic et al. *Embo J.,* 19:3750-3761 (2000); Schwab et al. *Genes Dev.,* 7: 1160-1175 (1993); Toyn et al. *Genetics,* 145:85-96 (1997); Zhu et al. *Nature,* 406.90-94 (2000)). The factors, as well as their targets, are positioned according to their approximate time of function. The relationships between the transcription factors and their target genes are indicated by arrows, solid lines represent evidence for direct regulation by these factors, and dashed lines represent inferences from indirect evidence.

FIG. 12B is a model for transcriptional regulation of cyclin and cyclin/CDK regulators based on previous studies and on genome-wide binding data. Each group of transcription factors regulates key cell cycle regulators that are needed for progression through the cell cycle.

FIGS. 14A-14C are diagrams showing partial redundancy between homologous activators.

FIG. 14A are Venn diagrams depicting the overlap between the targets of pairs of homologous cell cycle transcriptional regulatory proteins. The numbers in parenthesis under each activator represent the sum of cell cycle genes whose promoters were bound by the protein. The number in the intersection between two circles reflects the numbers of genes whose promoters were bound by both proteins.

FIG. 14B are Venn diagrams representing the overlap in target sites between pairs of regulatory proteins that reside within the same complex.

FIG. 14C is a Venn diagram representing the overlap in target sites between two transcriptional regulators that are not known to be related.

DETAILED DESCRIPTION OF THE INVENTION

Figure 1:
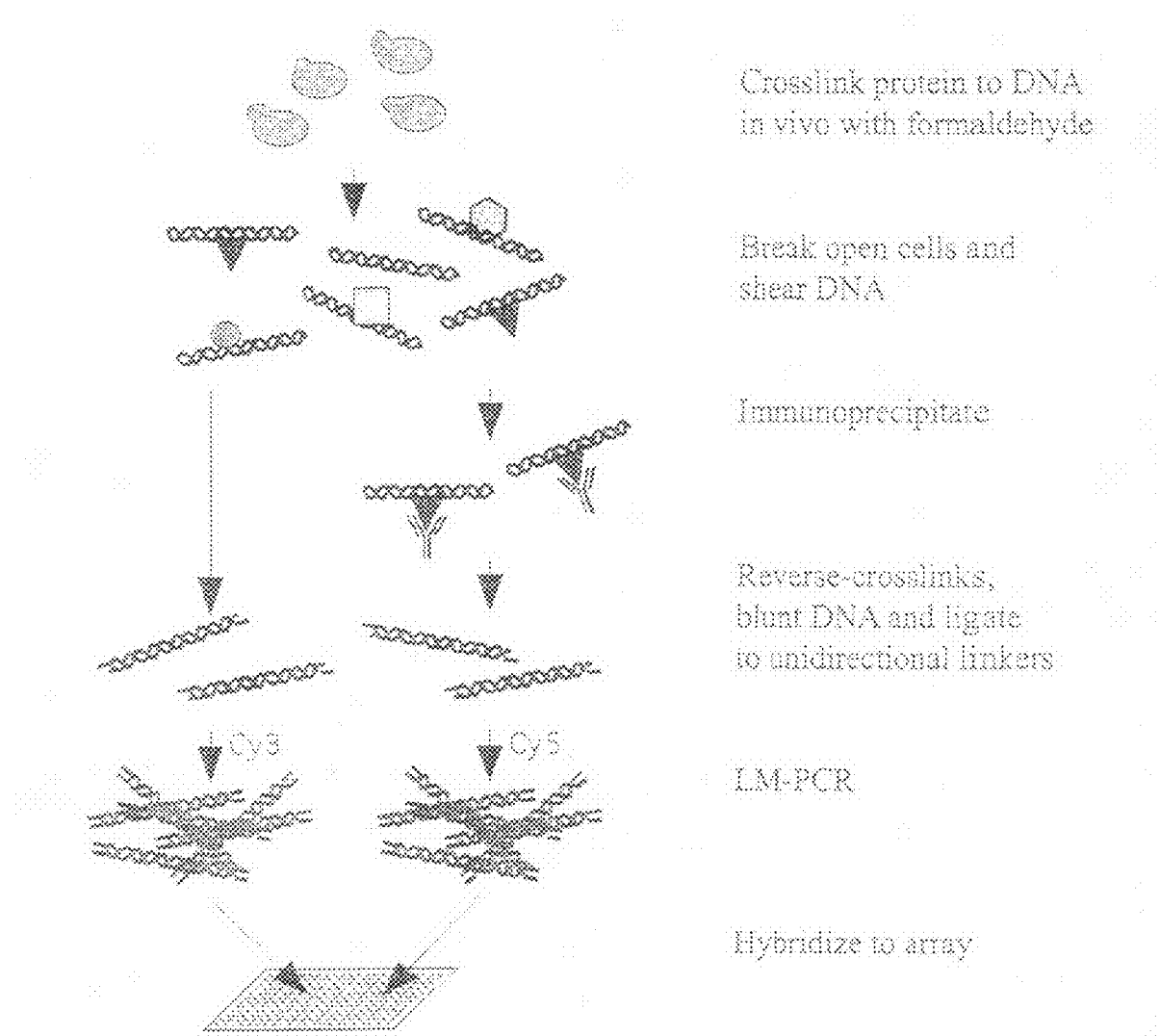
FIG. 1 is an illustration of the Genome-wide Monitoring Protein-DNA interactions described herein.

Understanding how DNA-binding proteins control global gene expression, chromosomal replication and cellular proliferation would be facilitated by identification of the chromosomal locations at which these proteins function in vivo. Described herein is a genome-wide location profiling method for DNA-bound proteins, which has been used to monitor dynamic binding of gene-specific transcription factors and components of the general transcription apparatus in yeast cells. The genome-wide location method correctly identified known sites of action for the transcriptional activators Gal4 and Ste12 and revealed unexpected functions for these activators. The combination of expression and location profiles identified the global set of genes whose expression is under the direct control of specific activators and components of the transcription apparatus as cells responded to changes in their extracellular environment. Genome-wide location analysis provides a powerful tool for further dissecting gene regulatory networks, annotating gene functions and exploring how genomes are replicated.

Accordingly, the present invention provides methods of examining the binding, of proteins to DNA across the genome (e.g., the entire genome or a portion thereof, such as one or more chromosomes or a chromosome regions) of an organism. In particular, the present invention relates to a method of identifying a region (one or more) of genomic DNA of a cell to which a protein of interest binds. In one embodiment, proteins which bind DNA in a cell are crosslinked to the cellular DNA. The resulting mixture, which includes DNA bound by protein and DNA which is not bound by protein is subject to shearing conditions. As a result, DNA fragments of the genome crosslinked to DNA binding protein are generated and the DNA fragment (one or more) to which the protein of interest is bound is removed from the mixture. The resulting DNA fragments are then separated from the protein of interest and amplified using known techniques. The DNA fragment is then combined with DNA comprising a sequence complementary to genomic DNA of the cell, under conditions in which hybridization between the DNA fragments and the sequence complementary to genomic DNA occurs; and the region of the sequence complementary to genomic DNA to which the DNA fragment hybridizes is identified. The identified region is a region of the genome of the cell to which the protein of interest binds.

Also encompassed by the present invention is a method of determining a function of a protein of interest which binds to the genomic DNA of a cell. In this method, DNA binding protein of the cell is crosslinked to the genomic DNA of the cell. DNA fragments of the genome crosslinked to DNA binding protein are then generated, as described above, and the DNA fragment (one or more) to which the protein of interest is bound is removed. The resulting DNA fragment is then separated from the protein of interest and amplified. The DNA fragment is then combined with DNA comprising a sequence complementary to genomic DNA of the cell, under conditions in which hybridization between the DNA fragment and a region of the sequence complementary to genomic DNA occurs; and the region of the sequence complementary to genomic DNA to which the DNA fragment hybridizes is identified and is a region of the genome of the cell to which the protein of interest binds. The identified region is characterized (e.g., a regulatory region) and the characteristic of the identified region indicates a function of the protein of interest (e.g., a transcription factor; an oncoprotein).

The present invention also relates to a method of determining whether a protein of interest which binds to genomic DNA of a cell functions as a transcription factor. In one embodiment, DNA binding protein of the cell is crosslinked to genomic DNA of the cell and DNA fragments of the crosslinked genome are generated. The DNA fragment to which the protein of interest is bound are removed. The resulting DNA fragment is separated from the protein of interest and amplified. The DNA fragment is combined with DNA comprising a sequence complementary to genomic DNA of the cell, under conditions in which hybridization between the DNA fragments and sequence complementary to genomic DNA occurs. The region of the sequence complementary to genomic DNA to which the DNA fragments hybridizes is identified wherein if the region of the genome is a regulatory region, then the protein of interest is a transcription factor.

The methods of the present invention can be used to examine and/or identify DNA binding of proteins across the entire genome of a eukaryotic organism. For example, DNA binding proteins across the entire genome of eukaryotic organisms such as yeast, *Drosophila* and humans can be analyzed. Alternatively, they can be used to examine and/or identify DNA binding of proteins to an entire chromosome or set of chromosomes of interest.

As also described herein, genome-wide location analysis has been used to identify the in vivo genome binding sites for cell cycle transcription factors, in particular genome binding sites for each of the known yeast cell cycle transcription factors. Such analysis is useful to identify genome binding sites (genomic targets) of cell cycle regulators (transcriptional activators) in a variety of cell types and, as also described herein, has resulted in identification of genomic targets of each of the nine known yeast cell cycle transcription activators. One embodiment of the present invention is a method of identifying genes that are expressed in a periodic manner during the cell cycle of a selected cell type and are bound by a cell cycle regulator(s) or cell cycle transcription factors, also referred to transcription(al) regulators/activators. The method is, thus, one of identifying a set of genes where cell cycle factor binding correlates with gene expression. In the method, a set of genes whose factor binding correlates with gene expression at a selected level of stringency of the analysis criteria for binding data is identified. For example, the stringency of the analysis criteria for binding data can be $p<0.001$, $p<0.01$, $p<0.05$ or another selected level and preferably will be selected at such a level that few or no false positives are detected. Cell cycle regulators can be identified by the method of the present invention in a wide variety of cell types (referred to as selected cell types, such as eukaryotic (mammalian, nonmammalian) cells, including human and nonhuman cells (including, but not limited to, yeast and other fungi, worm, fly, avian, murine, canine, bovine, feline, equine, and nonhuman primate cells). The method is carried out, in one embodiment, by identifying a set of genes that is bound in vivo by a cell cycle regulator(s) or transcription factor(s) in a selected cell type (e.g., from a particular organism, which can be human or nonhuman, such as those listed above); comparing that set of genes with genes whose expression levels vary in a periodic manner during the cell cycle of that organism; and identifying genes that are bound by one or more of the cell cycle regulators (identifying genes whose factor binding correlates with gene expression), thus identifying genes whose expression levels vary in a periodic manner during the cell cycle and are bound a cell cycle factor(s). Genes identified in this manner can be characterized, as described herein.

As described herein, a set of yeast genes for which factor binding correlates with gene expression has been identified by comparing the set of genes bound by the nine cell cycle transcription factors with the approximately 800 genes whose expression levels vary in a periodic fashion during the yeast cell cycle. Those genes whose promoters are bound by one or more of the nine transcription factors, particularly those identified with reference to the highest stringency criteria as described herein (highest stringency of analysis criteria for binding data), were investigated and characterized.

Results of work described herein generally support the model for stage-specific regulation of gene expression, described by others, by these activators and extend it to encompass promoters for several hundred cell cycle genes; confirmed results of earlier studies, which established that genes encoding several of the cell cycle transcriptional regulators are themselves bound by other cell cycle functions; revealed that cell cycle transcriptional control is effected by a connected regulatory network of transcriptional activators; and identified a set of promoters bound in vivo by each of the cell cycle regulators, which were further analyzed and shown to comprise consensus binding sequence motifs (see Table 2).

A variety of proteins which bind to DNA can be analyzed. For example, any protein involved in DNA replication such as a transcription factor, or an oncoprotein can be examined in the methods of the present invention.

There are a variety of methods which can be used to link DNA binding protein of the cell to the genome of the cell. For example, UV light can be used. In a particular embodiment, formaldehyde is used to crosslink DNA binding proteins to the genomic DNA of a cell.

In the methods of the present invention, identification of DNA fragments bound to the protein of interest can be removed from the mixture comprising DNA fragment(s) bound to the protein of interest and DNA fragments which are not bound to the protein of interest, using a variety of methods. For example, immunoprecipitation using an antibody (e.g., polyclonal, monoclonal) or antigen binding fragment thereof which binds (specifically) to the protein of interest, can be used. In addition, the protein of interest can be labeled or tagged using, for example, an antibody epitope (e.g., hemagglutinin (HA)).

The DNA fragments in the methods described herein can be amplified using any suitable method. In one embodiment, the DNA is amplified using a non-specific amplification method. For example, ligation-mediated polymerase chain reaction (e.g., see *Current Protocols in Molecular Biology*, Ausubel, F. M. et al., eds. 1991, the teachings of which are incorporated herein by reference) can be used. Thus, the present invention provides a method for non-specifically amplifying DNA fragments from the entire genome of a cell. As shown herein, non-specific amplification can be used without increasing the signal-to-noise ratio. The ability to non-specifically amplify DNA fragments from an entire genome of a cell constitutes a important distinction over other techniques, such as the ChIP technique which relies upon specific primer-based amplification.

In one embodiment, the amplified DNA can be labeled (e.g., a radioactive label, a nonradioactive label such as a fluorescent label) to facilitate identification. In one embodiment, the DNA is labeled using a fluorescent dye, such as Cy5 or Cy3.

The DNA comprising the complement sequence of the genome of the cell can be combined with the isolated DNA fragment to which the protein of interest binds using a variety of methods. For example, the complement sequence can be immobilized on a glass slide (e.g., microarray such as the Corning Microarray Technology (CMT™) GAPS™) or on a microchip. In one embodiment, a glass slide is used which can accommodate an entire genome of a cell (e.g., at least about 7200 spots (DNA)). Conditions of hybridization used in the methods of the present invention include, for example, high stringency conditions and/or moderate stringency conditions. See e.g., pages 2.10.1-2.10.16 (see particularly 2.10.8-11) and pages 6.3.1-6 in *Current Protocols in Molecular Biology*). Factors such as probe length, base composition, percent mismatch between the hybridizing sequences, temperature and ionic strength influence the stability of hybridization. Thus, high or moderate stringency conditions can be determined empirically, and depend in part upon the characteristics of the known nucleic acids (DNA, RNA) and the other nucleic acids to be assessed for hybridization thereto.

The methods of the present invention can further comprise comparing the results to a control (control sample). For example, in one embodiment, the methods of the present invention can be carried out using a control protein which is not a DNA binding protein. In one embodiment, immunoprecipitation is performed using an antibody against an HA or MYC epitope tag. The results of immunoprecipitating the protein of interest containing the tag, and the protein of interest without the tag are compared. The untagged protein should not be immunoprecipitated, and thus, serves as a negative control. Using the methods of the present invention also provides for the ability to compare the sample with the control sample simultaneously. Generally, a test sample if hybridized to an array and compared to a control sample which has been hybridized to a different array and a ratios is calculated to determine binding results. Using the methods described herein, two samples (e.g., a test sample and a control sample) can be hybridized to the same array which allows for elimination of noise due to the use of two arrays (e.g., an array for the test sample and another array for the control sample). The difference between arrays due to manufacturing artifacts is a major source of noise, which can be eliminated using the methods described herein.

As described in the exemplification, a particular embodiment of the present invention comprises the combined use of Chromatin Immunoprecipitation (ChIP) and Genome-wide expression monitoring microarrays. Chromatin immunoprecipitation allows the detection of proteins that are bound to a particular region of DNA. It involves four steps: (1) formaldehyde cross-linking proteins to DNA in living cells, (2) disrupting and then sonicating the cells to yield small fragments of cross-linked DNA, (3) immunoprecipitating the protein-DNA crosslinks using an antibody which specifically binds the protein of interest, and (4) reversing the crosslinks and amplifying the DNA region of interest using the Polymerase Chain Reaction (PCR). Analysis of the PCR product yield compared to a non-immunoprecipitated control determines whether the protein of interest binds to the DNA region tested. However, each region of DNA must be tested individually by PCR. Thus, the ChIP technique is limited to the small set of DNA regions that are chosen to be tested.

In contrast, the present method is not limited to amplifying individual DNA regions by performing PCR with specific primers. Rather the entire genome (test sample) is amplified (e.g., non-specifically) using a Ligation-mediated PCR (LMPCR) strategy. The amplified DNA was fluorescently labeled by including fluorescently-tagged nucleotides in the LM-PCR reaction. Finally, the labeled DNA was hybridized to a DNA microarray containing spots representing all or a subset (e.g., a chromosome or chromosomes) of the genome. The fluorescent intensity of each spot on the microarray relative to a non-immunoprecipitated control demonstrated whether the protein of interest bound to the DNA region located at that particular spot. Hence, the methods described herein allow the detection of protein-DNA interactions across the entire genome.

In particular, DNA microarrays consisting of most of yeast chromosome III plus approximately 15 model genes whose expression have been well studied were constructed. These arrays were used in conjunction with the ChIP technique to study the DNA-binding properties of transcription factors and the transcription apparatus genome-wide. The methods described herein provide insights into the mechanism and regulation of gene expression in eukaryotic cells.

The genome-wide location analysis method described herein allows protein-DNA interactions to be monitored across the entire yeast genome and is diagramed in FIG. 1. The method combines a modified Chromatin Immunoprecipitation (ChIP) procedure, which has been previously used to study in vivo protein-DNA interactions at one or a small number of specific DNA sites, with DNA microarray analysis. Briefly, cells are fixed with formaldehyde, harvested by sonication, and DNA fragments that are crosslinked to a protein of interest are enriched by immunoprecipitation with a specific antibody. After reversal of the crosslinking, the enriched DNA is amplified and labeled with a fluorescent dye (e.g., Cy5) using ligation-mediated PCR (LM-PCR). A sample of DNA that has not been enriched by immunoprecipitation is subjected to LM-PCR in the presence of a different fluorophore (e.g., Cy3), and both immunoprecipitation (IP)-enriched and unenriched pools of labeled-DNA are hybridized to a single DNA microarray containing all yeast intergenic sequences. A single-array error model (Roberts, et al., *Science*, 287:972 (2000)) was adopted to handle noise associated with low-intensity spots and to permit a confidence estimate for binding (P value). When independent samples of 1 ng of genomic DNA was amplified with the LM-PCR method, signals for greater than 99.8% of genes were essentially identical within the error range (P value $\leq 10^{-3}$). The IP-enriched/unenriched ratio of fluorescence intensity obtained from three independent experiments can be used with a weighted average analysis method to calculate the relative binding of the protein of interest to each sequence represented on the array (see FIG. 2).

Figure 5A:
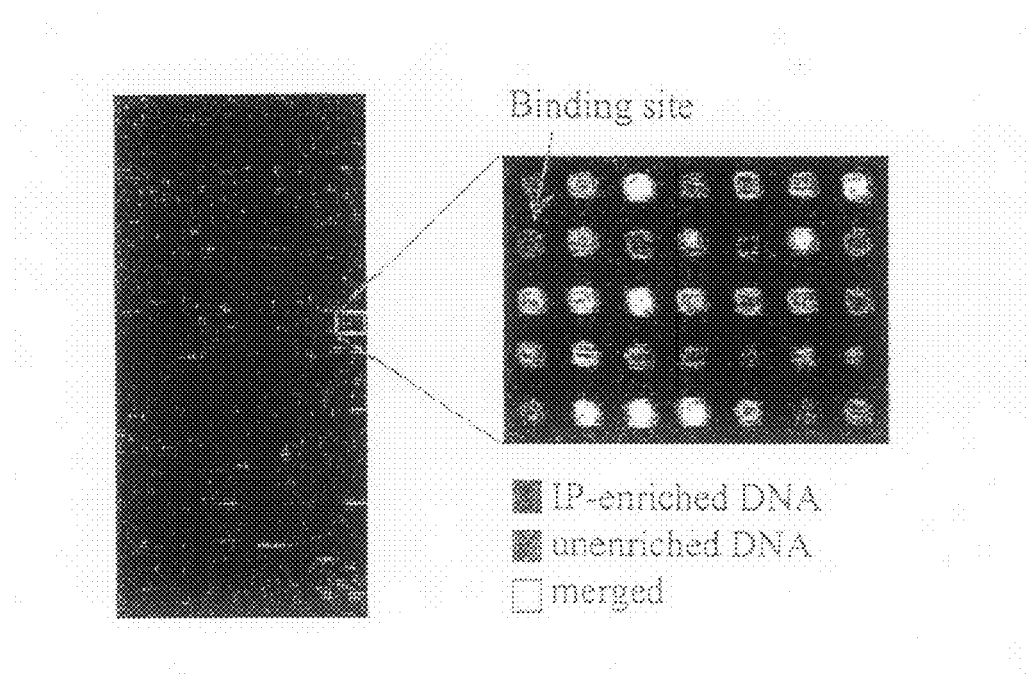
FIG. 5A is an example of a scanned image. The unenriched and IP enriched DNA generates green fluorescence and red fluorescence respectively. The close-up image shows examples of spots for which the red intensity is over-represented, indicating binding of the targeted protein to these DNA sequences.
Figure 5B:
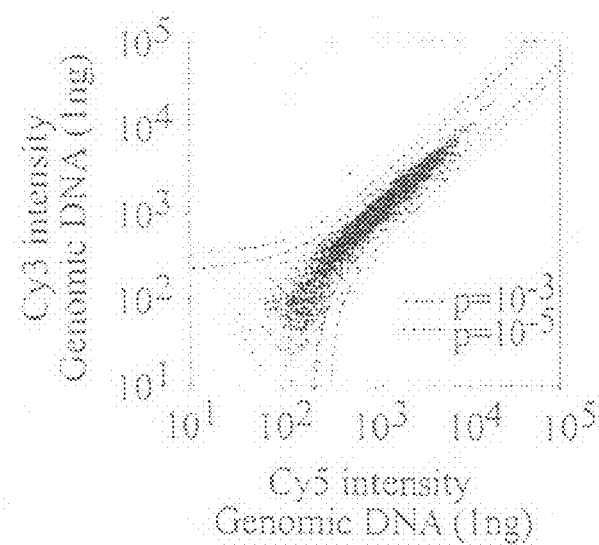
FIG. 5B show that small amounts of DNA can be quantitatively amplified and labeled with Cy3 and Cy5 fluorophores. Cy3- and Cy5-labeled DNA from 1 ng of yeast genomic DNA was prepared using the LM-PCR method described in the text. The resulting DNA samples were mixed and hybridized to a yeast intragenic DNA microarray. Low intensity spots have larger variations than high intensity spots, probably due to background noise.

Four features of the global location profiling method were found to be critical for consistent, high-quality results. First, DNA microarrays with consistent spot quality, and even signal background play an obvious role. An example of an image generated by the technique described herein is shown in FIG. 5A. Second, the LM-PCR method described herein was developed to permit reproducible amplification of very small amounts of DNA; signals for greater than 99.9% of genes were essentially identical within the error range when independent samples of 1 ng of genomic DNA were amplified with the LM-PCR method (FIG. 5B). Third, each experiment was carried out in triplicate, allowing an assessment of the reproducibility of the binding data. And fourth, a single-array error model described by Hughs et al, (2000) was adopted to handle noise associated with low intensity spots and to average repeated experiments with appropriate weights The quantitative amplification of small amount of DNA generates some uncertainty for the low intensity spots. In order to track that uncertainty and to be able to average repeated experiments with appropriate related weights, we adopted an single-array error model that was first described by Hughs et al, (2000). According to this error model, the significance of a measured ratio at a spot is defined by a statistic X, which takes the form $$X=(a_2-a_1)/[\sigma_1^2+\sigma_2^2+f^2(a_1^2+a_2^2)]^{1/2} \quad (1)$$

where $a_{1,2}$ are the intensities measured in the two channels for each spot, $\sigma_{1,2}$ are the uncertainties due to background subtraction, and f is a fractional multiplicative error such as would come from hybridization non-uniformities, fluctuations in the dye incorporation efficiency, scanner gain fluctuations, etc. X is approximately normal. The parameters σ and f were chosen such that X has unit variance. The significance of a change of magnitude |x| is then calculated as $$p=2x(1-Erf(|X|)). \quad (2)$$

Thus, in the methods of the present invention, the data for the intensity of each spot on an array, as well as the intensity and standard deviation around each spot is measured; and this is calculated for both the test sample and the control sample hybridized on the same array. These measurements are used to calculate the enrichment in a probabilistic fashion using a mathematical model. In the methods described herein, each measurement is weighed allowing replicates to be combined appropriately which addresses the susceptibility of spots with lower signals to generate more noise.

EXEMPLIFICATION

Example 1

Design of Yeast Chromosome III and Selected Model Genes Array for the Characterization of Protein-DNA Interactions Array contains all non-overlapping open reading frames (ORF) on Chromosome III (See Table 1). When a sequence contains part or all of two potential reading frames, the larger sequence was chosen to represent the ORF. Any remaining sequence was included in intergenic fragments.

All intergenic regions larger than 100 bp are represented by fragments averaging 500 bp. Where regions are greater than 700 bp, they are broken into multiple fragments of 300 to 600 bps. PCR primers for each region were chosen using the *Saccharomyces* Genomic Database (SGD) "Design Primers" program from Stanford University. The total number of intergenic fragments equals 241 for Chromosome III.

The location and size of open reading frames were determined from the *Saccharomyces* Genomic Database (SGD) functional chromosomal map.

An additional 17 model genes (see the Table) were selected based on their high frequency of citation in transcription literature. Each gene was amplified as well as 1-2 kb upstream and 500 bp downstream of the coding region.

ChIP

Microarray Protocols

PCR Generation of Unmodified Yeast ORF DNA

100 μl reaction generally yields approximately 5-6 μg DNA

RXN Mix:
10.0 μl 10×PCR buffer (Perkin Elmer, AmpliTaq)
8.0 μl 25 mM MgCl2 (Perkin Elmer, AmpliTaq)
10.0 μl 10×dNTPs (2 mM each, Pharmacia 100 mM stocks)
1.0-2.0 μl ORF DNA (Research Genetics, approximately 10 ng)
2.5 μl each universal primer (Research Genetics, 20 μM solution)
1.6 μl diluted Pfu DNA polymerase (diluted 1:100 in water, Strategene, 0.02 U)
1.0 μl AmpliTaq DNA polymerase (5 U, Perkin Elmer)
63.4 μl ddH$_2$O PCR Generation of Yeast Intergenic Regions 100 μl reaction generally yields approximately 5-6 ug DNA RXN Mix:
10.0 μl 10×PCR buffer (Perkin Elmer, AmpliTaq)
8.0 μl 25 mM MgCl2 (Perkin Elmer, AmpliTaq)
10.0 μl 10×dNTPs (2 mM each, Pharmacia 100 mM stocks)
1.0 μl Yeast Genomic DNA (Research Genetics, approximately 100 ng)
5.0 μl each primer (Research Genetics, 20 μM solution)
1.6 μl diluted Pfu DNA polymerase (diluted 1:100 in water, Strategene 0.02 U)
1.0 μl AmpliTaq DNA polymerase (5 U, Perkin Elmer)
58.4 μl ddH$_2$O Cycling for ORF and Intergenic DNA
95° C. 3 min
30 Cycles of:
94° C. 30 sec
60° C. 30 sec
72° C. 2 min PCR Cleanup:

Reactions were cleaned by Qiagen QIAquick 96 PCR purification kits according to die manufacturers' protocol with the following exception. DNA was eluted with 120 µl of T.E. 8.0 (10 mm Tris, 1 mm EDTA, pH8.0). T.E. 8.0 was applied to the Qiagen membrane and allowed to sit 5 minutes before elution. The DNA was collected into a Corning polypropylene 96 well plate.

Reactions were quantified by visualizing 1 µl of the purified DNA on an agarose gel compared to a known quantity of lambda DNA cut with HindIII (Promega).

DNA was stored at −20 until shortly before printing. The DNA was then dried down by speed vac in the Corning microtiter plates to less than 5 µl.

Printing

PCR reactions were resuspended to approximately 0.5 mg/ml in 3×SSC. SSC was made as a 20× stock (3M NaCl, 0.3M Na$_3$citrate.2H$_2$O, pH'd to 7.0 with HCl) and diluted to the desired concentration with H$_2$O.

10-15 µl of the DNA was placed in a Corning 96 or 384 well plate and GAPS coated slides were printed using the Cartessian Robot. PCR products should be greater than 250 pb.

Slide Processing
1. Rehydrated arrays by holding slides over a dish of hot ddH$_2$O (~10 sec).
2. Snap-dried each array (DNA side up) on a 100° C. hot plate for ~3 seconds.
3. UV X-linked DNA to the glass by using a Stratalinker set for 60 mJoules.
4. Dissolved 5 g of succinic anhydride (Aldrich) in 315 mL of n-methyl-pyrrolidinone.
5. To this, added 35 mL of 0.2M NaBorate pH 8.0, and stirred until dissolved (Boric Acid pH'd with NaOH).
6. Soaked arrays in this solution for 15 minutes with shaking.
7. Transferred arrays to 95° C. water bath for 2 minutes.
8. Quickly transferred arrays to 95% EtOH for 1 minute.
9. Air dried slides array side up at a slight angle (close to vertical).

Slide Pre-Hybridization
1. Incubated slide in 3.5×SSC, 0.1% SDS, 10 mg/ml BSA (Sigma) in a Coplin jar for 20 minutes at 50° C. (Place Coplin jar in water bath).
2. Washed slide by dipping in water and then isopropanol.
3. Air dried array side up at slight angle (close to vertical).

Probe Preparation
1. The probe volume should be 20-30 µl for a small coverslip (25 mm$^2$) and 40-60 µl for a large cover slip (24×60 mm).
2. Brought probe (cDNA or PCR based) up to final hyb volume in 3×SSC, 0.1% SDS with 10 µg *E. coli* tRNA (Boehringer-Mannheim).
3. Boiled in heat block for 3-5 minutes.
4. Snapped cool on ice. And spun.

Hybridization
1. Pipetted probe onto slide. Dropped cover slip onto liquid avoiding bubbles.
2. Assembled over 50° C. waterbath in hybridization chamber. Clamped shut.
3. Submerged in 50° C. waterbath overnight.

Scanning
1. Disassembled hybridization right side up.
2. Removed coverslip with fingers or tweezers.
3. Placed in 0.1×SSC, 0.1% SDS at room temperature for 5-10 minutes.
4. Transferred slides to 0.1×SSC for 2.5 minutes and again for 2.5 minutes.
5. Blew dry and scan slide.

Data Analysis

The data generated from scanning was analyzed using the ImaGene software.

TABLE 1

| Yeast ORF | | Model Genes | |
|---|---|---|---|
| YCL001w | RER1 | YOL086c | ADH1 |
| YCL001w-a | | YBR115c | LYS2 |
| YCL002c | | YBR039c | PHO5 |
| YCL004w | PGS1 | YIR019c | FLO11 |
| YCL005w | | YDL215c | GDH2 |
| YCL006c | | YER103w | SSA4 |
| YCL007c | CWH36 | YHR053c | CUP1 |
| YCL008c | STP22 | YKL178c | STE3 |
| YCL009c | ILV6 | YIL163c | SUC2 |
| YCL010c | | YOR202w | HIS3 |
| YCL011c | GBP2 | YJR048w | CYC1 |
| YCL012w | | YJR153c | INO1 |
| YCL014w | BUD3 | YBR020w | GAL1 |
| YCL016c | | YBR019c | GAL10 |
| YCL017c | NSF1 | YDL227c | HO |
| YCL018w | LEU2 | YPL256c | CLN2 |
| YCL019w | | YGR108w | CLB1 |
| YCL020w | | | |
| YCL024w | | | |
| YCL025c | AGP1 | | |
| YCL026ca | FRM2 | | |
| YCL027w | FUS1 | | |
| YCL028w | | | |
| YCL029w | BIK1 | | |
| YCL030c | HIS4 | | |
| YCL031c | RPB7 | | |
| YCL032w | STE50 | | |
| YCL033c | | | |
| YCL034w | | | |
| YCL035c | | | |
| YCL036w | | | |
| YCL037c | SRO9 | | |
| YCL038c | | | |
| YCL039w | | | |
| YCL040w | GLK1 | | |
| YCL041c | | | |
| YCL042w | | | |
| YCL043c | PDI1 | | |
| YCL044c | | | |
| YCL045c | | | |
| YCL046w | | | |
| YCL047c | | | |
| YCL048w | | | |
| YCL049c | | | |
| YCL050c | APA1 | | |
| YCL051w | LRE1 | | |
| YCL052c | PBN1 | | |
| YCL054w | | | |
| YCL055w | KAR4 | | |
| YCL056w | | | |
| YCL057w | PRD1 | | |
| YCL058c | | | |
| YCL059c | KRR1 | | |
| YCL061c | | | |
| YCL063w | | | |
| YCL064c | CHA1 | | |
| YCL065w | | | |
| YCL066w | HMLALPHA1 | | |
| YCL067c | HMLALPHA2 | | |
| YCL068c | | | |
| YCL069w | | | |
| YCL073c | | | |

TABLE 1-continued

| Yeast ORF | Model Genes |
|---|---|
| YCL074w | |
| YCLO75w | |
| YCL076w | |
| YCR001W | |
| YYCR002c | CDC10 |
| YCR003w | MRPL32 |
| YCR004c | YCP4 |
| YCR005c | CIT2 |
| YCR006c | |
| YCR007c | |
| YCR008w | SAT4 |
| YCR009c | RVS161 |
| YCR010c | |
| YCR011c | ADP1 |
| YCR012w | PGK1 |
| YCR014c | POL4 |
| YCR015c | |
| YCR016w | |
| YCR017c | |
| YCR018c | SRD1 |
| YCR018ca | |
| YCR019w | |
| YCR020c | PET18 |
| YCR020CA | MAK31 |
| YCR020wb | HTL1 |
| YCR021c | HSP30 |
| YCR022c | |
| YCR023c | |
| YCR024c | |
| YCR024CA | PMP1 |
| YCR025c | |
| YCR026c | |
| YCR027c | |
| YCR028c | FEN2 |
| YCR028CA | RIM1 |
| YCR030c | |
| YCR031c | RPS14A |
| YCR032w | BPH1 |
| YCR033w | |
| YCR034w | FEN1 |
| YCR035c | RRP43 |
| YCR036w | RBK1 |
| YCR037c | PHO87 |
| YCR038c | BUD5 |
| YCR039c | MATALPHA2 |
| YCR040w | MATALPHA1 |
| YCR041w | |
| YCR042c | TSM1 |
| YCR043c | |
| YCR044c | |
| YCR045c | |
| YCR046c | IMG1 |
| YCR047c | |
| YCR048w | ARE1 |
| YCR051w | |
| YCR052w | RSC6 |
| YCR053w | THR4 |
| YCR054c | CTR86 |
| YCR057c | PWP2 |
| YCR059c | |
| YCR060w | |
| YCR061W | |
| YCR063w | |
| YCR064c | |
| YCR065w | HCM1 |
| YCR066w | RAD18 |
| YCR067c | SED4 |
| YCR068w | |
| YCR069w | SCC3 |
| YCR071c | IMG2 |
| YCR072c | |
| YCR073c | SSK22 |
| YCR073wa | SOL2 |
| YCR075c | ERS1 |
| YCR076c | |
| YCR077c | PAT1 |
| YCR079w | |

TABLE 1-continued

Figure 2:
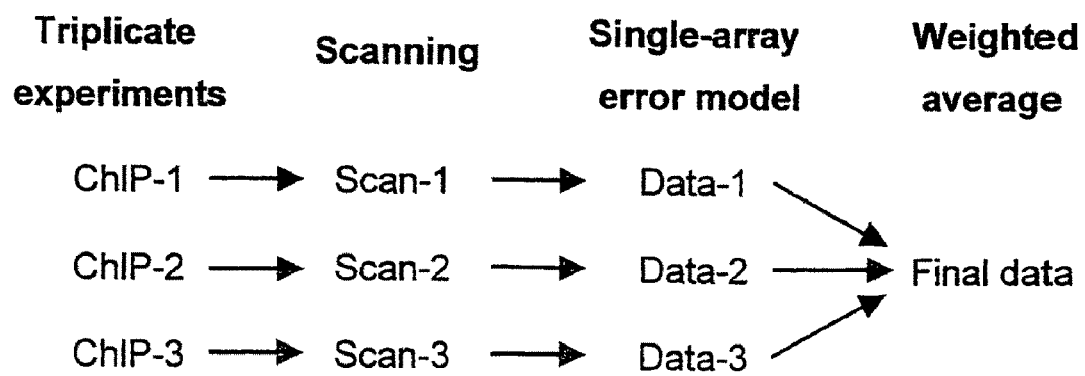
FIG. 2 shows how the relative binding of the protein of interest to each sequence represented on an array was calculated using a weighted average analysis.

| Yeast ORF | Model Genes |
|---|---|
| YCR081w | SRB8 |
| YCR082w | |
| YCR083w | |
| YCR084c | TUP1 |
| YCR085w | |
| YCR086w | |
| YCR087w | |
| YCR088w | ABP1 |
| YCR089w | FIG2 |
| YCR090c | |
| YCR091w | KIN82 |
| YCR092c | MSH3 |
| YCR093w | CDC39 |
| YCR094w | CDC50 |
| YCR095c | |
| YCR096c | A2 |
| YCR097w | A1 |
| YCR098c | GIT1 |
| YCR099c | |
| YCR100c | |
| YCR101c | |
| YCR102c | |
| YCR102wa | |
| YCR103 | |
| YCR104w | PAU3 |
| YCR105w | |
| YCR106w | |
| YCR107w | AAD3 |

Example 2

Genome-Wide Location and Function of DNA-Binding Proteins

Global Analysis of Gal4 Binding Sites

To investigate the accuracy of the genome-wide location analysis method, the analysis was used to identify sites bound by the transcriptional activator Gal 4 in the yeast genome. Gal 4 was selected because it is among the best characterized transcriptional activators, it is known to be responsible for induction of genes necessary for galactose metabolism, and a consensus DNA binding sequence (the $UAS_G$) has been identified for Gal4 in the promoters of the GAL genes. Very little Gal 4 is bound at the $UAS_G$ of the GAL1 and GAL10 promoters when cells are grown in glucose (the repressed state), whereas relatively high levels of Gal4 are bound in galactose (the activated state).

The genome-wide location of epitope-tagged Gal 4p in both glucose and galactose media was investigated in three independent experiments, as described in more detail below. The location analysis experiment identified seven genes previously reported to be regulated by Gal4 and three additional genes encoding activities that are physiologically relevant to cells that utilize galactose as the sole carbon source, but which were not previously known to be regulated by this activator (FIG. 6A).

The set of 24 genes whose promoter regions are most likely to be bound by Gal 4 by the analysis criteria (p-value<0.00001) described herein, is listed in FIG. 6A. Gal4 does not functionally activate all of these genes, however, since only a subset of the genes that share intergenic regions bound by Gal4 will be regulated by this activator (FIG. 6B). To identify genes that are both bound by Gal4 and activated by galactose, genome-wide expression analysis was carried out. The upper panel of FIG. 6A shows genes whose expression is induced in galactose, whereas the lower panel shows genes whose expression is galactose independent. Ten genes were found to be bound by Gal4 (P value≦0.001) and induced in galactose using the critical analysis described herein. These included seven genes previously reported to be regulated by Gal4 (GAL1, GAL2, GAL3, GAL 7, GAL0, GAL80 and GCY1) which were bound Gal4 and were activated in galactose. Three genes whose expression was not previously associated with the Gal 4 activator, MTH, PCL10 and FUR4, were also found to be bound by Gal4 and activated in galactose. Substantially less Gal4 was associated with each of these promoters in cells grown in glucose, as expected. Gal4p was not bound to the promoters of GAL4 and PGM2, genes previously thought to be regulated by Gal 4, although direct evidence for Gal4 binding to these promoters had not been demonstrated. Each of these results was confirmed by conventional ChIP analysis (FIG. 6C), demonstrating that the microarray results accurately reflect results obtained by the conventional approach, which has until now been used to study binding sites individually.

Figure 6D:
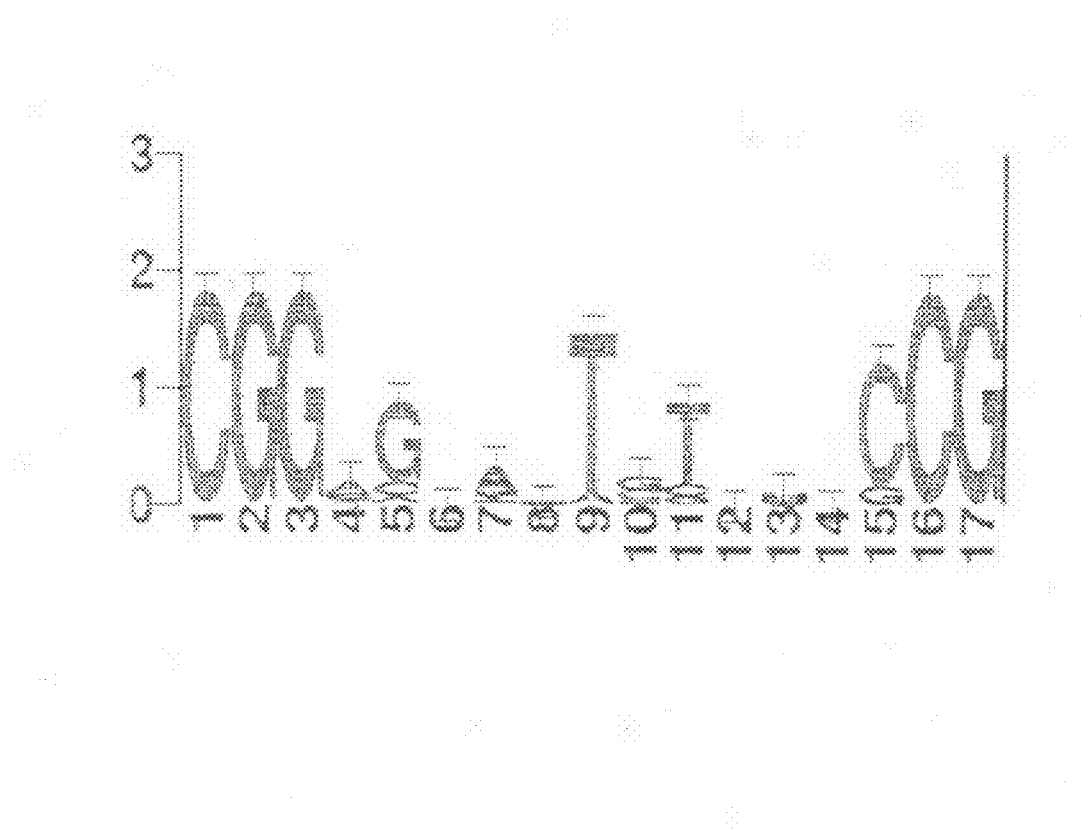
FIG. 6D shows the results of the AlignAce program used to identify a consensus binding site for the Gal4 activator.
Figure 6E:
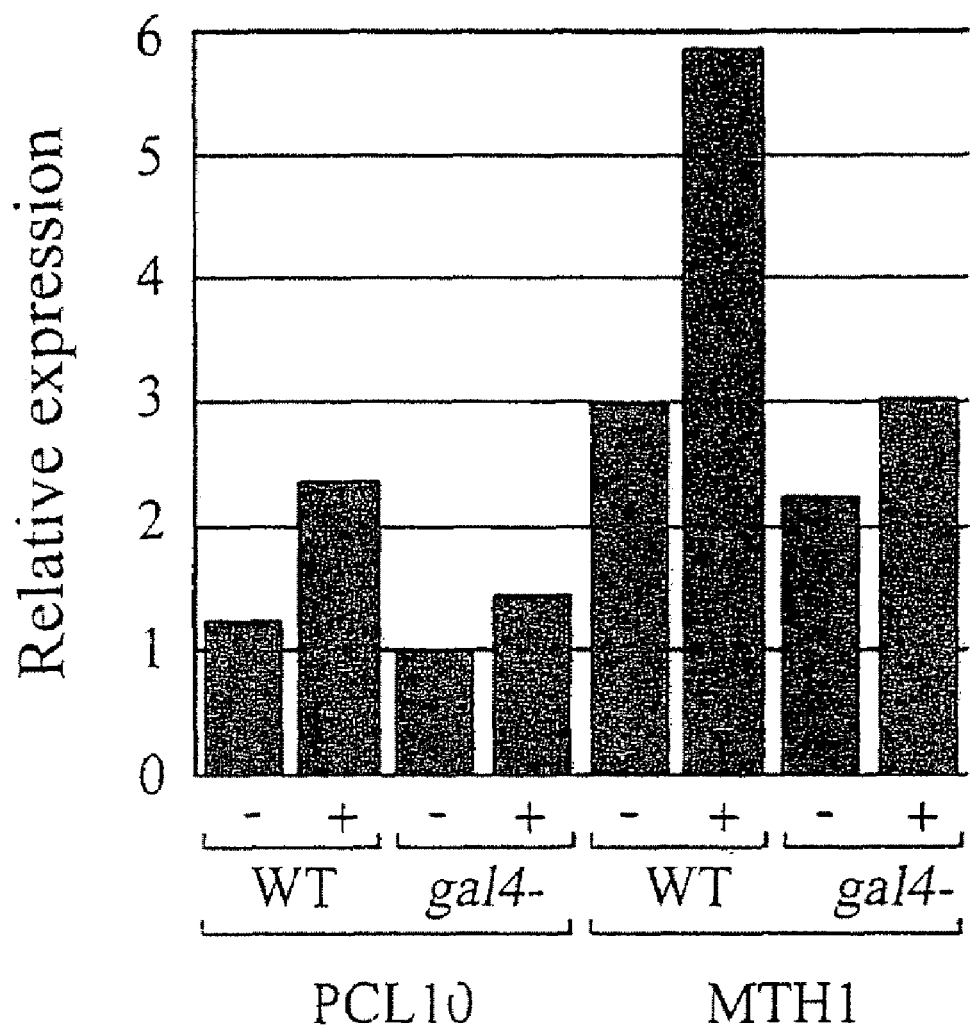
FIG. 6E is a bar graph showing relative expression of PLC10 and MTH1.

The ten genes that are both bound and regulated by Gal4 were selected and the AlignAce program was used to identify a consensus binding site for this activator (FIG. 6D). This binding site sequence is similar to, but refines, the sequence previously determined for Gal4. The Gal4 binding sequence occurs at approximately 50 sites through the yeast genome where Gal4 binding is not detected, indicating that the simple presence of this sequence is not sufficient for Gal4 binding.

Figure 6F:
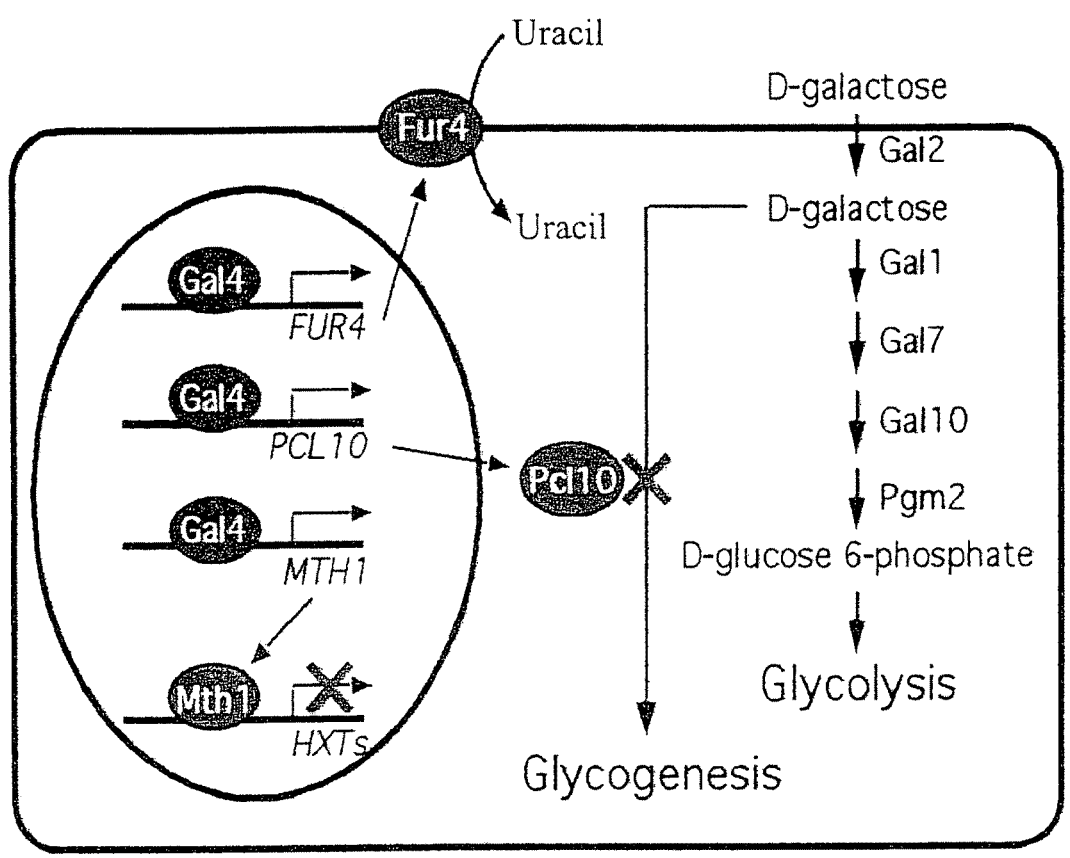
FIG. 6F is a schematic illustrating how the identification of MTH1 and MTH, PCL10 and FUR4 as Gal4-regulated genes reveals how several different metabolic pathways are interconnected.
Figure 6G:
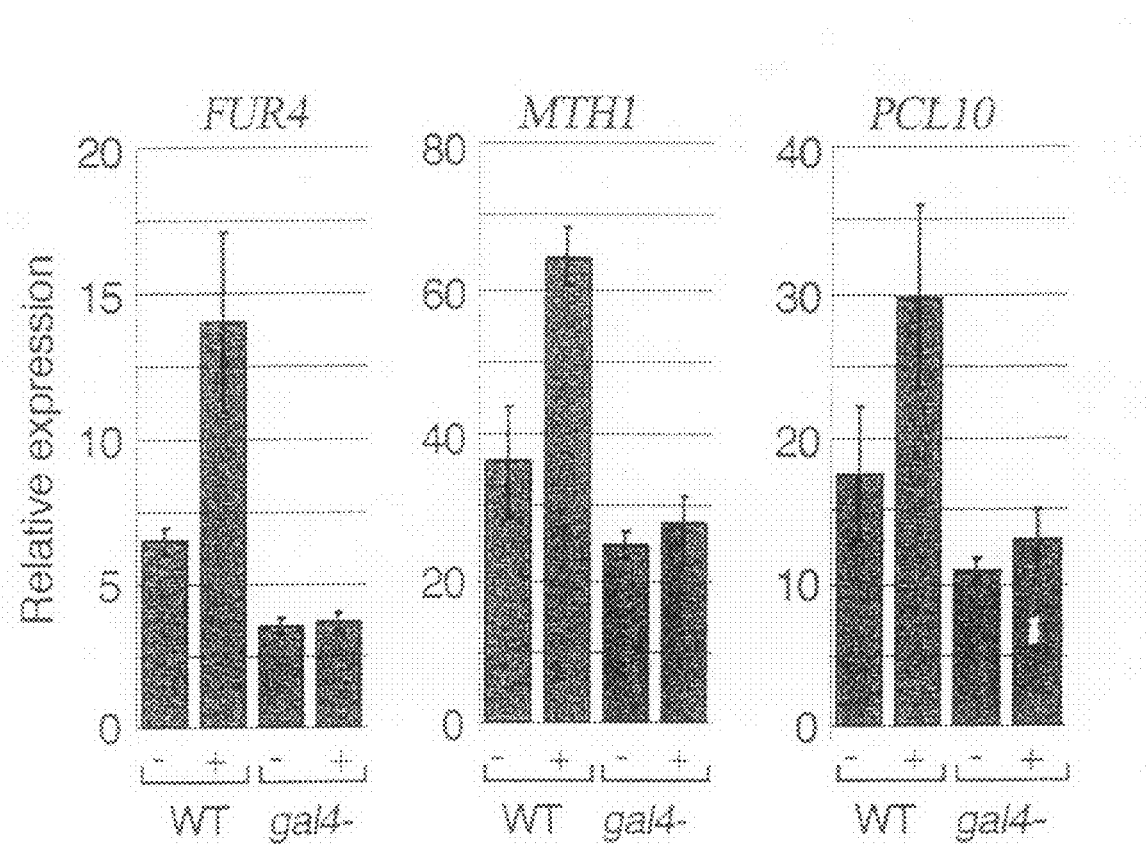
FIG. 6G contains three graphs showing galactose-induced expression of FUR4, MTH1 and PLC10 is GAL4-dependent; samples from wild-type and gal4-strains were taken before and after addition of galactose. The expression of FUR4, MTH1 and PLC10 was monitored by quantitative reverse transcriptase-PCR (RT-PCR) and was quantified by phosphoimaging.

Three genes whose expression was not previously associated with the Gal4 activator, MTH, PCL10 and FUR4, were found to be bound by Gal4 and activated in galactose (FIG. 6G). The identification of MTH1, PCL10 and FUR4 as Gal4-regulated genes reveals previously unknown functions for Gal4- and explains how regulators of several different metabolic pathways can be coordinated. It is likely that these three genes are genuine Gal4p targets because they share the following three features with the well established Gal 4-dependent GAL genes. MTH, PCL10 and FUR4 are galactose-induced (FIG. 6A). Galactose induction depends on Gal4 (FIG. 6C). MTH, PCL10 and FUR4 promoters are bound by Gal4 when cells are grown in galactose but not in glucose (FIG. 6A). The binding of Gal4p to the MTH, PCL10 and FUR4 promoters was verified by conventional CHIP analysis (FIG. 6C).

The identification of MTH1 and MTH, PCL10 and FUR4 as Gal4-regulated genes reveals how regulation of several different metabolic pathways are interconnected (FIG. 6F). MTH1 encodes a transcriptional repressor of many genes involved in metabolic pathways that would be unnecessary when cells utilize galactose as a sole carbon source. Among the most interesting of its targets are a subset of the HTX genes involved in hexose transport. The results described herein indicate that the cell responds to galactose by modifying (increasing) the concentration of its galactose transporters at the membrane in a Gal4-dependent fashion at the expense of other transporters, In other words, while Gal4 activates expression of the galactose transporter gene GAL2, Gal4 induction of the MTH1 repressor gene, leads to reduced levels of glucose transporter expression. The Pc110 cyclin associates with Pho85p and appears to repress the formation of glycogen. The observation that PCL10 is Gal4-activated indicates that reduced glycogenesis occurs to maximize the energy obtained from galactose metabolism. FUR4 encodes a uracil pennease and its induction by Gal 4 may reflect a need to increase intracellular pools of uracil to permit efficient uridine 5'-diphosphate (UDP) addition to galactose catalyzed by Gal 7.

Previous studies have shown that Gal4 binds to at least some GAL gene promoters when cells are grown on carbon sources other than galactose, as long as glucose is absent. Genome-wide location analysis of Gal4 in cells grown on raffinose was repeated and it was found that the results were essentially identical to those obtained when cells were grown on galactose. These results indicate that Gal4 exhibits the same binding behavior at all its genomic binding sites and demonstrate that the genome-wide location method is highly reproducible.

Global Analysis of Ste12 Binding Sites

The genome-wide binding profile of the DNA-binding transcription activator Ste12 was also investigated. Ste12 is of interest because it has a defined cellular role—it is key to the response of haploid yeast to mating pheromones—but only a few genes regulated by Ste12 have been identified. Activation of the pheromone-response pathway by mating pheromones causes cell cycle arrest and transcriptional activation of more than 200 genes in a Ste12-dependent fashion. However, it is not clear which of these genes is directly regulated by Ste12 and which are regulated by other ancillary factors. Expression analysis using ste12 mutant cells has shown that Ste12 is required for the pheromone induction of all of these genes. However, the mechanism by which Ste12 activates transcription of these genes in response to pheromone has not been elucidated.

Figure 7B:
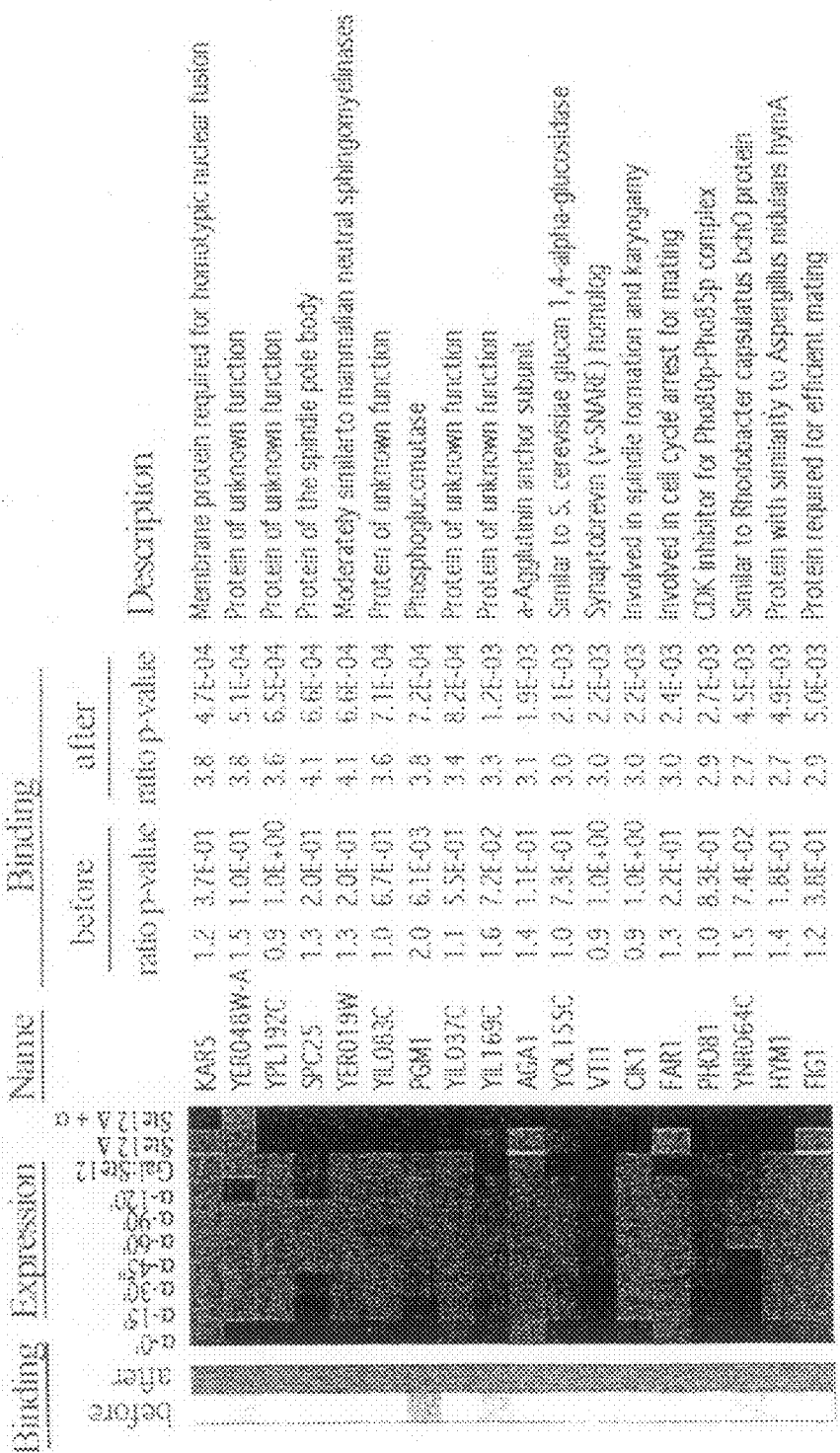
FIG. 7 lists the set of genes whose promoter regions are most likely to be bound by Ste112 by the analysis criteria described herein.
Figure 7C:
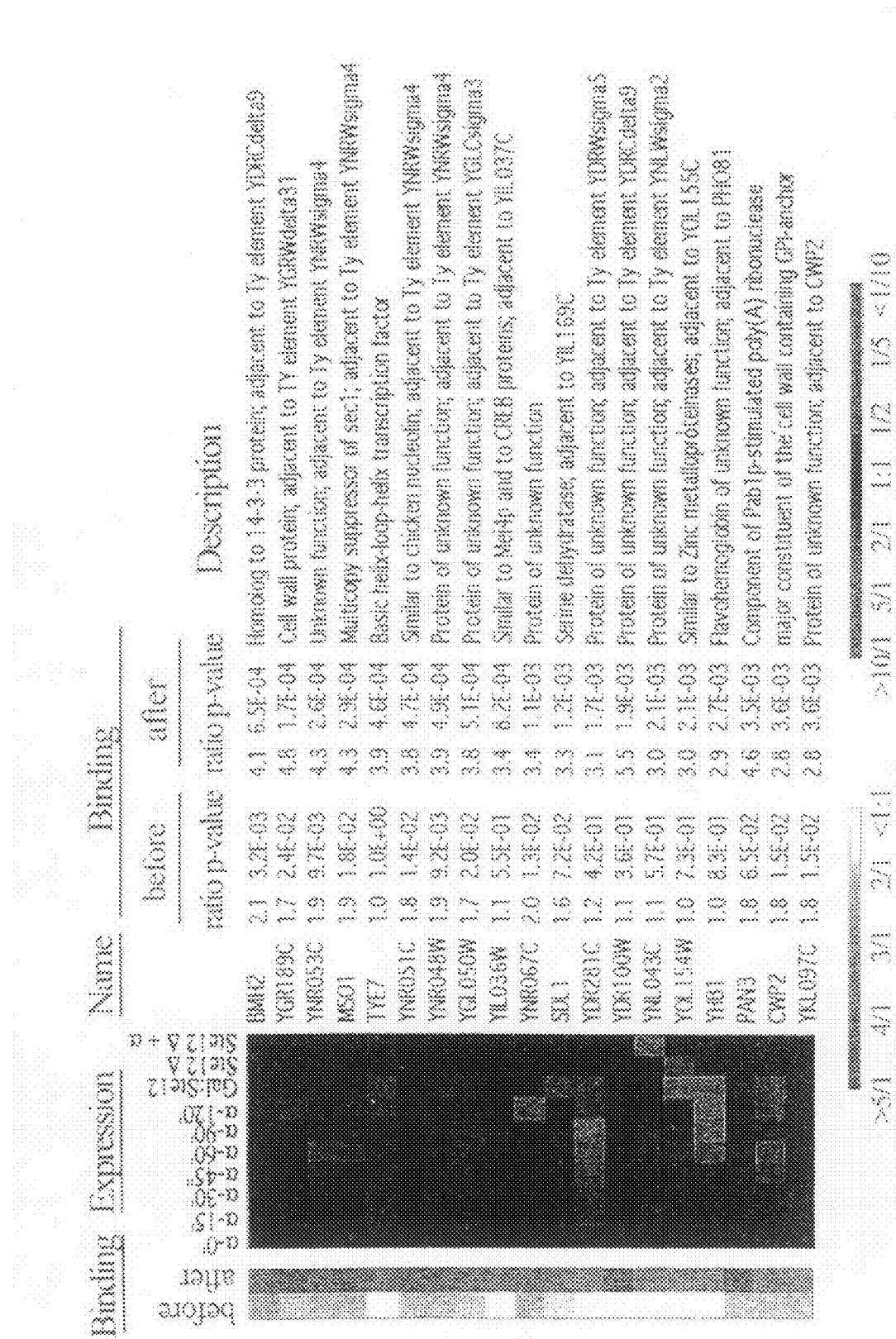
Figure 8:
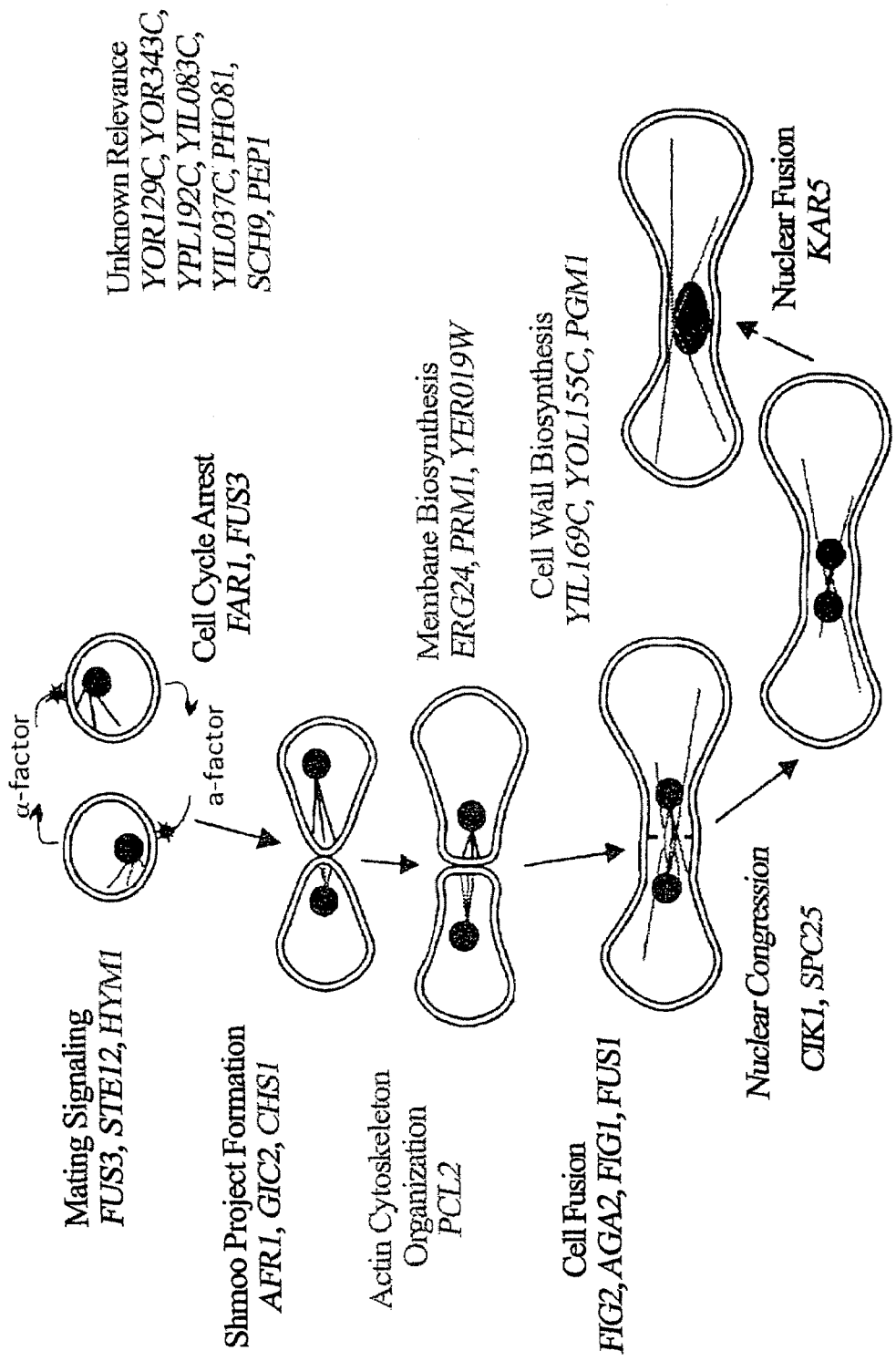
FIG. 8 is a schematic of a model summarizing the role of Ste12 target genes in the yeast mating pathway. Gray boxes denote the cellular processes known to be involved in mating; yellow boxes denote cellular processes that are likely associated with mating. Genes in black were previously reported to be associated with the mating process; genes in red are Ste12 targets that likely play a role in mating.

The genome-wide location of epitope-tagged Ste12p before and after pheromone treatment was investigated in three independent experiments. The set of genes whose promoter regions are most likely to be bound by Step 12 by the analysis criteria (p-value<0.005) described herein is listed in FIG. 7; the upper panel shows genes whose expression is induced by alpha factor, whereas the lower panel shows genes whose expression is not significantly induced by alpha factor. Of the genes that are induced by alpha factor and are bound by Ste12, 11 are known to participate in various steps of the mating process (FIG2, AFR1, GIC2, STE12, KAR5, FUS1, AGA1, FUS3, CIK1, FAR1. FIG1) (FIG. 8). FUS3 and STE12 encode components of the signal transduction pathway involved in the response to pheromone (Madhani et al., *Trends Genet.*, 14:151 (1999)); AFR1 and GIC2 are required for the formation of mating projections (Konopka et al., *Mol. Cell Biol.*, 13:6876 (1993); Brown et al., *Genes Dev.*, 1:2972 (1997); Chen et al., *Genes Dev.* 11:2998 (1997)); FIG2, AGA1, FIG1 and FUS1 are involved in cell fusion (Erdman et al., *J. Cell Biol.*, 140:461 (1999); Roy et al., *Mol. Cell Biol.*, 11:4196 (1991); Truehart et al., *Mol. Cell biol.*, 7:2316 (1987); McCaffrey et al., *Mol. Cell Biol.*, 7:2680 (1987)); and CIK1 and KAR5 are required for nuclear fusion (Marsh, L. and Rose, M. D. in *The Molecular and Cellular Biology of the Yeast Saccharomyces*, J. R. Pringle, J. R. Broach, E. W. Jones, Eds. (Cold Spring Harbor Laboratory Press, Cold Spring Harbor, 1997), vol. 3, pp. 827-888). Furthermore, FUS3 and FAR1 are required for pheromone-induced cell cycle arrest (Chang et al., *Cell,* 63:999 (1990); Fujimura, *Curr. Genet.,* 18:395 (1990)).

Ste12 binds to some promoters in the absence of pheromone signaling, however, its binding to most genes is enhanced by alpha factor. Interestingly, Ste12p is bound to its own promoter both before and after pheromone treatment. Together, the binding and expression data argue that the regulation of the STE12 gene involves a positive feedback loop. STE12 expression is increased immediately after pheromone treatment, indicating that the bound but inactive Ste12 activator is rapidly converted to an active form. Increased expression of STE12 gene would allow more Ste12p to be made and this would, in turn, activate its genes.

Twenty-four genes whose expression were not previously associated with Ste12 and the mating process were found to be bound by Ste12 and activated by alpha factor. Considering that their pheromone induction is eliminated in Ste12 mutant cells, it is likely that these 24 genes are also genuine Ste12 targets. The identities of these genes indicate interesting details about various steps of the mating process. For example, one Ste12 target gene, PCL2, encodes a G1 cyclin that forms complexes with the cyclin-dependent kinase (cdk) Pho85. The Pcl2-Pho85 and PCl2-Pho85 complexes act in concert with Cln1-Cdc28 and Cln-2-Cdc28 cyclin dependent kinase complexes to promote G1 cell cycle progression (Measday et al., 1994). The Pcl2-Pho85 kinase complex has a substrate specificity that is overlapping but different from that of the Cln1-Cdc28 and Cln2-Cdc28. During the mating process, haploid yeast cells are arrested at start of the late G1 phase, due to the inhibition of Cln1-Cdc28 and Cln9-Cdc28 activities by Farl, which is encoded by another Ste12 target gene. Activation of PCL2 by Ste12 after pheromone treatment indicates that increased Pho85 complex activities are likely necessary to compensate for the loss of Cdc28 activities.

Most Ste12 target genes identified by analysis of genome locations of Ste12 and expression profiles during pheromone induction encode proteins involved in various steps of the mating response. Among them are 11 previously uncharacterized. The cellular roles for these genes, including YNL279W, YOR129C, YOR343C, YPL192C, YER019W, YIL083C, YIL037C, YIL169C, YNL105W, YOL155C and YNR064C, are therefore most likely related to mating.

Among the Ste12 target genes identified in this study that were not previously reported to be involved in mating, many are involved in processes likely to be relevant to mating. CSH1, PCL2, ERG24, SPC25, HYM1, and PGM1 encode proteins involved in cell wall biosynthesis, cell morphology, membrane biosynthesis, nuclear congression and regulation of gene expression. Furthermore, YER019W, YOR129C and SCH₉ are among genes that are cell cycle regulated (Spellman et al., *Mol. Cell Biol.*, 9:3273 (1999).

The genes that are regulated by Ste12 can be divided into two classes: those bound by Ste12 both before and after pheromone exposure (e.g., STE12, PLC2, FIG2 and FUS1), and those bound by Ste12 only after exposure to pheromone (e.g., CKI1 and CHS1). The first class of genes is induced immediately after pheromone exposure, most likely by a mechanism that converts an inactive DNA-bound Ste12 protein to an active transcriptional activator. This could take place by removal of repressors of Ste12 such as Dig1/Rst1 and Dig2/Rst2 (Olson et al., *Mol. Cell Biol.*, 20:4199 (2000)). In the second class of genes, induction of transcription is relatively slow. In this case, the binding of Ste12 appears to be limited before pheromone exposure. It is also possible that the epitope tag on Ste12 is masked at these promoters before pheromone treatment, perhaps due to the presence of additional regulatory proteins.

Ste12 has also been implicated in other cellular processes. Together with Tec1, Ste12 regulates the filmamentation of diploid cells and invasive growth in haploids. Two genes, TEC1 and FLO11, have been identified as Ste12 targets in filamentous growth pathway. Ste12 binding to these genes either in the presence or absence of alpha factor was not detected. It is likely that Ste12p's binding to these promoters is regulated by different physiological conditions.

As shown herein, a combination of genome-wide location and expression analysis can identify the global set of genes whose expression is controlled directly by transcriptional activators in vivo. The application of location analysis to two yeast transcriptional activators revealed how multiple functional pathways are coordinately controlled in vivo during the response to specific changes in the extracellular environment. All of the known targets for these two activators were confirmed, and functional modules were discovered that are regulated directly by these factors.

Expression analysis with DNA microarrays allows identification of changes in mRNA levels in living cells, but the inability to distinguish direct from indirect effects limits the interpretation of the data in terms of the genes that are controlled by specific regulatory factors. Genome-wide location analysis provides information on the binding sites at which proteins reside through the genome under various conditions in vivo.

TABLE 2

Consensus Binding Motifs of Promoters Bound by
Yeast Cell Cycle Transcriptional Regulators

| Factor | Motif[a] | Reference[b] |
|---|---|---|
| MbpI | 2<br>1 A  A  G A      T T<br>0 T G G A A T C G C G C C | Tavazoie et al., 1999 |
| Swi4 | 2<br>1 A  A A  G  G A   A<br>0 C A T T C A C C T A A T | Tavazoie et al., 1999 |
| Mcm1/Fkh2 | 2<br>1     C C   A T     G    A A G T A A A<br>0 T T T T T T T A T A   G C G A A T T A C C C G C A | Althoefer et al., 1995 |
| Mcm1 | 4<br>3            T<br>2           A<br>1 A T T    T A  T T G G  A<br>0 T A T A C C G C A C C A T G T A | Tavazoie et al., 1999 |

TABLE 2-continued

Consensus Binding Motifs of Promoters Bound by
Yeast Cell Cycle Transcriptional Regulators

| Factor | Motif[a] | Reference[b] |
|---|---|---|
| Ace2 | 2<br>1 G A A   C A<br>0 A C G C A C G C A | Dohrmann et al., 1996 |
|  | 2<br>1           A T A G  T<br>0 A G G G A    T A T A  G G |  |
| Swi5 | 2<br>1 G           C<br>0 C G A G G   G C A G C A | Tebb et al., 1993 |
|  | 2<br>1 G       G C         G<br>0 C T  A T G A T  T G G  T |  |
| Fkh1 & Fkh2 | 2<br>1 G<br>0 A T A A A C A A | Zhu et al., 2000 |
| Fklh | 2<br>1 C  G C                 G C G G C<br>0 G  T G   G G       G    C G C C T |  |
|  | 2<br>1    T T T<br>0 T C C C C G A G A A A T |  |
|  | 2<br>1 G G C C G G G G C G G G T<br>0 T  T T T  C A C C A T C A C |  |

[a]Sequence logo (schneider and Stephens, 1990) presentation of motifs that were found using the group of promoters bound by each activator as an input to AiiganACE. Presented are motifs specific to the input set of promoters. The specificity source (Hughes et al., 2000) for the motifs (top to bottom) are $10^{-21}$, $10^{-15}$, $10^{-25}$, $10^{-28}$, $10^{-7}$, $10^{-14}$, $10^{-19}$, $10^{-11}$, $10^{-13}$, $10^{-15}$, $10^{-24}$,
$10^{-17}$
[b]References for previous descriptions of similar motifs Example 3

Serial Regulation of Transcriptional Regulators in the Yeast Cell Cycle

Experimental Procedures

Tagging and Yeast Strains

The cell cycle activators Swi4, Mbp1, Swi5, Fkh1, Fkh2, Ndd1 Mcm1, and Ace2 were tagged with a multicopy myc epitope by inserting the epitope coding sequence into the normal chromosomal loci of these genes. Vectors developed by Cosma et al. *Cell*, 97:299-311 (1998) were used for amplifying a fragment that contains the repeated myc tag coding sequence flanked by 50 bp from both sides of the stop codon of the gene. The PCR products were transformed into the W303 strain Z1258 (MATα, ada2-1, lrp1-1, can1-100, leu2-3, 112, his3-11, 15, ura3) to generate the tagged strains (Z1335, Z1372, Z1373, Z1446, Z1370, Z1369, Z1321, and Z1371, respectively). Clones were selected for growth on TRP plates, the insertion of the tagged sequence was confirmed by PCR, and expression of the epitope-tagged protein was confirmed by Western blotting using an anti-Myc antibody (9E11). A strain containing a myc-tagged version of Swi5 (Z1407) was obtained from K. Nasmyth.

Genome-Wide Location Analysis

Genome-wide location analysis as described in Ren et al. *Science*, 290:2306-2309 (2000) was used to identify genome binding sites for the transcription factors. Briefly, yeast strains containing a myc-tagged version of the protein of interest were grown to mid log phase (OD 0.6-1.0), fixed with 1% formaldehyde for 30 minutes, harvested and disrupted by sonication. The DNA fragments crosslinked to the protein were enriched by immunoprecipitation with anti-myc specific monoclonal antibody (9E11), thus obtaining an enrichment of the in vivo binding sites. After reversal of the crosslinks, the enriched DNA was amplified and labeled with a fluorescent dye (Cy5) with the use of a ligation-mediated polymerase chain reaction (LM-PCR). A sample of DNA that was not enriched by immunoprecipitation was subjected to LM-PCR in the presence of a different fluorophore (Cy3), and both immunoprecipitation (IP)-enriched and -unenriched pools of labeled DNA were hybridized to a single DNA microarray containing all yeast intergenic sequences. Microarray design and production was as described in Ren et al. *Science*, 290:2306-2309 (2000).

Images of Cy3 and Cy5 fluorescence intensities were generated by scanning the arrays using a GSI Lumonics Scanner. The Cy3 and Cy5 images were analyzed using ArrayVision software, which defined the grid of spots and quantified the average intensity of each spot and the surrounding background intensity. The background intensity was subtracted from the spot intensity to give the final calculated spot intensity. The intensity of the two channels was normalized according to the median. For each spot, the ratio of corrected Cy5/Cy3 intensity was computed. Each experiment was carried out in triplicate, and a single-array error model was used to handle noise, to average repeated experiments with appropriate weights, and to rank binding sites by p value as described (See also http://web.wi.mit.edu/young/cellcycle which is incorporated herein by reference; Ren et al. *Science*, 290:2306-2309 (2000)).

The intergenic regions present on the array were assigned to the gene or genes found transcriptionally downstream. Where a single intergenic region contains promoters for two divergently transcribed genes, the intergenic region was assigned to the gene or genes expressed during the cell cycle according to the Spellman et al. *Mol. Cell Biol. Cell*, 9:3273-3297 (1998) analysis. The Spellman et al. 1998 analysis was chosen because it incorporates all available yeast cell cycle expression data. Promoter regions detected with a p value<0.001 were included for further analysis.

Statistics

In order to explore the statistical significance of the overlap between the set of targets of a factor and the genes expressed in a particular cell cycle stage, the hypergeometric distribution as described in Tavazole et al. *Nat. Genet.*, 22.281-285 (1998) was used.

Results

Figure 9A:
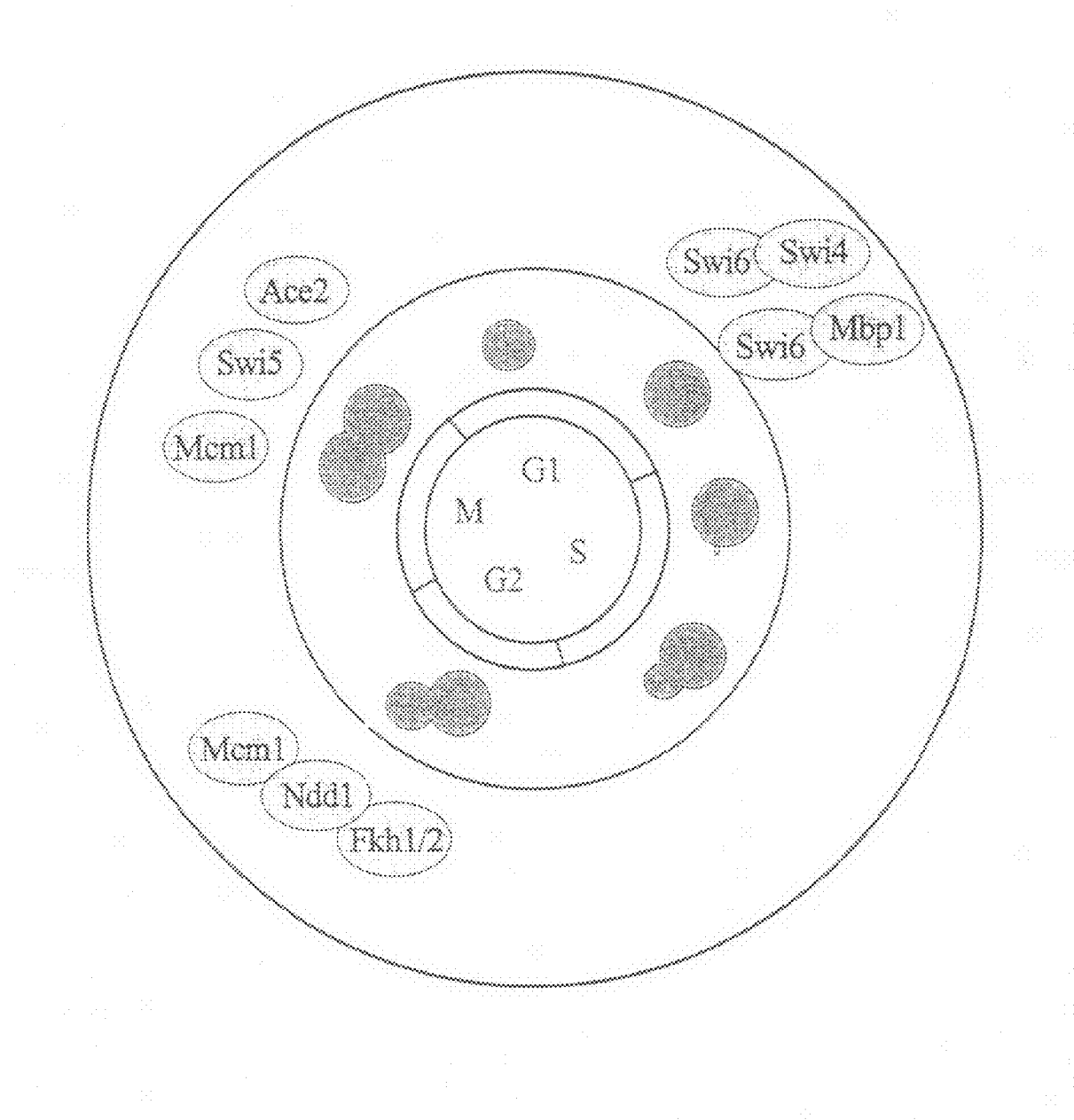
FIGS. 9A-9C show the cell cycle transcriptional regulators study design.
Figure 9B:
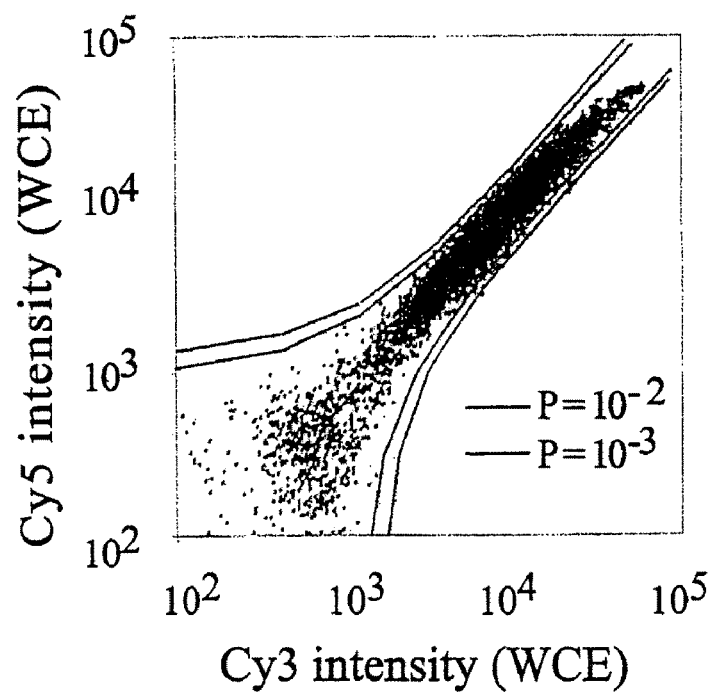
Figure 9C:
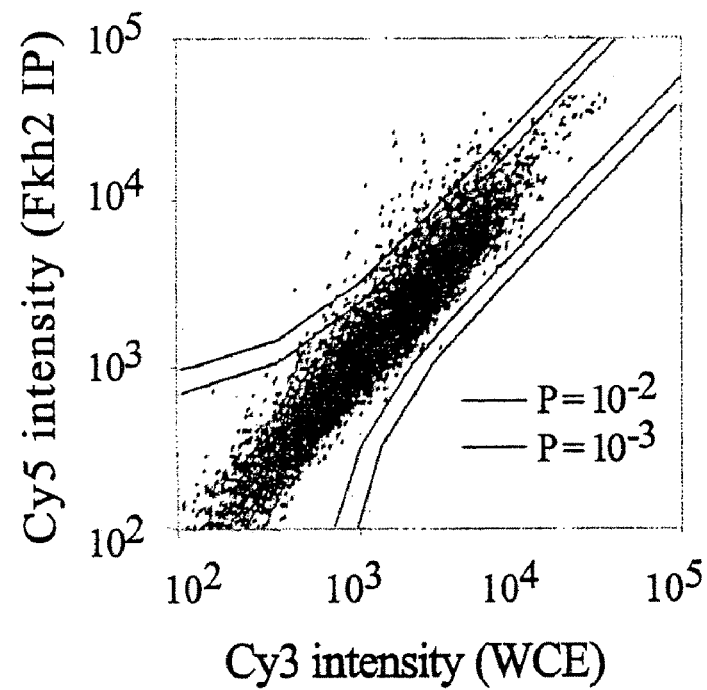

Genome-wide location analysis (Ren et al., *Science*, 290: 2306-2309 (2000)) was used to identify the in vivo genome binding sites for each of the known cell cycle transcription factors (FIGS. 9A and 9B). Yeast strains, each containing a myc-tagged version of Mbp1, Swi4, Swi6, Mcm1, Fkh1, Fkh2, Ndd1, Swi5, or Ace2, were grown in asynchronous cultures to mid log phase and subjected to location analysis as described previously (Ren et al., *Science*, 290:2306-2309 (2000)). Each experiment was carried out in triplicate, and a single array error model was used to handle noise, to average repeated experiments with appropriate weights, and to rank binding sites by p value (FIGS. 9B and 9C). Asynchronous cultures were used because previous studies showed that the results obtained for Swi4 in genome-wide location experiments are essentially identical in unsynchronized and arrested cultures (Iyar et al., *Nature*, 409:533-536 (2001)), and because it was not feasible to obtain high quality datasets in triplicate at multiple cell cycle time points for all nine factors.

The regulation of the cell cycle expression program by each of the nine factors is summarized in FIGS. 10A-10D. The binding of a transcriptional activator to the promoter region of a gene suggests that the activator has a regulatory effect oil the gene, but it is also possible that the activator does not fully or even partially control the gene. For this reason, we have identified the set of genes where factor binding correlates with gene expression, an approach that produced highly accurate information on transcription factor function in previous studies with other factors (Ren et al., *Science*, 290: 2306-2309 (2000)). The set of genes bound by the nine cell cycle transcription factors was compared to the set of approximately 800 genes whose expression levels vary in a periodic fashion during the yeast cell cycle (Spellman et al. *Mol. Cell Biol. Cell*, 9:3273-3297 (1998)). The proportion of the 800 genes whose promoters are bound by one or more of the nine transcription factors studied here varies with the stringency of the one analysis criteria for binding data (27% at p<0.001, 37% at p<0.01; 50% at p<0.05). Further discussion was focused on results obtained with the highest stringency criteria (p<0.001) because a previous investigation using this approach detected no false positives in followup studies (Ren et al., *Science*, 290:2306-2309 (2000); http://web.wi.mit.edu/young/cellcycle; http://www.cell.com/cgi/content/full/106/6/697/DC1).

Collaboration of Regulators in Periodic Gene Expression

A model for transcriptional control of cell cycle genes has been developed that is based on studies involving a relatively small number of genes. In this model, MBF and SBF control expression of late G1 genes (Koch et al., *Curr. Opin. Cell Biol.*, 6:451-459 (1994)); a complex of Mcm1, Ndd1, and Fkh1/Fkh2 controls G2/M genes (Koranda et al., *Nature*, 406:94-98 (2000); Kumar et al., *Curr. Biol.*, 10:896-906 (2000); Pic et al., *Embo J.*, 19.3750-3761 (2000); Zhu et al., *Nature*, 406:90-94 (2000)); and Mcm1, Swi5, and Ace2 regulate genes expressed in M/G1 (McBride et al., *J. Biol. Chem.*, 274:21029-21036 (1999); McInerny al., *Genes Dev.*, 11:1277-1288 (1997)). The genome-wide binding data for these activators support this model (FIGS. 10A-10B) and provide compelling evidence for collaboration among specific factors in genome-wide regulation. Mbp1, Swi4, and Swi6 bound predominantly to promoter regions of late G1 genes ($p<10^{-14}$, $p<10^{-18}$, and $p<10^{-20}$ respectively), Swi5 and Ace2 to M/G1 genes $p<10^{-14}$ and $p<10^{-3}$, respectively), and Mcm1, Fkh2, and Ndd1 to G2/M genes ($p<10^{-14}$, $p<10^{-15}$, and $p<10^{-21}$, respectively). Thus, the data described herein generally support the model for stage-specific regulation of gene expression by these activators and extend it to encompass promoters for several hundred cell cycle genes.

Figure 10A:
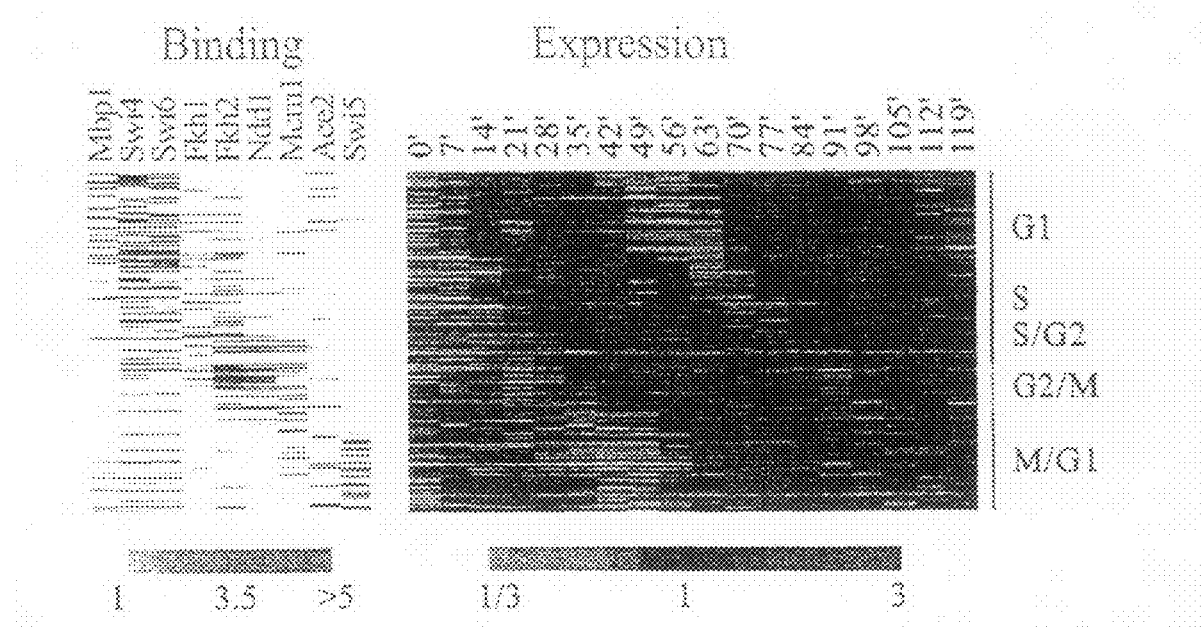
FIGS. 10A-10B show genome-wide location of the nine cell cycle transcription factors.
Figure 10B:
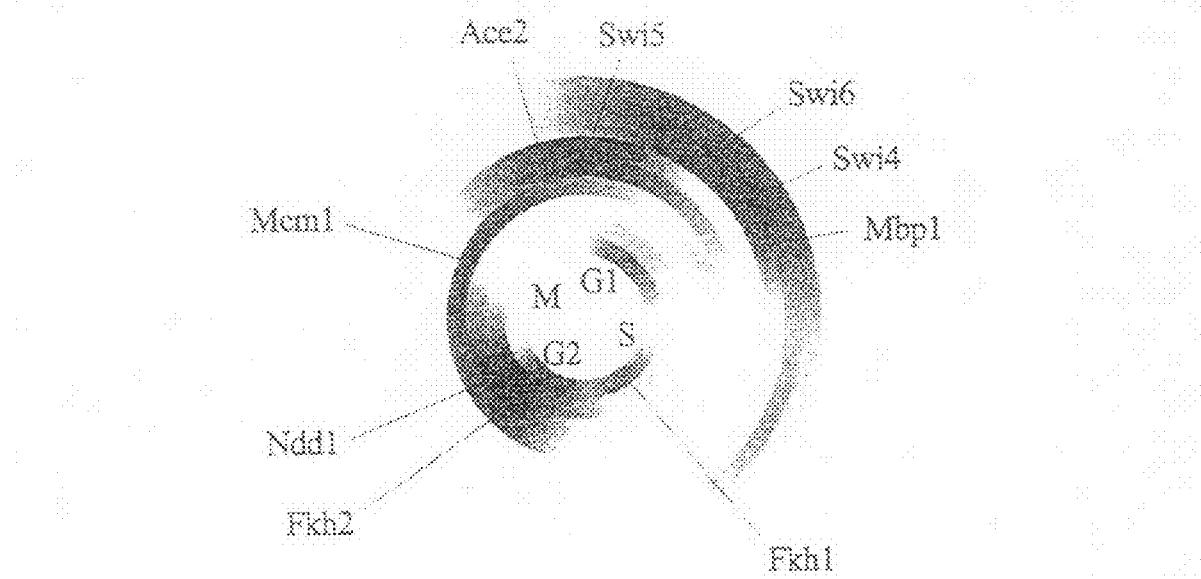

The data described herein also provide novel insights into stage-specific gene regulation by these factors. Previous studies suggested that Fkh1 and Fkh2 are homologs that function in concert with Mcm1 during G2/M (Zhu et al., *Nature*, 406:90-94 (2000)), but it was found that Fkh1 and Fkh2 are also associated with genes expressed in G1 and S, where Mcm1 binding could not be detected (FIGS. 10A-10B). The combination of Mcm1, Fkh2, and Ndd1 bound predominantly to G2/M genes, as expected, but Mcm1 was also bound to genes expressed during M/G1 ($p<10^{-6}$), where binding by Fkh1, Fkh2, or Ndd1 could not be detected. These results indicate that differential regulation of Mcm1 and Fork-head target genes in different stages of the cell cycle are likely governed by the association of these factors with different regulatory partners. Further identification of the genomic binding sites of all yeast transcriptional activators will likely reveal these partners.

Regulation of Transcriptional Regulators

Figure 11A:
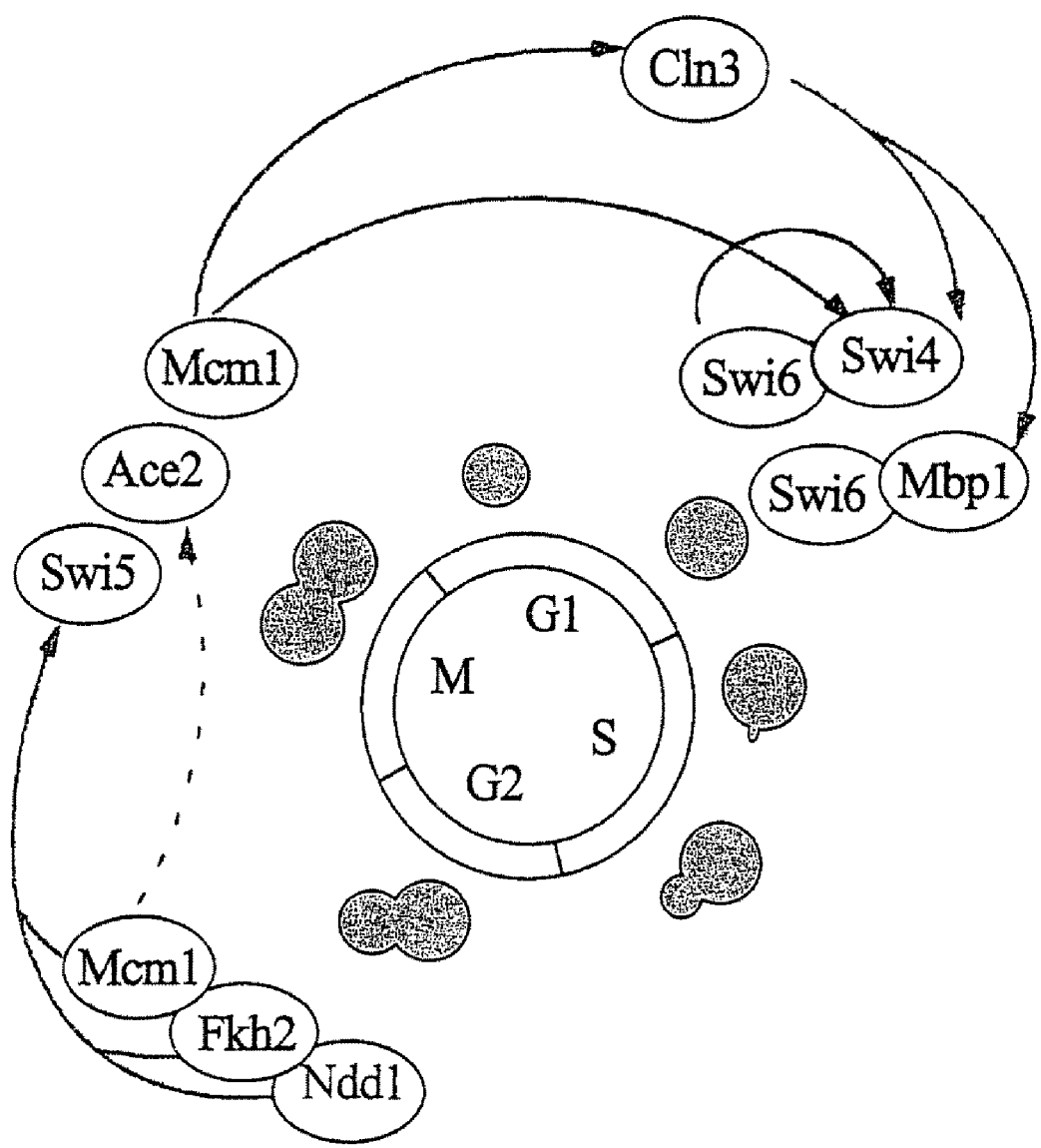
FIGS. 11A-11B are schematics showing transcriptional regulation of cell cycle transcription factor genes.
Figure 11B:
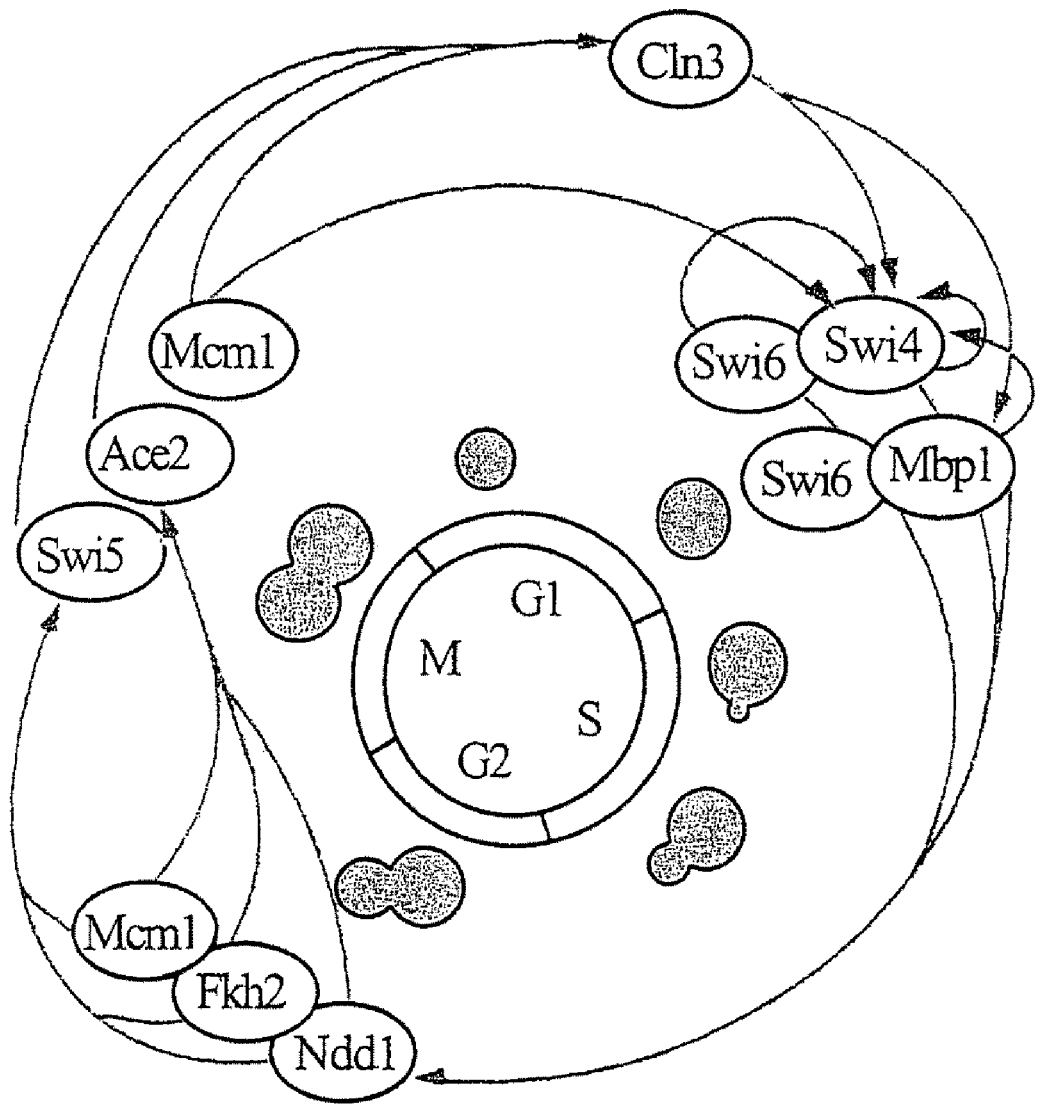

The extent to which the cell cycle transcriptional regulate expression of other regulators was examined. Previous studies established that genes encoding several of the cell cycle transcriptional regulators are themselves bound by other cell cycle regulators (FIG. 11A), SWI4 is regulated by Mcm1 and Swi6 (Foster et al., *Mol. Cell Biol.*, 13:3792-3801 (1993); Mackay et al., *Mol. Cell Biol.*, 21:4140-4148 (2001); McInerny et al. *Genes Dev.*, 11:2177-1288 (1997)), Swi5 is regulated by Mcm1/Fkh2/Ndd1 complex (Koranda et al., *Nature*, 406:94-98 (2000); Kumar et al. *Curr. Biol.*, 10:896-906 (2000); Pic et al., *Embo J.*, 19:3750-3761 (2000); Zhu et al., *Nature*, 406:90-94 (2000)), and expression of ACE2 is affected by depletion of Mcm1 (Althoefer et al., 1995). The genome-wide location data confirmed these results. The location data also revealed that the set of factors that regulates genes during each phase of the cell cycle also regulates expression of one or more activators involved in the next phase of the cell cycle, forming a fully connected regulatory network (FIG. 11B).

The regulatory network from the genomic binding data (FIG. 11B) described herein can be described as follows. SBF (Swi4/Swi6) and MBF (Mbp1/Swi6), which are active during late G1, both regulate NDD1. Ndd1 protein is a limiting component of the complex that activates G2/M genes; Mcm1 and Fkh2 are bound to promoters throughout the cell cycle, and activation of G2/M genes is dependent on recruitment of Ndd1 (Koranda et al. *Nature*, 406:94-98 (2000)). The Mcm1/Fkh2/Ndd1 complex regulates SWI5 and ACE1. Swi5, Ace2, and Mcm1 activate M/G1 genes. Mcm1 binds to the SWI4 promoter and contributes to its activation in M/G1, leading to accumulation of the Swi4 subunit of the SBF transcription factor in G1. All three M/G1 transcription factors regulate CLN3, whose protein product forms a complex with Cdc28, which in turn activates SBF and MBF during late G1 (Dirick et al. *Embo. J*, 14:4803-4813 (1995)). Swi4 transcription is further regulated in late G1 by both SBF and MBF. Thus, the serial regulation of cell cycle regulators occurs throughout the cycle, forming a fully connected regulatory network that is itself a cycle.

Cyclin/CDK Regulation

The transition between stages of the cell cycle is associated with oscillations in the activity of Cdc28-cyclin complexes; cyclin synthesis is necessary for phase entry, and CDK-cyclin inhibition/degradation is necessary for phase exit (Morgan, *Annu. Rev. Cell Biol.*, 13:261-291 (1997)). The G1 and S cyclins Cln1, Cln2, Clb5, and Clb6 accumulate and associate with Cdc28 in late G1, and cyclins Clb1-Clb4 accumulate and associate with Cdc28 in G2 and M (Nasmyth, 1996). These cyclin-CDK complexes can be inhibited by specific cyclin-CDK inhibitors such as Sic1 and Far1 (Mendenhall et al. *Annu. Rev. Cell Biol.*, 13:261-291 (1997)), or can be targeted for degradation by, for example, the anaphase promoting complex (APC) (King et al., *Science*, 274:1652-1659 (1996)).

Figure 12A:
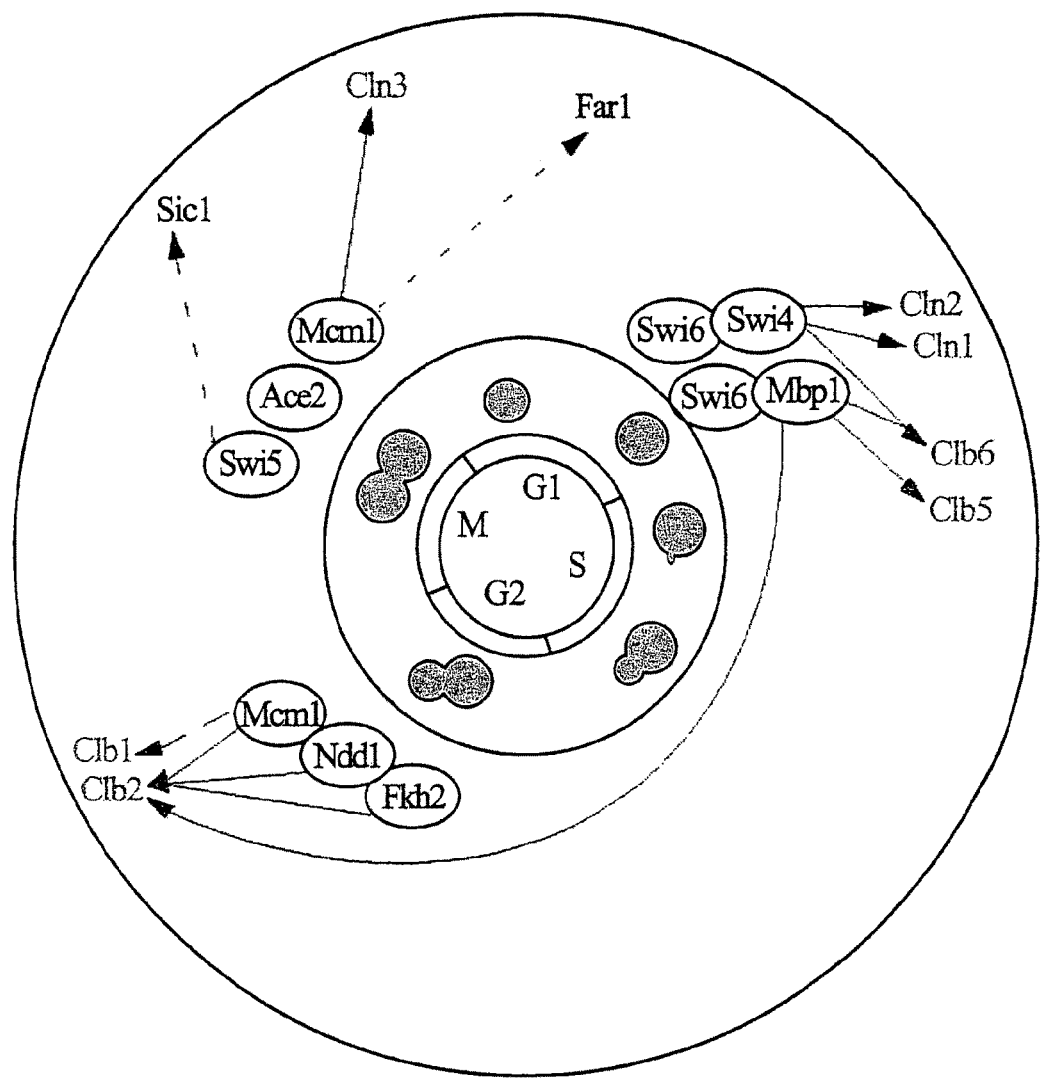
FIGS. 12A-12B are schematics showing transcriptional regulation of cyclin and cyclin/CDK regulator genes.
Figure 12B:
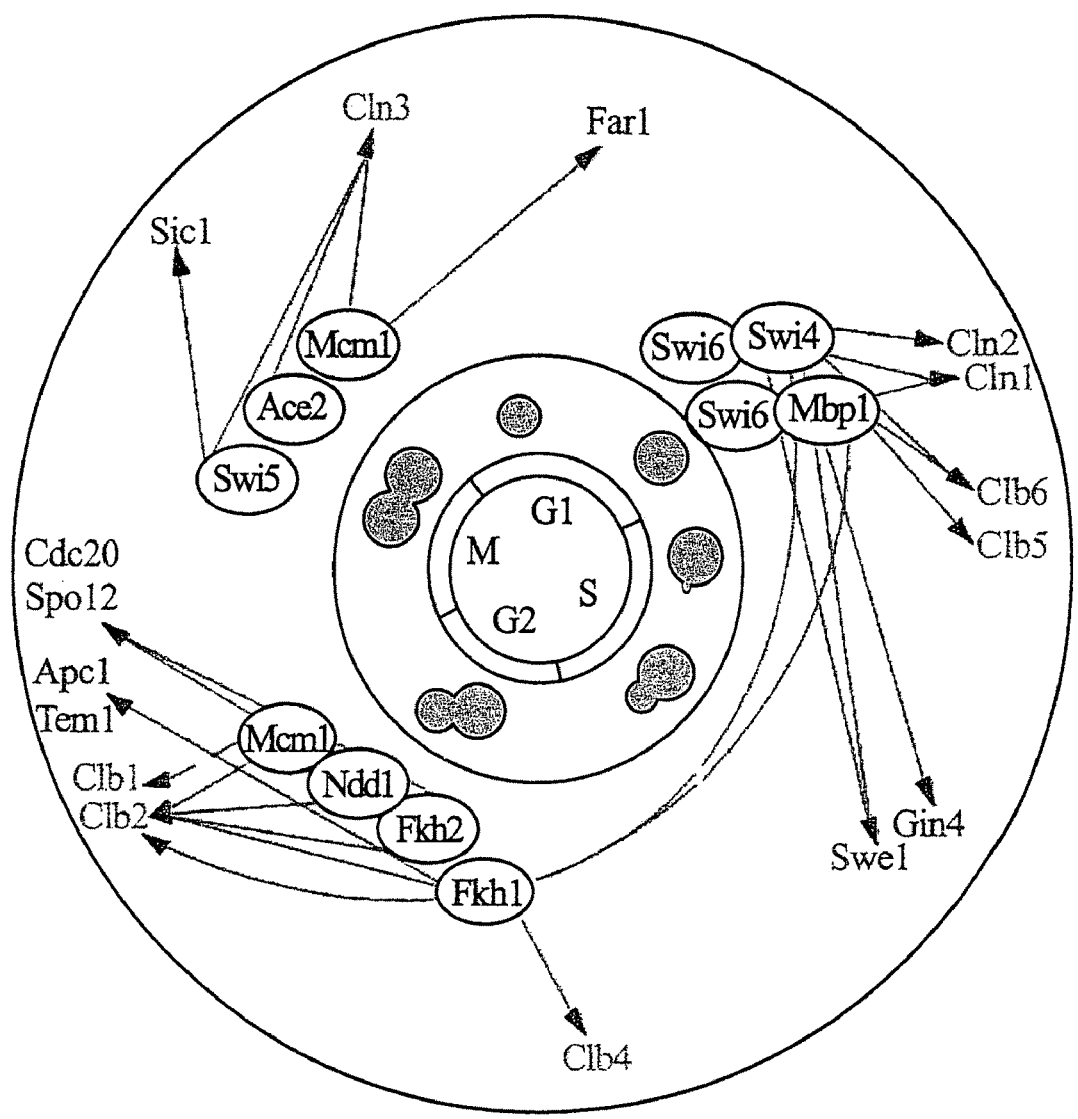

Previous studies identified the transcriptional regulators for most cyclin genes (FIG. 12A). SBF and MBF control transcription of G1 and S cyclin genes (Iyar et al. *Nature*, 409:533-536 (2001); Koch et al., *Curr. Opin. Cell Biol.*, 6:451-459 (1994)). SBF also participates in the regulation of CLB1 and CLB2 (Iyar et al. *Nature*, 409:533-536 (2001)). The Mcm1/Fkh2/Ndd1 complex regulates the CLB2 gene in G2/M (Koranda et al. *Nature*, 406:94-98 (2000); Kumar et al., *Nature*, 406:94-98 (2000); Pic et al. *Embo J.*, 19:3750-3761 (2000); Zhu et al. *Nature*, 406:90-94 (2000)), and Mcm1 regulates transcription of GLN3 in M/G1 (Mackay et al. *Mol. Cell Biol.*, 21:4140-4148 (2001); McInerny et al. *Genes Del.*, 11:1277-1288 (1997)). Our results confirm these observations and reveal that Fkh1 binds the CLB4 promoter. The additional target genes bound by the cell cycle transcriptional regulators described herein reveal that transcriptional regulation is more involved in cell cycle progression than previously reported. Transcription factors that regulate cyclin genes during each phase of the cell cycle also regulate genes encoding key components involved in transitioning to the next stage of the cell cycle (FIG. 12B).

The location analysis indicates that SBF and MBF control transcription of G1/M cyclin genes, but also regulate expression of the G2/M cyclin Clb9, which inhibits further expression of the G1/S cyclins Cin1 and Cin2 (Amon et al. *Cell*, 74:993-1007 (1993)) and promotes entry into mitosis (Surana et al. *Cell*, 65:145-161 (1991)). SBF and MBF also regulate the transcription of the transcription factor Ndd1, which also binds the CLB2 promoter. Thus, SBF, MBF and Ndd1 ultimately collaborate to regulate transcription of the CLB2 gene. SBF and MBF therefore regulate genes necessary for the transition through G1/S, as well as genes whose products set the stage for further progression through the cell cycle.

The data also reveal that the G2/M activators (Mcm1/Fkh2/Ndd1) bind genes whose expression is necessary for both entry into and exit from mitosis. The G2/M activators bind and regulate transcription of CLB2, whose product is necessary to enter mitosis (Surana et al. *Cell*, 65:145-161 (1991)). They also set the stage for exit from mitosis by regulating the gene encoding Cdc20, an activator of the APC, which targets the APC to degrade Pds1 and thus initiate chromosome separation (Visintin et al. *Science*, 278:450-463 (1997)). Cdc20-activated APC also degrades Clb5 (Shirayama et al. *Nature*, 402:203-207 (1999)) and thus enables Cdc14 to promote the transcription and activation of Sic1 (Shirayama et al., *Nature*, 402:203-207 (1999)) and to initiate the degradation of Clb2 (Jaspersen et al., *Mol. Biol. Cell*, 9:2803-2817 (1998); Visintin et al., *Science*, 278:450-463 (1997)). In addition, the G2/M activators Mcm1/Fkh2/Ndd1 regulate transcription of SPO12, which encodes a protein that also regulates mitotic exit (Grether et al., *Mol. Biol. Cell*, 10:3689-2703 (1999)).

The M/G1 transcriptional regulators (Mcm1, Ace2, and Swi5) bind genes that are key to entering and progressing through G1. Swi5 binds to the SIC1 promoter, and all three transcriptional regulators bind to the GLN3 promoter. Sic1 inhibits Clb-Cdc28 during mitosis (Toyn et al. *Genetics*, 145:85-96 (1997)), thus facilitating exit from mitosis. Cln3-Cdc28 activates SBF and MBF in late G1 (Dirick et al. *Embo. J.*, 14:4803-4813 (1995)), thus setting the stage for another cell cycle circuit. In summary, knowledge of the global set of cyclin and CDK regulatory genes that are bound by each of the transcriptional activators provides a much enriched model to explain how transcriptional regulation contributes to cell cycle progression (FIG. 12B).

Regulation of Stage-Specific Functions

Figure 13:
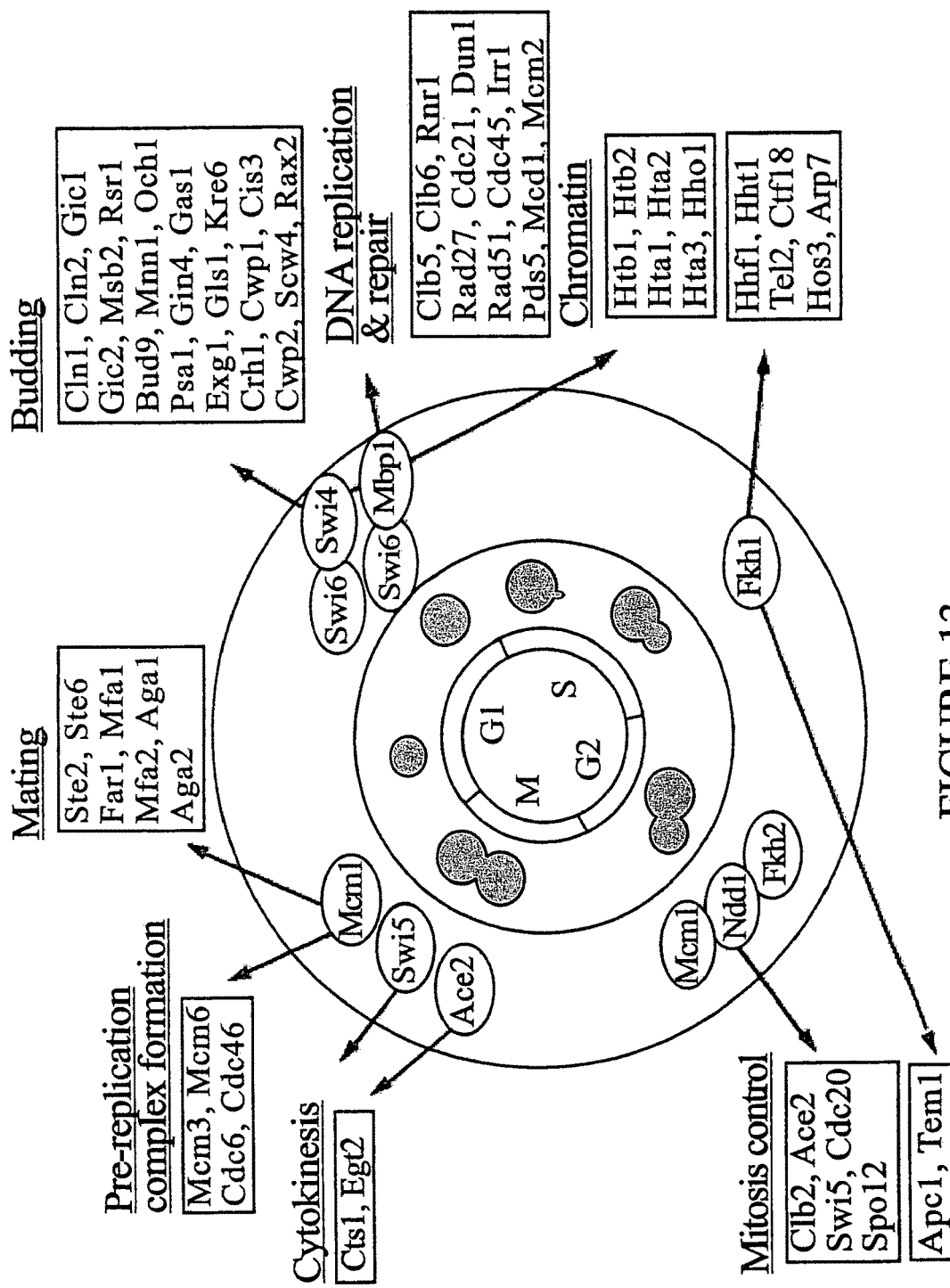
FIG. 13 is a schematic of the regulation of cell cycle functions by the activators. Stage-specific cell cycle functions under the control of specific factors are shown. The budding category include genes involved in budding and in cell wall biogenesis; the DNA replication category includes genes involved in replication, repair, and sister chromatid cohesion; the chromatin category includes genes encoding histones, chromatin modifiers, and telomere length regulators. The identity and functions of genes in each category are listed in Table 3.

The genomic location data revealed how specific factors regulate genes associated with stage-specific cell cycle functions (FIG. 13). SBF regulates genes involved in the morphological changes associated with cell budding, and MBF controls genes involved in DNA replication and repair, confirming a previous study (Iyer et al., *Nature*, 409:533-536 (2001)). SBF is also bound to the promoters of several histone genes (HTA1, HTA2, HTA3, HTB1, HTB2 and HHO1), which makes it likely that SBF contributes to the increase in histone gene transcription observed at S phase. Fkh1 was found to bind various genes that encode proteins associated with chromatin structure and its regulation; these include histones (HHF1 and HHT1), telomere length regulators (TEL2 and CTF18), a shared component of the chromatin remodeling complexes Swi/Snf and RSC (ARP7), and a histone deacetylase (HOS3). The G2/M activators (Mcm1/Fkh2/Ndd1) bind genes that regulate the transition through mitosis (SWI5, ACE2, CLB1, CDC20 and SPO12). Ace2 and Swi5 regulate genes involved in cytokinesis (CTS1 and EGT2), whereas Mcm1 (apparently in absence of Fkh1, Fkh2 and Ndd1) regulates genes encoding proteins involved in prereplication complex formation (MCM3, MCM5/CDC46, MCM6 and CDC6) and in mating (STE2, STE6, FAR1, MFA1, MFA2, AGA1, and AGA2). A summary of binding data for each of the transcriptional regulators is presented in Table 3.

TABLE 3

Selected Targets of the Cell Cycle Activators

| | Gene | SBF | MBF | Fkh1 | Fkh2 | Mcm1/Fkh2/Ndd1 | Mcm1 | Ace2 | Swi5 | Short description |
|---|---|---|---|---|---|---|---|---|---|---|
| Cell Cycle Control | PCL9 | | | | | | | | + | Cyclin that associates with Pho85p |
| | CDC6 | + | + | | | | + | | | Protein that regulates initiation of DNA replication |
| | SIC1 | | | | | | | | + | P40 inhibitor of Cdc28p-Clb protein kinase complex |
| | SWI4 | + | + | | | | + | | | Transcription factor that participates in the SBF complex |
| | PCL2 | + | | | | | | + | + | Cyclin, found partly in association with Pho85p |
| | CLB6 | + | + | | + | | | | | B-type cyclin appeaaring late in G1 |
| | CLB5 | | + | | | | | | | B-type cyclin appeearing late in G1 |
| | SWE1 | + | + | | | | | | | Serine/tyrosine dual-specificity protein kinase |
| | PCL1 | + | + | | + | | + | | | G1/S-Specific cyclin |
| | CLN2 | + | | | | | | | | G1/S-Specific cyclin |
| | CLN1 | + | + | + | + | | | | | G1/S-Specific cyclin |
| | OPY2 | | + | | | | | | | Protein that may be involved in cell-cycle regulation |
| | NDD1 | + | | | | | | | | Protein required for nuclear division |
| | CLB4 | | | + | | | | | | G2/M-phase-specific cyclin |
| | SIM1 | + | | | + | | + | | | Protein involved in the aging process and in cell cycle regulation |
| | PCL7 | | | | | | | | + | Cyclin, associates with Pho85p |
| | HSL7 | | | | + | | | | | Negative regulatory protein of the Swe1p protein kinase |
| | APC1 | | | +/− | | | | | | Component of the anaphase-promoting complex (APC) |
| | ACE2 | | | + | + | + | | | | Metallothionein expression activator with similarity to Swi5p |
| | CLB2 | + | | + | + | + | | | | G2/M-phase-specific cyclin |
| | SWI5 | | | | + | + | | | | Transcription factor that controls cell cycle-specific transcription of HO |
| | HDR1 | | | | + | | | | | Protein involved in meiotic segregation |
| | TEM1 | | | + | + | | | | | GTP-binging protein of the ras superfamily involved in termination of M-phase |
| | CDC20 | | | | + | + | | | | Protein required for microtubule function at mitosis |
| | SPO12 | | + | | + | + | | | | Sporulation protein required for chromosome division in meiosis I |
| | CLN3 | | | | | | + | + | +/− | GI/S-specific cyclin |
| | DBF2 | | | | | | + | | | Serine/threonine protein kinase related to Dbf20p |
| | FAR1 | | | | | | + | | | Inhibitor of Cdc28p-Cln1p and Cdc28p-Cln2p kinase complexes |
| Cell wall biogenesis, budding, and cytokinesis | CSH1 | | | | | | | | + | Chitin synthase I |
| | TEC1 | | | | | | | | + | Transcriptional activator |
| | EGT2 | | | | | | | + | + | Cell-cycle regulation protein, may be involved in cytokinesis |
| | GIC2 | + | + | | | | | | | Putative effector of Cdc42p, important for bud emergence |
| | SWC11 | | | | | | | + | + | Putative cell wall protein |
| | GIN4 | + | | | | | + | | | Serine/threonine-protein kinase |
| | BUD9 | + | | + | | | + | + | + | Protein required for bipolar budding |
| | OCH1 | + | | | | | | | | Alpha-1,6-mannosyltransferase |
| | CTS1 | | | | + | | | + | + | Endochitinase |
| | RSR1 | + | | | | | | | | GTP-binding protein of the ras superfamily involved in bud site selection |
| | CRH1 | + | + | | | | | | + | Protein for which overproduction suppresses bud emergence defects |
| | MSB2 | + | | | | | | | | Cell wall protein |
| | MNN1 | + | | | | | | | | Exo-beta-1,3-glucanase (I/II) |
| | EXG1 | + | + | + | + | | + | | + | Alpha-1,3-mannosyltransferase |
| | GLS1 | + | | | | | | | | Component of beta-1,3-glucan synthase |

TABLE 3-continued

Selected Targets of the Cell Cycle Activators

| | Gene | SBF | MBF | Fkh1 | Fkh2 | Mcm1/Fkh2/Ndd1 | Mcm1 | Ace2 | Swi5 | Short description |
|---|---|---|---|---|---|---|---|---|---|---|
| | GAS1 | + | | | | | | | | Glycophospholipid-anchored surface glycoprotein |
| | PSA1 | + | | | | | | + | | Mannose-1-phosphate guanyltransferase |
| | KRE6 | + | | | | | | | | Glucan synthase subunit required for synthase of beta-1,6-glucan |
| | GIC1 | + | | | + | | | | | Putative effector of Cdc42p, important for bud emergence |
| | CWP1 | + | | | + | | | | | Mannoprotein of the cell wall; member of the PAU1 family |
| | CIS3 | + | | | + | | | | | Cell wall protein |
| | CWP2 | + | + | + | + | | | + | | Protein that controls interaction of bud-neck cytoskeleton with G2 nucleus |
| | BUD4 | | | + | + | + | | | | Protein required for axial budding but not for bipolar budding |
| | WSC4 | | | | | | + | | | Protein required for maintenance of cell wall integrity |
| | BUD8 | | | + | | | | | | Protein required for bipolar budding |
| | SCW4 | + | | | | | | | | Cell wall protein; similar to gulcanases |
| | RAX2 | + | | | + | + | | | | Protein involved in bipolar budding |
| | SKN1 | | | | | | + | | | Glucan synthase subunit |
| DNA replication | RNR1 | + | + | | + | | | | | Ribonucleotide reductase large subunit |
| | RAD27 | | + | | | | | | | Single-stranded DNA endonuclease and 5'-3' exonuclease |
| | CDC21 | | + | | | | | | | Thymidylate synthase, converts dUMP to dTMP |
| | IRR1 | | + | | | | | | | Component of cohesin complex |
| | MCD1 | | + | | | | | | | Cohesin, protein required for mitotic chromatid cohesion |
| | PDS5 | | + | + | + | | | | | Protein required for sister chromatid cohesion |
| | RAD51 | | + | | + | | | | | Protein that stimulates pairing and strand-exchange between homologous |
| | DUN1 | | + | | | | | | | Protein kinase required for induction of DNA repair genes after DNA damage |
| | ALK1 | | | | | | + | | | DNA damage-responsive protein |
| Chromatin | CTF18 | | | + | | | | | | Protein required for maintenance of normal telomere length |
| | HHF1 | | +/− | | | | | | | Histone H4, identical to Hhf2p |
| | HHT1 | | +/− | | | | | | | Histone H3, identical to Hht2p |
| | HTB2 | + | | | | | | | | Histone H2B, nearly identical to Htb1p |
| | HTB1 | + | | | | | | | | Histone H2B |
| | HTA1 | + | | | | | | | | Histone H2A, identical to Hta2p |
| | HTA2 | + | | | | | | | | Histone H2A, identical to Hta1p |
| | HHO1 | + | | | | | | | | Histone H1 |
| | TEL2 | | | + | | | | | | Protein involved in controlling telomere length and telomerre position effect |
| | ARP7 | | | + | | | | | | Component of SWI-SNF and RSC chromatin remodeling complex |
| | HTA3 | + | | | | | | | | Histone-related protein that can suppress histone H4 point mutation |
| | HOS3 | | | + | | | | | | Protein with similiarity to Hda1p, Rpd3p, Hos2p, and Hos1p |
| Prereplication complex | MCM3 | | | | | | + | | | Protein that acts at ARS elements to initiate replication |
| | CDC6 | + | + | | | | + | | | Protein that regulates initiation of DNA replication |
| | CDC46 | | | | | | + | | | Protein that acts at ARS elements to initiate replication |
| | CDC45 | + | | | | | | | | Protein required for initiation of chromosomal DNA replication |
| | MCM2 | + | | | | | | | | Protein that acts at ARS elements to initiate replication |
| | MCM6 | | | | | | + | | | Protein involved in DNA replication; member of the MCM/P1 family of proteins |

TABLE 3-continued

Selected Targets of the Cell Cycle Activators

| | Gene | SBF | MBF | Fkh1 | Fkh2 | Mcm1/Fkh2/Ndd1 | Mcm1 | Ace2 | Swi5 | Short description |
|---|---|---|---|---|---|---|---|---|---|---|
| Mating | ASH1 | | | | | | | | + | GATA-type transcription factor, negative regulator of HO expression |
| | AGA2 | | | | | | + | | | a-Agglutinin binding subunit |
| | AGA1 | + | + | | | | + | | | a-Agglutinin anchor subunit |
| | HO | + | | | | | | | | Homothallic switching endonuclease |
| | MFA1 | | | | | | + | | | Mating pheromone a-factor; exported from cell by Ste6p |
| | MFA2 | | | | | | + | | | Mating pheromone a-factor; exported from cell by Ste6p |
| | STE6 | | | | | | + | | | Membrane transporter responsible for export of "a" factor mating pheromone |
| | STE2 | | | | | | + | | | Pheromone alpha-factor receptor; has seven transmembrane segments |
| | FAR1 | | | | | | + | | | Inhibitor of Cdc28p-Cln1p and Cdc28p-Cln2p kinase complexes |

A partial list of cell cycle genes whose promoter regions were bound by the indicated cell cycle regulators.
+ indicates binding with P < 0.001,
+/− indicates binding with P < 0.0015.
A full list of target genes is available at the author's web site (http://web.wi.mit.edu/young/cellcycle). The DNA replication category includes genes that function in DNA synthesis, in DNA repair and in sister chromatid cohesion.

Functional Redundancy

The factor location data demonstrate that each of the nine cell cycle transcription factors binds to critical cell cycle genes, yet cells with a single deletion of MBP1, SWI4, SWI6, FKH1, FKH2, ACE2, or SWI5 are viable; only MCM1 and NDD1 are essential for yeast cell survival (Breeden *Curr. Biol.*, 10:R586-R588 (2000); Loy et al. *Mol. Cell Biol.*, 19:3312-3327 (1999); Mendenhall et al., *Mol. Biol. Rev.*, 62:1191-1243 (1998)). The conventional explanation for this observation is that each nonessential gene product shares its function with another. Swi4 and Mbp1 share 50% identity in their DNA binding domains (Koch et al. *Science*, 261.1551-1557 (1993)). Similarly, Fkh1 and Fkh2 are 72% identical (Kumar et al. *Curr. Biol.*, 10:896-906 (2000)), and Swi5 and Ace2 are 83% identical in their respective DNA binding domains (McBride et al. *J. Biol. Chem.*, 274:21029-21036 (1999)). Each of these pairs of proteins recognizes similar DNA motifs, so it is likely that functional redundancy rescues cells with mutations in individual factors. However, it was not clear whether each of the pairs of factors had truly redundant functions in normal cells, or whether they exhibit redundant function only in mutant cells that lack the other factor.

The data described herein demonstrates that each of the cell cycle factor pairs discussed above does bind overlapping sets of genes in wild-type cells, revealing that the two members of each of the pairs are partially redundant in normal cell populations (FIGS. 14A-14B). Mbp1 and Swi4 share 34% of their target genes, Fkh1 and Fkh2 share 22%, and Ace2 and Swi5 share 25%. It is also clear, however, that this redundancy does not apply to all genes regulated by a pair of related activators in wild-type cells. The partial overlap in genes under the control of pairs of regulators explains why one gene of a pair can rescue defects in the other, yet each member of the pair can be responsible for distinct functions in wild-type cells.

Discussion

Identification of the transcriptional regulatory network that controls the cell cycle clock is essential to fully understand how cell cycle control is effected. As described herein, the genomic targets of each of the nine known yeast cell cycle regulators have now been identified using a combination of genome-wide location and expression analysis. The investigation revealed that a connected, circular transcriptional regulatory network has evolved to control the cell cycle, and showed how each of the transcriptional regulators contributes to diverse stage-specific functions Cell Cycle Transcriptional Regulatory Networks A key concept that emerged from this study is that cell cycle transcriptional control is effected by a connected regulatory network of transcriptional activators. The cell cycle transcriptional regulators that function during one stage of the cell cycle regulate the transcriptional regulators that function during the next stage, and this serial regulation of transcriptional regulators forms a complete regulatory circuit. Thus, the transcriptional regulatory network that controls the cell cycle is itself a cycle of regulators regulating regulators. The discovery of this connected transcriptional regulatory network is important for several reasons. It provides additional understanding of the regulatory mechanism by which cells ensure transitions from one stage into the appropriate next stage. It supplies the foundation for future work on the mechanisms that coordinate gene expression and other aspects of cell cycle regulation. Furthermore, it suggest that a connected, circular transcriptional regulatory network is likely a fundamental feature of cell cycle regulation in other, more complex, organisms.

It is interesting to consider why cells have pairs of cell cycle transcriptional regulators with partially redundant functions. This configuration may help ensure that the cell cycle is completed efficiently, which is critical since the inability to complete the cycle leads to death. At the same time, devoting each of the pair to distinct functional groups of genes enables coordinate regulation of those functions. It is also likely that partial redundancy helps the cell to make a smoother temporal transition from one mode of operation to another during the cell cycle.

The results described herein identify how the cyclin genes regulated by the nine transcriptional activators. In addition, the results reveal that transcription factors that regulate the cyclin genes during each phase of the cell cycle also regulate genes that are involved in transitioning to the next stage of the cycle (FIGS. 12A-12B). For example, the G1/S activators SBF and MBF control transcription of G1/S cyclin genes, but also regulate expression of G2/M cyclin Clb2, which subsequently inhibits further expression of the G1/S cyclins Cin1 and Cin2 and promotes entry into mitosis. Thus, the cell cycle transcriptional regulatory network has evolved so that some transcriptional regulators contribute to the control of both stage entry and exit.

The identification of sets of genes that are bound by each of these regulators reveals how coordinate regulation of a wide variety of stage-specific cell cycle functions is regulated (FIG. 13). For example, the G1/S activators regulate genes involved in cell budding, DNA replication and repair, and chromosome maintenance. The G2/M activators bind genes that regulate transition through mitosis. The late M factors regulate genes involved in cytokinesis and prereplication complex formation.

Figure 3:
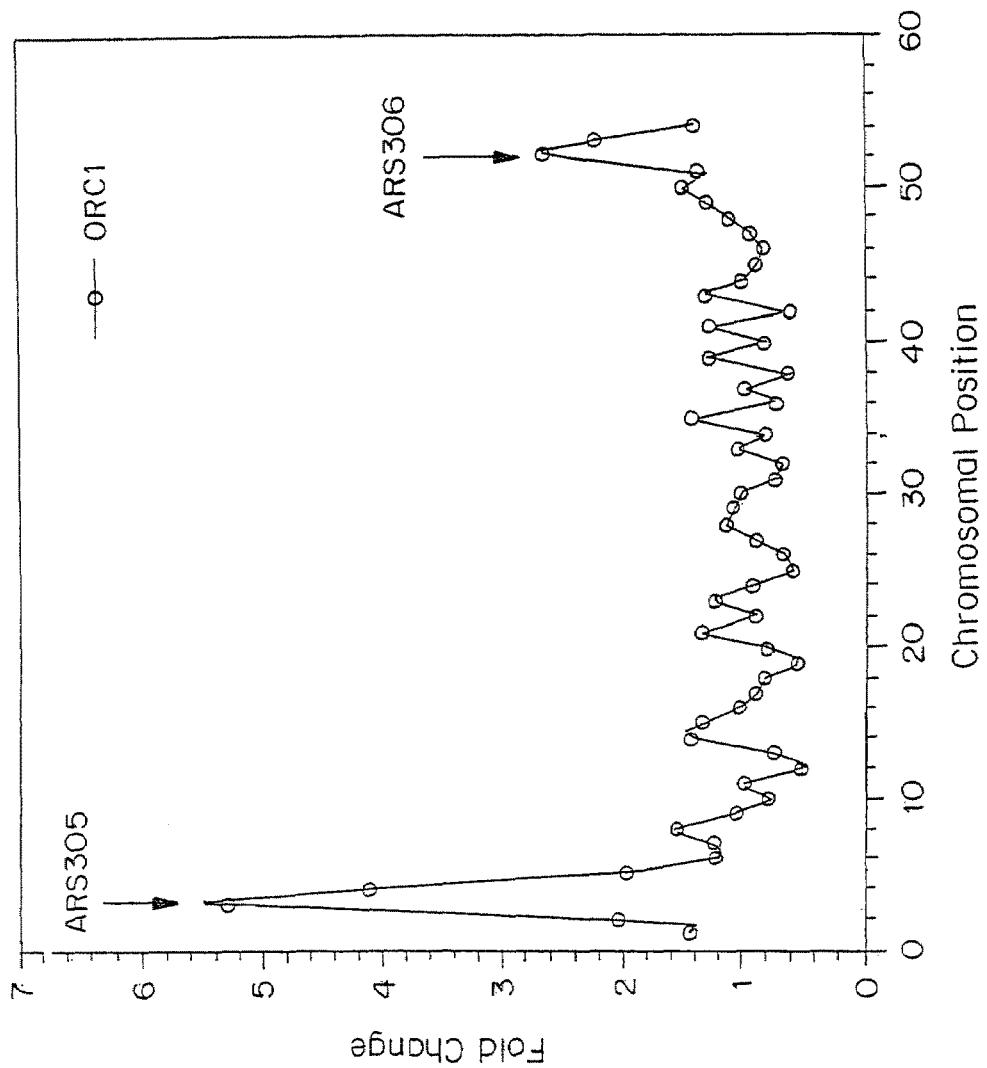
FIG. 3 is a graph of chromosomal position versus fold change of Genome-wide Monitoring Protein-DNA interactions.
Figure 4:
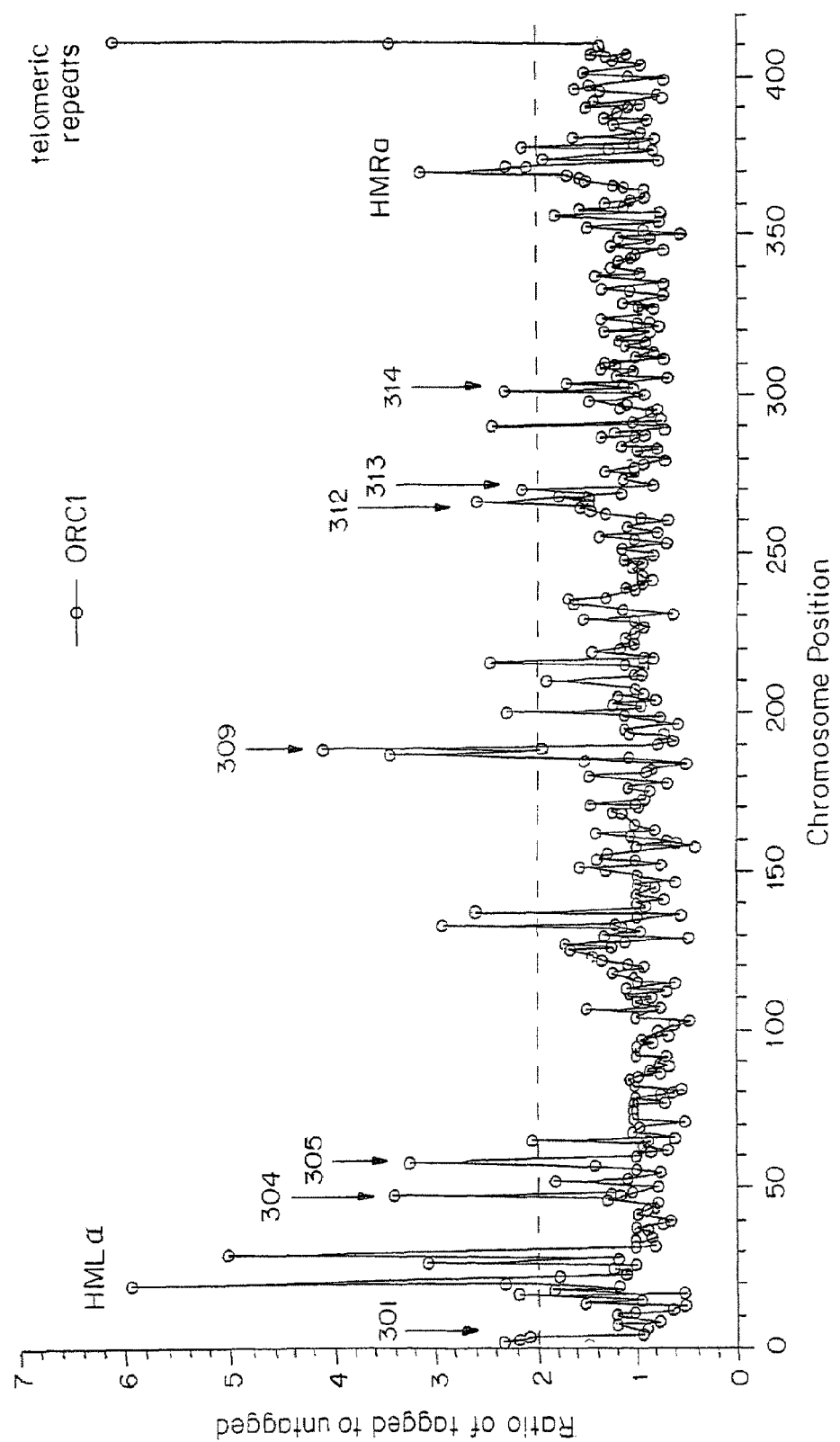
FIG. 4 is a graph of chromosome position versus ratio of tagged to untagged for binding of ORC1 to yeast chromosome III.

A more comprehensive picture of cell cycle regulation emerges when existing knowledge of cell cycle regulatory mechanisms is combined with the new information on the transcriptional regulatory network. Several key features of this integrated view have important implications for cell cycle regulation. Cells commit to a new cell cycle at START, but only after cell growth is sufficient to ensure completion of the cycle, since the inability to complete the cell cycle can be lethal (Mendenhall et al., *Mol. Biol. Rev.*, 62:1191-1243 (1998)). The emphasis on regulation at the G1/S boundary is evident from the regulatory events involving Swi4 in the model shown in FIG. 3B. The Swi4 regulator becomes functionally active at START, via a mechanism that is dependent on Cln3-Cdc28, when the cell reaches a critical size (Dirick et al., *Embo. J.*, 14:4803-4813 (1995)). The SWI4 promoter is bound by Swi4 itself, indicating that a positive feedback loop exists to ensure that adequate levels of Swi4, and thus, SBF, are present prior to commitment. The observation that the G1/S regulators SBF and MBF both regulate NDD1 suggests how adequate levels of Ndd1 are produced to initiate the G2/M transcriptional program. Ndd1 protein is a limiting component of the complex that activates G2/M genes; Mcm1 and Fkh2 are bound to promoters throughout the cell cycle, and activation of G2/M genes is dependent on recruitment of Ndd1 (Koranda et al., *Nature*, 406:94-98 (2000). The Mcm1/Fkh2/Ndd1 complex regulates SWI5 and ACE2, whose products become functional only in late anaphase after relocalization to the nucleus in a mechanism that is dependent on low Clb-Cdc28 activity (Nasmyth et al., *Cell*, 62:631-647 (1990); Shirayama et al., *Nature*, 402:203-207 (1999)). Later in the cell cycle, the Swi5, Ace2, and Mcm1 factors all bind to the CLN3 promoter, thus assuring adequate levels of the Cln3 cyclin at START.

The cell cycle transcriptional regulatory network model accounts for several observations relevant to cell cycle regulation. The use of multiple transcription factors to regulate key transcription and cyclin regulators explains why mutations in single transcription factors generally have only limited effects on progression through the cell cycle, whereas mutations in activator pairs can have substantial effects (Breedon, *Curr. Biol.*, 10:R586-R588 (2000); Koch, et al., *Science*, 261:1551-1557 (1993); Mendenhall et al., *Mol. Biol. Rev.*, 62:1191-1243 (1998)). Nutrient limitation causes yeast cells to arrest cell cycle progression, but rather than counting a at the time of nutrient limitation, the arrest is delayed until the cells reach G1 (Mendenhall et al., *Mol. Biol. Rev.*, 62:1191-1243 (1998)). Cells that have entered the cell cycle at START may progress through an entire cycle because of the design of the connected transcriptional regulatory network (FIG. 11B), and perhaps then arrest in G1 because of the requirement for adequate levels of Cln3/Cdc28. Several cell cycle checkpoint controls are mediated by regulation of Cdc28 activity (Mendenhall et al., *Mol. Biol. Rev*, 62:1191-1243 (1998)), but how Cdc28 activity affects the transcription program is not well understood. Since the activity of several of the cell cycle transcriptional regulators is dependent on Cdc28 activity, some checkpoint controls may effect arrest by perturbing the connected transcriptional regulatory circuit.

Importance of Direct Binding Information

An impetus for the development of methods that identify the genomic binding sites of factors in vivo was the realization that regulatory networks cannot be accurately deduced from global expression profiles because it is not possible to discriminate between direct and indirect effects due to genetic or other perturbations in living cells (Ren et al., *Science*, 290:2306-2309 (2000)). A further challenge for understanding global gene regulation is that comparison of wild-type and mutant expression profiles produce valuable information on dependencies when the mutant gene is essential, but it is more difficult to interpret such information when the mutant gene can be rescued by functionally redundant gene products. It was found herein that the direct binding data obtained in the present study was remarkably confirming of previous evidence for gene regulation by specific transcription factors when that evidence was direct. In contrast, evidence in support of many studies in which the involvement of a factor in the regulation of a gene was deduced from indirect evidence was not obtained (Althoefer et al., *Mol. Cell Biol.*, 15.5917-5928 (1998); Gordon, et al., *Proc. Natl. Acad. Sci., USA*, 88:6058-6062 (1991); Koch, et al., *Science*, 261:1551-1557 (1993); Lowndes et al. *Nature*, 350:247-250 (1991); Platt et al., *Embo J.*, 14:3788-3799 (1995). Pizzagalli et al., *Proc. Natl. Acad. Sci., USA*, 85:3772-3776 (1988); Toone et al. (1995); Verma et al., *Proc. Natl. Acad. Sci., USA*, 88:7155-7158 (1991)).

The identification of the set of promoters bound in vivo by each of the cell cycle regulators allowed identification of consensus sequence motifs (see http://web.wi.mit.edu/young/cellcycle). Two general insights emerged from this analysis. First the binding motifs identified for some factors are found in most, but not all, of the promoters that they bind, indicating that variations of the consensus sequence exist that are not easily recognized by search algorithms or that the transcription factor is modified or associated with binding partners that generate a new binding preference at some genes. In this context, it is interesting that the Mcm1 binding motif is somewhat different in the promoters of its G2/M targets than in its M/G1 targets, probably reflecting the influence of its binding partners. Second, the presence of the DNA binding motif in genomic DNA is not by itself a predictor of protein binding in vivo, as the predicted motifs are found at many sites in the genome other than those bound in vivo. There is, therefore, a need for empirical binding data such as that described here in order to accurately identify genuine binding sites.

Discovering Genetic Regulatory Networks

Understanding how biological processes are regulated on a genomic scale is a fundamental problem for the coming decades. Maps of metabolic pathways have been key to studying basic biology, uncovering disease mechanisms, and discovering new drugs over the last century. Maps of genomic regulatory networks will play an equally important role in future biological discovery.

The location data presented herein are well adapted to new computational approaches to discovering genetic regulatory networks. The binding of a transcriptional activator to the promoter region of a gene indicates that the activator has a regulatory effect on the gene. However, it is also possible that the activator does not fully or even partially control the gene. Thus, location information must be fused with other data, such as expression data, to fully elaborate the complete mechanism of transcriptional regulation and the form of regulatory networks. New computational approaches will synergistically combine location data with other data types to form a well-focused picture of cellular function. For example, one way to combine location and expression data is to use the location data to first suggest tentative factor-target pairs with associated p-values. These factor-target pairs represent constraints on the possible genetic regulatory network models, and they can be used to guide the search of network models based on expression data. This process can discover alternative models of regulatory networks, with a principled measure of likelihood assigned to each hypothesis. The likelihood measure appropriately reflects how consistent the hypothesis is with both location and expression data. This likelihood-based approach can accommodate location data, expression data, and other forms of data (Ross-MacDonald, et al., *Nature*, 402.413-418 (1999); Uetz, et al., *Nature*, 403:623-627 (2000)) that can be usefully employed to assign probabilities to potential interaction.

Example 4

Study Design for Serial Regulation of Transcriptional Regulators

Serial Regulation of Transcriptional Regulators

Study Design
  Genetic Reagents
    Oligo Table
    Strain List
  Technology
  Location Analysis Protocols
  Analysis Location Analysis
  Quality Control
  Search for Activator Binding Sites
  Download Datasets
  Table of Regulated Genes
  Previous Evidence of Regulation Gene Expression Data
  Alpha Factor Synchronization Insights
  Cell Cycle Regulation
  Additional Insights
  Summary Genetic Reagents The cell cycle activators Swi4, Mbp1, Swi6, Fkh1, Fkh2, Ndd1, Mcm1 and Ace2 were tagged with a 9 or 18 copy myc epitope by inserting its coding sequence into the normal chromosomal loci of these genes. Vectors developed by K Nasmyth (Cosma et al., 1999) was used for recombination of the epitope coding sequence into the W303 strain Z1256. The specific oligonucleotides used to generate PCR products are described here. The PCR products were transformed into the strain Z1256 to generate the tagged strains. Clones were selected for growth on TRP-plates, and the insertion was confirmed by PCR and expression of the epitope-tagged protein was confirmed by western blotting using an anti-Myc antibody (9E11). A 9 myc tagged version of Swi5 (Z1407) was obtained from K Nasmyth.

Protocols—Location Analysis

The chromatin immunoprecipitation part of that protocol is based on a protocol obtained from the Nasmyth lab and one from Hecht, A., Strahl-Bolsinger, S., and Grunstein, M. "Spreading of transcriptional repressor SIR3 from telomeric heterochromatin," *Nature* 383, 92-6 (1996). The Nasmyth protocol was optimized for use with W303α strains tagged with a Myc18 epitope inserted at the C-terminus of various transcription factors (strains obtained from Pia Cosma).

Microarray Production
  Location Analysis Protocols
    Preparation of cells, cross linking, cell washing and storing
    Cell lysis, sonication, and immunoprecipitation
    Bead washing, elution from beads and reversal of cross linking
    DNA precipitation
    Blunting DNA and ligation of blunt DNA to linker
    Ligation-mediated PCR
    Pre-hybridization, probe preparation, hybridization and wash
    Appendices:
      Preparation of magnetic beads
      Preparation of unidirectional linker
      Solutions Oligo List

| Strain | Gene | Tag | Forward primer | Backward primer |
|---|---|---|---|---|
| Z1372 | MBP1 | 18 myc | ATAAGGGCGCAGAACAGATCATCACAATCT CAAACGCGAATAGTCATGCAtccggttctgctgctag | CTATTTTTCAGTATATGGATACATGTAAAGT TCCTCTATTTATGTATATTcctcgaggccagaagac |
| Z1335 | SWI4 | 18 myc | ACATTGACTCAAAATTGGACGATATAGAAA AGGATTTGAGGGCAAACGCAtccggttctgctgctag | AAAAACTCTGATAATATAGTAAAAATTATTG GTACATTGTGAATTAAAATcctcgaggccagaagac |
| Z1373 | SWI6 | 18 myc | AAGACATTGACACTGACGAAATGCAAGATT TTTTAAAAAAGCATGCTTCAtccggttctgctgctag | AATAACTTCAAATAAAGTCATAAAAGTTAAT GCAATGAAATCACATGCCCcctcgaggccagaagac |
| Z1448 | FKH1 | 9 myc | CATCCATGGACGTAACAACAAACGCAAACG TGAACAATTCCTCTCTGAGTtccggttctgctgctag | CTTTGTTCTTTATTGTTTAATAATACATATGG GTTCGACGACGCTGAATTcctcgaggccagaagac |

-continued

Oligo List

| Strain | Gene | Tag | Forward primer | Backward primer |
|---|---|---|---|---|
| Z1370 | FKH2 | 18 myc | AGGAACTAATACTAGATACGGATGGTGCAA AGATCAGTATTATCAACAACtccggttctgctgctag | CCATTTCTCATTCATTTCTTTAGTCTTAGTGA TTCACCTTGTTTCTTGTCcctcgaggccagaagac |
| Z1369 | NDD1 | 18 myc | CAAGGAAAAGCTGTAATTCTAAATCTAATG GAAATTTATTCAATTCACAGtccggttctgctgctag | GCTTGAAATTTCGATTAAAAAAAAAAGGTGA GATGCAAGTTTGGTTAATAcctcgaggccagaagac |
| Z1321 | MCM1 | 18 myc | AGAATGCTGCCTACCAACAATACTTTCAAG AACCGCAACAAGGCCAATACtccggttctgctgctag | CTTTTTCCTCTTAATGCTCGTCTATGAATTAT ATACGGAAATCGATAAGAcctcgaggccagaagac |
| Z1371 | ACE2 | 18 myc | CGCACGAGCAAAACTCGAACCGCACCCTTT CAAACGAAACTGATGCTCTCtccggttctgctgctag | TATTGTTACTATTATTTATTATGTTAATATCATGC ATAGATAAATGTTCGcctcgaggccagaagac |

| GENE | SEQ ID NO. Forward Primer | SEQ ID NO. Reverse Primer |
|---|---|---|
| MBP1 | 13 | 14 |
| SWI4 | 15 | 16 |
| SWI6 | 17 | 18 |
| FKH1 | 19 | 20 |
| FKH2 | 21 | 22 |
| NDD1 | 23 | 24 |
| MCM1 | 25 | 26 |
| ACE2 | 27 | 28 |

Strain List

| Strain | Genotype |
|---|---|
| Z1256 | MATa, ade2-1, trp1-1, can1-100, leu2-3,112, his3-11,15, ura3, GAL+, psi+ |
| Z1372 | MATa, ade2-1, trp1-1, can1-100, leu2-3,112, his3-11,15, ura3, GAL+, psi+, MBP1::18-Myc-MBP1 |
| Z1335 | MATa, ade2-1, trp1-1, can1-100, leu2-3,112, his3-11,15, ura3, GAL+, psi+, SWI4::18-Myc-SWI4 |
| Z1373 | MATa, ade2-1, trp1-1, can1-100, leu2-3,112, his3-11,15, ura3, GAL+, psi+, SWI6::18-Myc-SWI6 |
| Z1448 | MATa, ade2-1, trp1-1, can1-100, leu2-3,112, his3-11,15, ura3, GAL+, psi+, FKH1::9-Myc-FKH1 |
| Z1370 | MATa, ade2-1, trp1-1, can1-100, leu2-3,112, his3-11,15, ura3, GAL+, psi+, FKH2::18-Myc-FKH2 |
| Z1369 | MATa, ade2-1, trp1-1, can1-100, leu2-3,112, his3-11,15, ura3, GAL+, psi+, NDD1::18-Myc-NDD1 |
| Z1321 | MATa, ade2-1, trp1-1, can1-100, leu2-3,112, his3-11,15, ura3, GAL+, psi+, MCM1::18-Myc-MCM1 |
| Z1371 | MATa, ade2-1, trp1-1, can1-100, leu2-3,112, his3-11,15, ura3, GAL+, psi+, ACE2::18-Myc-ACE2 |
| Z1407 | MATa, ade2-1, trp1-1, can1-100, leu2-3,112, his3-11,15, ura3, GAL+, psi+, SWI5::9-Myc-SWI5 |

Technology—Location Analysis

The genome-wide location analysis method we have developed (Ren et al., 2000) allows protein-DNA interactions to be monitored across the entire yeast genome. The method combines a modified Chromatin Immunoprecipitation (ChIP) procedure, which has been previously used to study in vivo protein-DNA interactions at one or a small number of specific DNA sites (Aparicio, O. M., in Current Protocols in Molecular Biology. F. M. Ausubel, et al., Eds. (John Wiley and Sons, Inc., New York, 1999) pp. 21.3.1-21.3.12; Orlando V., "Mapping chromosomal proteins in vivo by formaldehyde-crosslinked-chromatin immunoprecipitation," Trends Biochem Sci 25, 99-104 (2000)), with DNA microarray analysis. Briefly, cells are fixed with formaldehyde, harvested by sonication, and DNA fragments that are crosslinked to a protein of interest are enriched by immunoprecipitation with a specific antibody. After reversal of the crosslinking, the enriched DNA is amplified and labeled with a fluorescent dye using ligation-mediated PCR (LM-PCR). A sample of DNA that has not been enriched by immunoprecipitation is subjected to LM-PCR in the presence of a different fluorophore, and both IP-enriched and unenriched pools of labeled-DNA are hybridized to a single DNA microarray containing all yeast intergenic sequences. The IP-enriched/unenriched ratio of fluorescence intensity obtained from three independent experiments and a p-value is assign to each spot according to an error model adapted from Roberts, C. J., et al., "Signaling and circuitry of multiple MAPK pathways revealed by a matrix of global gene expression profiles," Science 287, 873-80 (2000). The average ratio is then calculated using a weighted average analysis method, providing the relative binding of the protein of interest to each sequence represented on the array.

Microarray Design

Yeast Intergenic DNA Array. Using the Yeast Intergenic Region Primer set (Research Genetics) we PCR amplified and printed 6361 spots, representing essentially all of the known intergenic regions in the yeast genome. The average size of the spotted PCR products was 480 bp, and the sizes ranged from 60 bp to 1500 bp.

Yeast cells expressing an epitope-tagged protein of interest were used; a Myc-epitope coding sequence was integrated into the genome at the 3'-end of the coding sequence for each protein. Cultures of yeast cells were grown to OD600 of 0.8 under appropriate conditions prior to formaldehyde crosslinking. DNA amplification and labeling with LM-PCR was found to produce more reproducible results relative to amplification of enriched DNA as a library in E. coli. Superior and more reproducible results were also obtained when DNA preparations enriched by ChIP were compared to unenriched DNA preparations (rather than DNA preparations obtained from an untagged strain subjected to ChIP).

Microarray Production

The 6361 intergenic regions were amplified using the Yeast Intergenic Region Primers (Research Genetics) primer set. 50 µL PCR reactions were performed in 96-well plates with each primer pair with the following conditions: 0.25 µM of each primer, 20 ng of yeast genomic DNA, 250 µM of each dNTP, 2 mM MgCl2, 1×PCR buffer (Perkin Elmer), and 0.875 units of Taq DNA polymerase (Perkin Elmer). PCR amplification was performed in MJ Research Thermocyclers beginning with 2 minute denaturation at 95° C., followed by 36 cycles of 30 seconds at 92° C., 45 seconds at 52° C., and 2 minutes at 72° C. with a final extension cycle of 7 minutes at 72° C. 1 µL of each PCR reaction mix was then reamplified in a 100 µL PCR reaction using universal primers (Life Technologies) with the same reagent concentrations and the following thermocycling conditions: 3 minutes at 94° C., followed by 25 cycles of 30 seconds at 94° C., 30 seconds at 60° C., and 1 minute at 72° C., with a final extension cycle of 7 minutes at 72° C. Each PCR product was verified by gel electrophoresis. The PCR products were then isopropanol precipitated, washed with 70% ethanol, dried overnight, and resuspended in 20 µL of 3×SSC. The resuspended DNA was transferred to 384 well plates and printed on GAPS-coated slides (Corning) using a Cartesian robot (Cartesian Technologies). The printed slides were rehydrated, snap-dried, and UV crosslinked in UV Stratalinker (Stratagene) set at 60 mJoules. The slides were then stored under vacuum for at least 2 days prior to hybridization.

Preparation of Cells, Cross Linking, Cell Washing and Storing

Step 1—Preparation of Cells and Cross Linking

Inoculate fresh media from an overnight culture to OD600=0.1 and allow yeast to grow to OD600=0.6-1.0 (OD600=0.8 is commonly used).

The experiments are usually done in triplicate, which means you need to put up 3 overnight cultures (inoculated with 3 independent colonies from the same plate).

Remove 50 ml cells and add to 50 ml Falcon tubes (cat #352070) containing 1.4 ml of Formaldehyde (37% Formaldehyde stock, final concentration 1%, J. T. Baker cat. #2106-01).

Use the liquid dispenser for the formaldehyde and work in a fume hood.

Incubate for 20 minutes at room temperature on a rotating wheel.

For some proteins, you may have to optimize the incubation time with formaldehyde.

Transfer to 4° C. and incubate overnight on a rotating wheel.

Step 1a—Preparation of Beads

If you are planning to continue with the protocol the next day, you also need to incubate the magnetic beads with the anti-Myc antibody overnight.

***********Next Steps should be Done at 4° C.***********

Step 1b—Washing and Storage of Cells

Spin 50 ml Falcon tubes for 5 minutes at speed 6 (~2800 rpm) in a tabletop centrifuge (Sorvall RT6000) to harvest the cells and pour off the supernatant.

Wash 3 times with ~40 ml cold TBS.

Add TBS, mix by inversion until the cells are resuspended, spin and pour off the supernatant.

After the last wash, resuspend the yeast pellet using any remaining liquid (add some, if necessary) and transfer to an Eppendorf tube.

Spin for 1 minute at maximum speed at 4° C. and remove the remaining supernatant using a P-1000 pipette.

Snap freeze in liquid nitrogen and store at −80° C., or go directly to step 2.

Cell Lysis, Sonication, and Immunoprecipitation

Step 2—Cell Lysis

Thaw cell pellet on ice.

Resuspend in 700 µl lysis buffer and transfer to a 1.5 ml Eppendorf tube (cat #2236320-4).

Add the equivalent of a 0.5 ml PCR tube (USA/Scientific Cat. #1405-4400) of glass beads (425-600 µµm, Sigma Cat. #G-8772).

Vibrax-VXR at maximum power for 2 hours at 4° C.

Pierce the bottom of the tube with a needle (Use Becton Dickinson Precision Glide 18G1 ½) and set up over a 2 ml screw cap tube.

Spin 3-4 seconds (the material should be transferred to the 2 ml tube, while the beads stay in the 1.5 ml tube).

Turn the centrifuge on, allow it to reach 700 rpm and then turn off.

Resuspend and transfer to a new 1.5 ml tube (be sure to have at least 700 µl in each tube. Add lysis buffer to bring the volume up to 700 µl, as necessary. Smaller volumes may splash out during sonication).

Step 2a—Sonication

Shear chromatin by sonicating 4 times for 20 seconds at power 1.5 using a Branson Sonifer 250—use the 'Hold' and 'Constant Power' settings. (This should result in sheared DNA with an average size of 400 bp).

Note: Keep samples on ice between each round of sonication. Immerse tip in sample first, turn the power on for 20 seconds, turn the power off and place sample back on ice. Wash the tip with water between sample types (it is not necessary to wash the tip between replicates from the same strain). Before and after use of the sonifer, rinse the tip with 98% EtOH.

Spin for 5 minutes at maximum speed at 4° C. and transfer the supernatant to another tube on ice (Supernatant yeast whole cell extract (yWCE)).

Step 2b—Immunoprecipitation

Set up a new tube on ice containing: 500 µl of yWCE and 30 µl of a suspension of washed magnetic beads pre-bound to anti-Myc antibody.

Vortex the beads well before removing each 30 µl aliquot to ensure equal amounts of beads are added to each tube and that the beads remain in suspension. Set aside 5 µl of WCE in a separate tube (to label as a control later) and store it and the rest of the yWCE at −20° C.

Incubate overnight on a rotating platform at 4° C.

Bead Washing, Elution from Beads and Reversal of Cross Linking

Step 3—Bead Washing

\*\*\*\*\*\*\*\*\*\*\*Work in the Cold Room\*\*\*\*\*\*\*\*\*\*\*

Wash beads using appropriate device (e.g. MPC-E magnet, Dynal), as follows:

Put the first 6 tubes into magnet, invert the tubes once, open the tubes and aspirate the supernatant using a vacuum (also aspirate what is left in the cap), add the appropriate washing solution, close the tubes and put them back on the rotating platform. Proceed with the next 6 tubes and so on. Don't forget to turn the rotator on while you are aspirating the supernatant from the next set of tubes etc.

For this step, you don't need to add protease inhibitors to the lysis buffer.

Wash 2 times with 1 ml lysis buffer.

Wash 2 times with 1 ml lysis buffer containing an additional 360 mM NaCl

720 µl of 5 M NaCl in 10 ml lysis buffer—the final concentration of NaCl is 500 mM.

Wash 2 times with 1 ml wash buffer.

Wash once with 1 ml TE.

After you have removed the TE by aspiration, spin the tubes for 3 minutes at 3000 rpm and remove any remaining liquid with a pipette.

Step 3a—Elution from Beads and Reversal of Cross Links

Add 50 µl elution buffer, vortex briefly to resuspend the beads and incubate at 65° C. for 10 minutes. Vortex briefly every 2 minutes during the incubation.

\*\*\*\*\*\*\*\*The Next Steps should be Done at Room Temperature\*\*\*\*\*\*\*\*

Spin for 30 seconds at maximum speed and transfer 30 µl of supernatant to a new tube. Discard the rest (unless have a special reason to keep it).

Add 120 µl of TE/SDS to the supernatant in the new tube in order to reverse the crosslinking reaction.

Also add 95 µl of TE/SDS to 5 µl of yWCE (prepare one yWCE for each IP).

Incubate overnight at 65° C. in an incubator.

DNA Precipitation

Step 4—Precipitation of DNA

Add 150 µl of "proteinase K mix" to each sample.

Incubate for 2 hours at 37° C. in the warm room.

Extract 2 times with 1 volume of phenol (Sigma Cat. P-4557; OK to use at 4° C.). Spin for about 5 minutes at room temperature for each extraction.

Extract once with 1 volume of chloroform/isoamyl alcohol (Sigma Cat. C-0549).

Add NaCl to 200 mM final (use 8 µl of 5 M stock for 200 µl of sample).

Add 2 volumes of cold EtOH and vortex briefly.

Incubate at −20° C. for at least 15 minutes.

Spin at 14,000 rpm for 10 minutes at 4° C.

Pour off the supernatant, add 1 ml cold 70% EtOH, vortex briefly and spin at 14,000 rpm for 5 minutes at 4° C.

Pour off the supernatant, spin briefly and remove the remaining liquid with a pipette.

Let the pellet dry for a couple of minutes and resuspend the pellet in 30 µl TE containing 10 µg RNaseA (add 33 µl of 10 mg/ml RNaseA to 1 ml of TE).

Incubate for 1 hour at 37° C. in the warm room.

Purify using Qiagen PCR purification kit. Elute with 50 µl of 10 mM Tris pH 8.0.

Store at −20° C. or place on ice and proceed to step 5.

Stop at this stage if you are just going to do a gene-specific PCR, without hybridizing to glass slide arrays.

Blunting DNA and Ligation of Blunt DNA to Linker

Step 5—Blunting DNA

In separate PCR tubes, place 40 µl of immunoprecipitated DNA and 1 µl of whole cell extract DNA plus 39 µl ddH2O. Place on ice. Save the remaining DNAs at −20° C. for gene specific PCR analysis.

Note: If you are going to do a "WCE vs WCE control" (recommended), make 2 extra samples with 1 µl whole cell extract DNA+39 µl ddH2O, using the same whole cell extract DNA for each.

Add 70 µl of:

| | |
|---|---|
| 11 µl | (10X) T4 DNA pol buffer (NE Biolabs cat #007-203) |
| 0.5 µl | BSA (10 mg/ml) (NE Biolabs cat #007-BSA) |
| 0.5 µl | dNTP mix (20 mM each) |
| 0.2 µl | T4 DNA pol (3 U/µµl) (NE Biolabs cat #203L) |
| 57.8 µl | ddH2O |
| 70 µl | Total |

Mix by pipetting and incubate at 12° C. for 20 minutes in a PCR machine

The program name is "12/20", under "Main" in the 2 heads PCR machine. Do not use the heated lid option.

Place on ice and add 12 µl of:

| | |
|---|---|
| 11.5 µl | 3M NaOAc |
| 0.5 µl | glycogen (20 mg/ml) (Roche Molecular Biochemicals cat #901393) |
| 12 µl | Total |

Mix, by vortexing, and add 120 µl of phenol/chloroform/isoamyl alcohol (25:24:1, Sigma cat. P-3803).

Vortex to mix and spin 5 minutes at maximum speed.

Transfer 110 µl to a new 1.5 ml Eppendorf tube and add 230 µl cold EtOH (100%).

Vortex to mix and spin for 15 minutes at 4° C.

Pour off supernatant and wash pellet with 500 µl cold 70% EtOH.

Spin for 5 minutes at 4° C.

Pour off supernatant, spin briefly and remove any remaining liquid with pipette. Allow to air dry briefly.

Resuspend pellet in 25 µl ddH$_2$0 and place on ice.

Step 5a—Ligation of Blunt DNA to Linker

Add 25 µl of cold ligase mix:

| | |
|---|---|
| 8 µl | ddH20 |
| 10 µl | 5X DNA ligase buffer (GibcoBRL) |
| 6.7 µl | annealed linkers (15 µM) (see appendix #2) |
| 0.5 µl | T4 DNA ligase (Life Technologies) |
| 25.2 µl | Total |

Mix by pipetting and incubate overnight at 16° C.

Ligation-Mediated PCR

Step 6—Ligation-Mediated PCR

Add 6 µl of 3M NaOAc (pH 5.2) to linker-ligated DNA. Mix by vortexing and add 130 µl cold EtOH.

Mix by vortexing and spin for 15 minutes at 4° C.

Pour off supernatant and wash with 500 µl 70% EtOH.

Spin for 5 minutes at 4° C.

Pour off supernatant, spin and remove any remaining liquid with a pipette.

Resuspend in 25 µl ddH$_2$O and place on ice.

Add 15 µl of PCR labeling mix:

| | |
|---|---|
| 4 µl | 10X ThermoPol reaction buffer (NE Biolabs) |
| 5.75 µl | ddH2O |
| 2 µl | low T mix (5 mM each dATP, dCTP, dGTP; 2 mM dTTP) |
| 2 µl | Cy3-dUTP or Cy5-dUTP (use Cy5 for IP DNA and Cy3 for WCE DNA) |
| 1.25 µl | oligo oJW102 (40 µM stock) |
| 15 µl | Total |

Try to use Cy3 or Cy5 from the same batch i.e. avoid mixing batches.

Transfer to PCR tubes on ice, place in PCR machine and start program "Cy3" or "Cy5" (the programs are stored under "Main" in our PCR machines or under "FR" in the tetrad PCR machine in the back room):

| Step | Time/Instruction | Temp. | Notes |
|---|---|---|---|
| 1 | 2 min | 55° C. | (make this longer if you have a lot of samples) |
| 2 | 5 min | 72° C. | |
| 3 | 2 min | 95° C. | |
| 4 | 30 sec | 95° C. | |
| 5 | 30 sec | 55° C. | |
| 6 | 1 min | 72° C. | |
| 7 | go to step 4 for X* more times | | |
| 8 | 4 min | 72° C. | |
| 9 | hold | 4° C. | |

*32 cycles (total) for Cy5 and 34 cycles for Cy3

Add 10 µl of polymerase mix during step 1 of PCR:

| | |
|---|---|
| 8 µl | ddH2O |
| 1 µl | 10X ThermoPol reaction buffer (NE Biolabs) |
| 1 µl | Taq polymerase (5 U/µl) (Perkin Elmer: Use Cat. #N801-0060 i.e. regular Taq., do not use AmpliTaq Gold) |
| 0.01 µl | PFU Turbo (2.5 U/µl) (Stratagene Cat #600250-51) |
| 10 µl | Total |

Run 5 µl on a 1.5% agarose gel. (The PCR product should be a smear ranging from 200 bp to 600 bp with an average size of 400 bp).

Purify with Qiaquick PCR purification kit. Elute in 50 µl.

Add 6 µl 3M NaOAc, mix and add 130 µl cold EtOH.

Mix and spin for 15 minutes at 4° C.

Pour off supernatant and wash with 500 µl of 70% EtOH.

Spin for 5 minutes at 4° C.

Pour off supernatant, spin and remove any remaining liquid with a pipette.

Store PCR products at −20° C. Keep in a closed box to prevent exposure to light.

Pre-Hybridization, Probe Preparation, Hybridization and Wash

Step 7—Pre-Hybridization

Incubate slide in 3.5×SSC, 0.1% SDS, 10 mg/ml BSA for 20 minutes at room temperature with agitation (use a stir bar on setting "5") and then 20 minutes at 50° C. suing a pre-warmed solution (place Coplin jar in water bath; use a fresh solution).

Wash slide using RO water.

Blow-dry with nitrogen or by placing slides in a rack and spinning in a centrifuge for 2 min @1 krpm.

Step 7a—Probe Preparation

During slide pre-hybridization, resuspend each target in 30 µl of 3×SSC, 0.1% SDS (these may be hard to resuspend, place in 37° C. heat block and vortex if necessary. This may tale 30-45 min.).

Mix both Cy5 and Cy3 resuspended target, add 4 µl of tRNA (8 mg/ml) and mix well by vortexing.

Boil for 5 minutes in a heat block.

Incubate for 5 minutes at 50° C.

Spin briefly.

Step 7b—Hybridization

Pipette 50 µl of probe onto slide and drop cover slip (use the big one so that it will cover the entire array) onto the liquid. Try to avoid bubbles as they exclude the hybridization solution.

Add water to the holes in the hybridization chamber.

Assemble the chambers and submerge right side up in a 50° C. water bath, allow hybridizing for 20-24 hours.

Step 7c—Wash

Disassemble hybridization chambers with the right side up.

Remove coverslip and immediately place slide in 0.1× SSC, 0.1% SDS at room temperature for 8 minutes with agitation.

Transfer to 0.1×SSC for 5 minutes with agitation.

Note: Transfer slide by slide (do not transfer the whole rack). Rotate slides 180° along the long edge when transferring.

Repeat 0.1×SSC wash 2 more times.

Dry by placing slides in a rack and spinning in a centrifuge for 2 ml @ 1 krpm and scan immediately or store in the dark until scanning.

*******Preparation of Magnetic Beads*******

Prepare the Day Before Use

Take 50 µl of beads (4×10$^8$ beads/ml stock e.g. 2×10$^7$ beads per sample) and place in a 15 ml Falcon tube. Use Dynabeads M-450 pre-coated with rat anti-mouse IgG-2a; Cat. #110.13.

Spin for 1 minute at speed 6 (~3000 rpm) in a tabletop centrifuge (Sorvall RT6000).

Remove supernatant with a pipette and resuspend in 10 ml PBS containing 5 mg/ml BSA (make immediately before use from Sigma BSA powder, cat. A-3350).

Wash again.

Incubate overnight with antibody on a rotating platform at 4° C. (Use 1 µl of anti-Myc 9E11 antibody plus 250 µl PBS+5 mg/ml BSA per 50 µl of beads).

Note: The 9E11 antibody we are using has been purified from acites and concentrated. The amount used has been determined empirically so that the beads are saturated.

Spin for 1 minute at speed 6 (~3000 rpm) in a tabletop centrifuge (Sorvall RT6000).

Remove supernatant with a pipette and resuspend in 10 ml PBS containing 5 mg/ml BSA (make immediately before use, as above).

Wash again.

Resuspend each sample in 30 µl PBS containing 5 mg/ml BSA.

Preparation of Unidirectional Linker

Mix the following:

```
250 µl Tris-HCl (1 M) pH 7.9

375 µl oligo oJW102 (40 µM stock)

375 µl oligo oJW103 (40 µM stock)

oJW102:
GCGGTGACCCGGGAGATCTGAATTC     (SEQ ID NO: 29)

oJW103:
GAATTCAGATC                   (SEQ ID NO: 30)
NOTE: Order these oligos dessicated, then
resuspend in ddH20.
```

Make 50 or 100 µl aliquots in Eppendorf tubes.

Place in a 95° C. heat block for 5 minutes.

Transfer samples to a 70° C. heat block (there should be water in the holes).

Place the block at room temperature and allow it to cool to 25° C.

Transfer the block to 4° C. and allow to stand overnight. Store at −20° C.

Solutions

TBS (Store at 4° C.)

| 1X | 5X | for 1 L of 5X |
|---|---|---|
| 20 mM Tris-HCl pH7.5 | 100 mM Tris-HCl pH 7.5 | 100 ml of 1M |
| 150 mM NaCl | 750 mM NaCl | 150 ml of 5M |

Lysis Buffer (Make Fresh with Cold ddH$_2$0)

| 1X | for 150 ml | for 5 ml |
|---|---|---|
| 50 mM HEPES-KOH pH 7.5 | 7.5 ml of 1 M | 250 µl of 1 M |
| 140 mM NaCl | 4.2 ml of 5 M | 140 µl of 5 M |
| 1 mM EDTA | 300 µµl of 500 mM | 10 µl of 500 mM |
| 1% Triton X-100 | 15 ml of 10% | 500 µl of 10% |
| 0.1% Na-deoxycholate | 3 ml of 5% | 100 µl of 5% |
| 1 mM PMSF, 1 mM Benzamidine | 1.5 ml of 100X | 50 µl of 100X |
| 10 µµg/ml Aprotinin, 1 µg/ml Leupeptin | 1.5 ml of 100X | 50 µl of 100X |
| 1 µµg/ml Pepstatin | 1.5 ml of 100X | 50 µl of 100X |

Wash Buffer (Store at 4° C.)

| 1X | for 500 ml |
|---|---|
| 10 mM Tris-HCl pH 8.0 | 5 ml of 1 M |
| 250 mM LiCl | 25 ml of 5 M |
| 0.5% NP40 | 2.5 ml of 100% |
| 0.5% Na-deoxycholate | 25 ml of 10% |
| 1 mM EDTA | 1 ml of 500 mM |

Elution Buffer (Make with ddH$_2$O, Store at Room Temperature)

| 1X | for 100 ml |
|---|---|
| 50 mM Tris-HCl pH 8.0 | 5 ml of 1 M |
| 10 mM EDTA | 2 ml of 500 mM |
| 1% SDS | 10 ml of 10% |

TE/SDS (Make with ddH2O, Store at Room Temperature)

| 1X | for 500 ml |
|---|---|
| 10 mM Tris HCl pH 8.0 | 5 ml of 1 M |
| 1 mM EDTA | 1 ml of 500 mM |
| 1% SDS | 5 g |

Proteinase K Mix (Make Fresh)

| For 1 sample | For 26 samples |
|---|---|
| 140 µl of TE | 3640 µl |
| 3 µl of glycogen (Boehringer cat# 901393) | 78 µl |
| 7.5 µl of proteinase K (20 mg/ml stock) (Gibco 25530-049) | 195 µl |

20×SSC

| 20X | for 1 L solution |
|---|---|
| 3 M NaCl | 175.32 g |
| 0.3M Na$_3$citrate•2H$_2$O pH"d to 7.0 with HCl | 88.23 g |

PMSF/Benzamidine Mix 110× Stock (Aliquot and Store at −20° C.)

| 1X | For 10 ml of 100X |
|---|---|
| 1 mM PMSF | 0.1742 g |
| 1 mM Benzamidine | 0.1566 g |
| EtOH | Bring to a volume of 10 ml |

Aprotinin/Leupeptinin Mix 100× Stock (Aliquot and Store at −20° C.)

| 1X | For 10 ml of 100X |
|---|---|
| 10 μg/ml Aprotinin | 0.01 g |
| 1 μg/ml Leupeptin | 0.001 g |
| ddH$_2$O | Bring to a volume of 10 ml |

Pepstatin Mix 100× (Aliquot and Store at −20° C.)

| 1X | For 10 ml of 100X |
|---|---|
| 1 μg/ml Pepstatin | 0.001 g |
| DMSO | Bring to a volume of 10 ml |

Location Analysis

DNA microarrays with consistent spot quality and even signal background were important for maximizing reproducibility and dynamic range. The LM-PCR method described here was developed to permit reproducible amplification of very small amounts of DNA; signals for greater than 99.8% of genes were essentially identical within the error range (p-value <=$10^{-3}$) when independent samples of 1 ng of genomic DNA were amplified with the LM-PCR method. Each experiment was carried out in triplicate, allowing an assessment of the reproducibility of the binding data. Furthermore, a single-array error model was adopted to handle noise associated with low intensity spots and to average repeated experiments with appropriate weights.

Location Analysis: from Scanning Image to Intensity

Images of Cy3 and Cy5 fluorescence intensities were generated by scanning the arrays using a GSI Lumonics Scanner. The Cy3 and Cy5 images were analyzed using ArrayVision software, which defined the grid of spots and quantified the average intensity of each spot and the surrounding background intensity. The background intensity was subtracted from the spot intensity to give the final calculated spot intensity. The intensities of all of the spots from the Cy5 and Cy3 scans were summed, and the ratio of total Cy5/Cy3 intensity was set equal to one. For each spot the ratio of corrected Cy5/Cy3 intensity was computed.

Location Analysis: Single Array Error Model

The quantitative amplification of small amounts of DNA generates some uncertainty in values for the low intensity spots. In order to track that uncertainty and average repeated experiments with appropriate related weights, we adopted an single-array error model that was first described by Roberts, C. J., et al., "Signaling and circuitry of multiple MAPK pathways revealed by a matrix of global gene expression profiles," Science 287, 873-80 (2000). According to this error model, the significance of a measured ratio at a spot is defined by a statistic X, which takes the form $$X = \frac{a_2 - a_1}{(\sigma_1^2 + \sigma_2^2 + f^2(a_j^2 + a_2^2))^{1/2}} \quad (1)$$

where $a_{1,2}$ are the intensities measured in the two channels for each spot, $\sigma_{1,2}$ are the uncertainties due to background subtraction, and f is a fractional multiplicative error such as would come from hybridization non-uniformities, fluctuations in the dye incorporation efficiency, scanner gain fluctuations, etc. X is approximately normal. The parameters σ and f were chosen such that X has unit variance. The significance of a change of magnitude |x| is then calculated as $$p = 2(1 - Erf(|X|)) \quad (2)$$

Location Analysis: Weighted Average from Triplicate Measurements

For each factor, three independent experiments were performed and each of the three samples were analyzed individually using a single-array error model. The average binding ratio and associated p-value from the triplicate experiments were calculated using a weighted average analysis method (Roberts, C. J., et al., "Signaling and circuitry of multiple MAPK pathways revealed by a matrix of global gene expression profiles," Science 287, 873-80 (2000)).

The method to combine repeated measurements of chromosomal binding is adapted, with a few modifications, from a method by developed by Roberts, C. J., et al. "Signaling and circuitry of multiple MAPK pathways revealed by a matrix of global gene expression profiles," Science 287, 873-80 (2000) to average multiple measurements of gene expression. Briefly, the binding ratio is expressed as the $\log_{10}(a_2/a_1)$, where $a_1, a_2$ are the intensities measured in the two channels for each spot. The uncertainty in the log(Ratio) is defined as $$\sigma_{\log 10(a_1/a_2)} = \log_{10}(a_2/a_1)/X \quad (3)$$

where X is the statistics derived from single array error model. We use the minimum-variance weighted average to compute the mean $\log_{10}(a_2/a_1)$ of each spot:

$$w_i = 1/\sigma_j^2 \quad (4)$$

$$\bar{x} = \sum_{i=1,n} w_j x_j / \sum w_i \quad (5)$$

Here $\sigma_1$ is the error of $\log_{10}(a_2/a_1)$ from (3), $x_i$ stands for i-th measurement of $\log_{10}(a_2/a_1)$, n is the number of repeats.

The error of $\bar{x}$ can be computed in two ways. One is to propagate the errors $\sigma_i$, another is from the scatter of $x_i$:

$$\sigma_p^2 = 1/\Sigma w_i \quad (6)$$

For the average of multiple slides, the significance statistic X is computed as:

$$X = \bar{x}/\sigma_p \quad (7)$$

and the confidence is computed using Equation (2) from the single array error model.

Location Analysis: Gene Assignment

The intergenic regions present on the array were assigned to the gene or genes found transcriptionally downstream. In some cases, a single intergenic region contains the promoter for two divergently transcribed genes (e.g. HHF2 and HHT2 or CLN2 and BBP1). In such cases, the intergenic region was assigned to both genes, and gene expression data were used to "discipline" the binding location data. This was accomplished by selecting genes whose promoters were bound by factors and whose expression oscillates during the cell cycle. Among genes whose promoters were bound by at least one of the factors and which were expressed in a cell cycle-dependent fashion, we found only 18 examples of intergenic regions that lie at the center of divergently transcribed genes.

Motif Search

In order to identify DNA binding motifs we used a set of promoters commonly regulated by a transcription factor (with p<0.001) as input for AlignACE (Hughes, J. D., et al, *J Mol Biol* 296, 1205-14 (2000)). We ran the program with the default parameters, adjusting only the parameter that defines the size of the expected motif (numcolumn), which we systematically explored within 7 to 25 nucleotides. The identified motifs were run on ScanACE and on MotifStats (Hughes, J. D., et al, *J Mol Biol* 296, 1205-14 (2000)) in order to assign motif specificity to the group of promoters that were used as input. In order to determine which promoter contains a given motif, we used Scan-ACE, and we included all the promoters with scores greater than one standard deviation below the average score of the sites found in the initial AlignACE search.

Statistics

In order to explore the statistical significance of the overlap between the set of targets of a factor and the genes expressed in a particular cell cycle stage we used the hypergeometric distribution as described (Tavazoie, S., et al., "Systematic determination of genetic network architecture," *Nat Genet* 22, 281-5., (1999))

Data and Quality Control

Two measures of quality control are described here. First, scatter plots for the array data obtained in each of the experiments are provided. Second, we compare results of these experiments with results reported previously by other investigators.

Comparison to Literature

All but one of the transcription factor-promoter interactions previously established in vivo were confined by the location data, even when the highest stringency criteria was used (p<0.001). We confirmed that Mcm1, Fkh2 and Ndd1 bind to the CLB2, SWI5 and YJL051W promoters (Zhu et al. *Nature,* 406:90-94 (2000); Koranda et al., *Nature,* 406:94-98 (2000)), SBF binds to the CLN2 promoter (Koch, C., et al., *Genes Dev* 10, 129-41 (1996)), Mcm1 binds to the STE2 promoter (Zhu et al. *Nature,* 406:90-94 (2000)), and Swi4 binds to the HO promoter (Cosma, M. P., et al., *Cell* 97, 299-311 (1999)).

We did not observe Swi5 binding to the HO promoter, which also occurs in vivo (Cosma, M. P., et al., "Ordered recruitment of transcription and chromatin remodeling factors to a cell cycle- and developmentally regulated promoter," *Cell* 97, 299-311 (1999)), because Swi5 binding can be detected only in synchronized cells, and even then only transiently (5 minutes duration) (Cosma, M. P., et al., "Ordered recruitment of transcription and chromatin remodeling factors to a cell cycle- and developmentally regulated promoter," *Cell* 97, 299-311 (1999)). Additional genes have been suggested as targets of these cell cycle transcription factors based on indirect evidence, but our data do not confirm that all of these genes are direct targets of these regulators (Althoefer, H., et al., "Mcm1 is required to coordinate G2-specific transcription in *Saccharomyces cerevisiae,*" *Mol Cell Biol* 15, 5917-28 (1995); Piatti, S., et al., "Cdc6 is an unstable protein whose de novo synthesis in GC is important for the onset of S phase and for preventing a 'reductional' anaphase in the budding yeast *Saccharomyces cerevisiae,*" *Embo J* 14, 3788-99 (1995); Toone et al., 1995; Verma, R., et al., "Identification and purification of a factor that binds to the Mlu I cell cycle box of yeast DNA replication genes," *Proc Natl Acad Sci USA* 88, 7155-9 (1991); Koch et al. *Science,* 261:1551-1557 (1993); Gordon, C. B., and Campbell, J. L., "A cell cycle-responsive transcriptional control element and a negative control element in the gene encoding DNA polymerase alpha in *Saccharomyces cerevisiae,*" *Proc Natl Acad Sci USA* 88, 6058-62 (1991); Pizzagalli, A., et al., "DNA polymerase I gene of *Saccharomyces cerevisiae:* nucleotide sequence, mapping of a temperature-sensitive mutation, and protein homology with other DNA polymerases," *Proc Natl Acad Sci USA* 85, 3772-6 (1988); Igual, J. C., et al., "Coordinated regulation of gene expression by the cell cycle transcription factor Swi4 and the protein kinase C MAP kinase pathway for yeast cell integrity," *Embo J* 15, 5001-13 (1996); Lowndes, N. F., et al., "Coordination of expression of DNA synthesis genes in budding yeast by a cell-cycle regulated trans factor," *Nature* 350, 247-50 (1991)).

Download Raw Data

The raw data for the location analysis experiments for each of the nine cell cycle activators are available as a single text file with each column separated by tabs. Descriptions of the contents of each column are provided in the first two rows.

'spot name' refers to an intergenic region. It has been assigned a systematic name that includes the letter 'i' followed by the systematic ORF name that is to the left of the intergenic region.

'pcr quality' is a qualitative description of the pcr products as seen on an acrylamide gel. 'good' means that the band was the correct size and clearly visible. 'w' indicates that the band intensity was 'weak', 'vw' indicates 'very weak' intensity. 'no' means that no band was seen, and 's' indicates that the size of the band was not what was expected.

'# of promoters on spot' denotes the number of genes which the intergenic region contains promoters for. 'assigned gene' is the name of each orf whose promoter is contained in the given intergenic region, 'Orf' is the gene name.

'p-value' and 'average ratio' are the combined values for replicate experiments for each of the factors tested.

The last columns in the file are the cell cycle stage as described by Spellman, P. T. et al., *Mol Biol Cell* 9, 3273-97 (1998), the phase of the gene, and the cell cycle stage as described by Cho, R. J., et al., *Mol Cell* 2, 65-73 (1998).

Serial Regulation of Transcriptional Regulators in the Yeast Cell Cycle

Genomic binding sites were identified for the nine known yeast cell cycle transcription activators, revealing how these factors coordinately regulate global gene expression and diverse stage-specific functions to produce a continuous cycle of events. One fundamental insight that emerged from these results is that a complete transcriptional regulator) circuit is formed by activator complexes that control next-stage activators. The results also show that stage-specific activator complexes regulate genes encoding CDK regulators necessary for both stage entry and for progression into the next stage of the cell cycle. This global information provides a map of the regulatory network that controls the cell cycle.

TABLE 4

Binding of Cell Cycle Activators to Functional Categories

| Functional Category | Gene | SBF | MBF | Fkh1 | Fkh2 | Mcm1/ Fkh2/ Ndd1 | Mcm1 | Ace2 | Swi5 | YPD Title Line ™ © 2001 Proteome, Inc. Reprinted with permission. Last Updated: [Jul. 26, 2000] |
|---|---|---|---|---|---|---|---|---|---|---|
| cell cycle control | PCL9 | | | | | | | | + | Cyclin that associates with Pho85p |
| cell cycle control | SIC1 | | | | | | | | + | P40 inhibitor of Cdc28p-Clb protein kinase complex |
| cell cycle control | SWI4 | + | + | | | + | | | | Transcription factor that participates in the SBF complex (Swi4p-Swi6p) for regulation at the cell cycle box (CCB) element, has 2 ankyrin repeats |
| cell cycle control | PCL2 | + | | | | | | + | + | Cyclin, found partly in association with Pho85p |
| cell cycle control | CLB6 | + | + | | + | | | | | B-type cyclin appearing late in G1, involved in initiation of DNA synthesis |
| cell cycle control | CLB5 | | + | | | | | | | B-type cyclin appearing late in G1, involved in initiation of DNA synthesis |
| cell cycle control | SWE1 | 0 | + | | | | | | | Serine/tyrosine dual-specificity protein kinase; able to phosphorylate Cdc28p on tyrosine and inhibit its activity |
| cell cycle control | PCL1 | + | + | | + | | + | | | G1/S-specific cyclin that can interact with the Cdc28p-like kinase Pho85p |
| cell cycle control | CLN2 | + | | | | | | | | G1/S-specific cyclin, interacts with Cdc28p protein kinase to control events at START |
| cell cycle control | CLN1 | + | + | + | + | | | | | G1/S-specific cyclin that interacts with Cdc28p protein kinase to control events at START |
| cell cycle control | OPY2 | | + | | | | | | | Protein that may be involved in cell-cycle regulation; overproduction causes insensitivity to alpha-factor arrest |
| cell cycle control | NDD1 | + | | | | | | | | Protein required for nuclear division; positively but indirectly affects transcription of a subset of genes required for the cell cycle |
| cell cycle control | CLB4 | | | | + | | | | | G2/M-phase-specific cyclin |
| cell cycle control | SIM1 | + | | | + | | + | | | Protein involved in the aging process and in regulation of the cell cycle |
| cell cycle control | PCL7 | | | | | | | | + | Cyclin, associates with Pho85p |
| cell cycle control | HSL7 | | | | + | | | | | Negative regulatory protein of the Swe1p protein kinase |
| cell cycle control | APC1 | | < | | | | | | | Component of the anaphase-promoting complex (APC); required for Clb2p degradation and for the metaphase-anaphase transition |
| cell cycle control | ACE2 | | | + | + | + | | | | Metallothionein expression activator with similarity to Swi5p, has three tandem C2H2-type zinc fingers |
| cell cycle control | CLB2 | + | | + | + | + | | | | G2/M-phase-specific cyclin |
| cell cycle control | SWI5 | | | + | + | | | | | Transcription factor that controls cell cycle-specific transcription of HO, has three tandem C2H2-type zinc fingers$_{cell\ cycle\ control}$ |
| cell cycle control | HDR1 | | | | + | | | | | Protein involved in meiotic segregation |
| cell cycle control | TEM1 | | | | + | + | | | | GTP-binding protein involved in termination of M-phase, member of the ras superfamily |
| cell cycle control | CDC20 | | | | + | + | | | | Activator of anaphase promoting complex (APC), required for microtubule function at mitosis and for exit |

TABLE 4-continued

Binding of Cell Cycle Activators to Functional Categories

| Functional Category | Gene | SBF | MBF | Fkh1 | Fkh2 | Mcm1/ Fkh2/ Ndd1 | Mcm1 | Ace2 | Swi5 | YPD Title Line ™ © 2001 Proteome, Inc. Reprinted with permission. Last Updated: [Jul. 26, 2000] |
|---|---|---|---|---|---|---|---|---|---|---|
| | | | | | | | | | | from anaphase, contains WD (WD-40) repeats |
| cell cycle control | SPO12 | | + | | + | + | | | | Sporulation protein required for chromosome division in meiosis I |
| cell cycle control | CLN3 | | | | | | + | + | < | G1/S-specific cyclin that interacts with Cdc28p protein kinase to control events at START |
| cell cycle control | DBF2 | | | | | | + | | | Serine/threonine protein kinase related to Dbf20p, required for events in anaphase/telophase |
| cell cycle control, mating | FAR1 | | | | | | + | | | Inhibitor of Cdc28p-Cln1p and Cdc28p-Cln2p kinase complexes involved in cell cycle arrest for mating |
| budding | CHS1 | | | | | | | | + | Chitin synthase I, has a repair function during cell separation |
| budding | TEC1 | | | | | | | | + | Transcriptional activator, involved with Ste12p in pseudohyphal formation |
| budding | EGT2 | | | | | | | + | + | Cell-cycle regulation protein, may be involved in the correct timing of cell separation after cytokinesis |
| budding | GIC2 | + | + | | | | | | | Putative effector of Cdc42p, important for bud emergence |
| budding | SCW11 | | | | | | | + | + | Putative cell wall protein with similarity to Scw10p |
| budding | GIN4 | + | | | | | + | | | Serine/threonine-protein kinase required for septin organization at the bud neck, has similarity to Ycl024p |
| budding | BUD9 | + | | + | | | + | + | + | Protein required for bipolar budding; mutant diploid strains bud only at distal pole |
| budding | OCH1 | + | | | | | | | | Alpha-1,6-mannosyltransferase, involved in initiation of mannose outer chain elongation of N-linked oligosaccharides of type Man[9]GlcNac[2] |
| budding | CTS1 | | | | + | | | + | + | Endochitinase |
| budding | RSR1 | + | | | | | | | | GTP-binding protein involved in bud site selection, member of the ras family in the ras superfamily |
| budding | | + | + | | | | | + | | |
| budding | MSB2 | + | | | | | | | | Protein for which overproduction suppresses bud emergence defect of cdc24 mutant |
| budding | MNN1 | + | | | | | | | | Alpha-1,3-mannosyltransferase, required for complex glycosylation of both N- and O-oligosaccharides |
| budding | EXG1 | + | + | + | + | | | + | + | Exo-beta-1,3-glucanase (I/II); major isoform involved in cell wall beta-glucan assembly |
| budding | FKS1 | + | | | | | | | | Component of beta-1,3-glucan synthase, probably functions as an alternate subunit with Gsc2p with which it has strong similarity |
| budding | | + | | | | | | | | |
| budding | PSA1 | + | | | | | | + | | Mannose-1-phosphate guanyltransferase; GDP-mannose pyrophosphorylase |
| budding | KRE6 | < | | | | | | | | Glucan synthase subunit required for synthesis of beta-1,6-glucan |

TABLE 4-continued

Binding of Cell Cycle Activators to Functional Categories

| Functional Category | Gene | SBF | MBF | Fkh1 | Fkh2 | Mcm1/Fkh2/Ndd1 | Mcm1 | Ace2 | Swi5 | YPD Title Line ™ © 2001 Proteome, Inc. Reprinted with permission. Last Updated: [Jul. 26, 2000] |
|---|---|---|---|---|---|---|---|---|---|---|
| budding | GIC1 | + | | | + | | | | | Putative effector of Cdc42p, important for bud emergence |
| budding | CWP1 | + | | | + | | | | | Mannoprotein of the cell wall, member of the seripauperin (PAU) family |
| budding | CIS3 | + | | | + | | | | | Cell wall protein with similarity to members of the Pir1p/Hsp150p/Pir3p family |
| budding | | + | + | + | + | | | + | | |
| budding | BUD4 | | | + | + | + | | | | Protein required for axial budding but not for bipolar budding |
| budding | WSC4 | | | | | | | + | | Protein required for secretory protein translocation, for maintenance of cell wall integrity, and for the stress response |
| budding | BUD8 | | | + | | | | | | Protein required for bipolar budding, has an RNA recognition (RRM) domain |
| budding | SCW4 | + | | | | | | | | Cell wall protein, has similarity to Scw10, Bgl2p, and other cell wall glucanases |
| budding | | + | | | + | + | | | | |
| budding | CHS2 | | | | | | | | | Chitin synthase II, responsible for primary septum disk |
| budding | SKN1 | | | | | | + | | | Glucan synthase subunit involved in synthesis of beta-1,6-glucan |
| dna replication | RNR1 | + | + | | + | | | | | Ribonucleotide reductase (ribonucleoside-diphosphate reductase) large subunit, converts deoxyribonucleoside diphosphate to ribonucleoside diphosphate |
| dna replication | RAD27 | | | + | | | | | | Single-stranded DNA endonuclease and 5'-3' exonuclease that functions in the MSH2-MLH1-PMS1-dependent mismatch repair system |
| dna replication | CDC21 | | | + | | | | | | Thymidylate synthase, converts dUMP to dTMP |
| dna replication | IRR1 | | | + | | | | | | Component of cohesin complex; required for sister chromatid cohesion during DNA replication |
| DNA replication | MCD1 | | | + | | | | | | Cohesin, protein required for mitotic chromatid cohesion |
| dna replication | PDS5 | | + | + | + | | | | | Protein of unknown function; loss can lead to precocious separation of sister chromatids |
| dna replication | RAD51 | | | + | + | | | | | Protein that stimulates pairing and strand-exchange between homologous single-stranded and double-stranded DNA, functionally similar to E. coli RecA protein |
| dna replication | DUN1 | | | + | | | | | | Protein kinase required for induction of Rnr3p and DNA repair genes after DNA damage |
| dne replication | ALK1 | | | | | | + | | | DNA damage-responsive protein |
| chromatin | CTF18 | | | + | | | | | | Protein required for accurate chromosome transmission in mitosis and maintenance of normal telomere length; homolog of Rfc1p, Rfc2p, Rfc3p, Rfc4p, and Rfc5p |
| chromatin | HHF1 | | | < | | | | | | Histone H4, identical to Hhf2p |
| chromatin | HHT1 | | | < | | | | | | Histone H3, identical to Hht2p |

TABLE 4-continued

Binding of Cell Cycle Activators to Functional Categories

| Functional Category | Gene | SBF | MBF | Fkh1 | Fkh2 | Mcm1/ Fkh2/ Ndd1 | Mcm1 | Ace2 | Swi5 | YPD Title Line ™ © 2001 Proteome, Inc. Reprinted with permission. Last Updated: [Jul. 26, 2000] |
|---|---|---|---|---|---|---|---|---|---|---|
| chromatin | HTB2 | + | | | | | | | | Histone H2B, nearly identical to Htb1p |
| chromatin | HTB1 | + | | | | | | | | Histone H2B |
| chromatin | HTA1 | + | | | | | | | | Histone H2A, identical to Hta2p |
| chromatin | HTA2 | + | | | | | | | | Histone H2A, identical to Hta1p |
| chromatin | HHO1 | + | | | | | | | | Histone H1 |
| chromatin | TEL2 | | | + | | | | | | Protein involved in controlling telomere length and telomere position effect |
| chromatin | ARP7 | | | + | | | | | | Component of SWI-SNF global transcription activator complex and RSC chromatin remodeling complex; acts to assist gene-specific activators through chromatin remodeling |
| chromatin | HTA3 | + | | | | | | | | Histone-related protein that can suppress histone H4 point mutation |
| chromatin | HOS3 | | | + | | | | | | Histone deacetylase, has similarity to Hda1p, Rpd3p, Hos2p, and Hos1p, insensitive to trichostatin A |
| pre replication | MCM3 | | | | | | + | | | Member of the MCM/P1 family, part of the MCM complex that assembles at ARS elements to initiate replication |
| pre replication, cell cycle control | CDC6 | + | + | | | | + | | | Protein that regulates initiation of DNA replication, binds to origins of replication at the end of mitosis, directing the assembly of MCM proteins and the pre-replication complex, member of the AAA+ family of ATPases |
| pre replication | CDC46 | | | | | | + | | | Member of the MCM/P1 family, component of the MCM complex that binds at ARS elements to initiate DNA replication |
| pre replication | CDC45 | | + | | | | | | | Protein required for initiation of chromosomal DNA replication |
| pre replication | MCM2 | | + | | | | | | | Member of the MCM/P1 family that acts as a complex at ARS sequences to initiate DNA replication |
| pre replication | MCM6 | | | | | | + | | | Protein involved in DNA replication, member of the MCM/P1 family of proteins |
| mating | ASH1 | | | | | | | | + | GATA-type transcription factor, negative regulator of HO expression localized preferentially in daughter cells |
| mating | AGA2 | | | | | | + | | | a-Agglutinin binding subunit |
| mating | AGA1 | + | + | | | | + | | | a-Agglutinin anchor subunit |
| mating | HO | + | | | | | | | | Homothallic switching endonuclease, initiates mating type interconversion by making a double-stranded break in the expressed MAT gene |
| mating | MFA1 | | | | | | + | | | Mating pheromone a-factor, nearly identical to a-factor encoded by MFA2, exported from the cell by Ste6p |
| mating | MFA2 | | | | | | + | | + | Mating pheromone a-factor, nearly identical to a-factor encoded by MFA1, exported from the cell by Ste6p |
| mating | STE6 | | | | | | + | | | Membrane transporter responsible for export of a |

TABLE 4-continued

Binding of Cell Cycle Activators to Functional Categories

| Functional Category | Gene | SBF | MBF | Fkh1 | Fkh2 | Mcm1/Fkh2/Ndd1 | Mcm1 | Ace2 | Swi5 | YPD Title Line ™ © 2001 Proteome, Inc. Reprinted with permission. Last Updated: [Jul. 26, 2000] |
|---|---|---|---|---|---|---|---|---|---|---|
| mating | STE2 | | | | | | + | | | factor mating pheromone member of ATP-binding cassette (ABC) superfamily Pheromone alpha-factor G protein-coupled receptor (GPCR), member of the GPCR or seven transmembrane segments (7-TMS) superfamily |
| mating | FAR1 | | | | | | + | | | Inhibitor of Cdc28p-Cln1p and Cdc28p-Cln2p kinase complexes involved in cell cycle arrest for mating. |
| other | YOR066W | | | | | | + | | | Protein of unknown function |
| other | ICS2 | | | | | | | + | + | Protein required for normal resistance to copper |
| other | YDR157W | | | | | | | + | | Hypothetical ORF |
| other | YKL151C | | | | | | | + | | Protein of unknown function |
| other | PST1 | | | | | | | | + | Protein with similarity to members of the Sps2p-Ecm33p-Ycl048p family |
| other | GAT3 | | | | | | | | + | Putative GATA zinc finger transcription factor |
| other | YPL158C | | | | | | | | + | Protein of unknown function |
| other | UTR2 | + | | | + | + | | | | Cell wall protein |
| other | HSP150 | | | | | | | + | + | Secreted O-glycosylated protein required for tolerance to heat shock, member of Pir1/Hsp150p/Pir3 family of proteins with variable number of tandem internal repeats |
| other | YRF1-1 | + | | | | | | | + | Protein with near identity of the family of subtelomerically-encoded proteins including Yil177p, Yhl049p, and Yjl225p |
| other | FAA3 | | | | | | | | + | Acyl-CoA synthase (long-chain fatty acid CoA ligase); activates endogenous but not imported fatty acids |
| other | PIR3 | | | | | | + | | + | Protein with similarity to members of the Pir1p/Hsp150p/Pir3p family |
| other | YFL065C | | | | | | | | + | Protein with similarity to other subtelomerically-encoded proteins including Yhl049p, Yil177p, Yjl225p, Yer190p, Yhr218p, and Yel076p |
| other | PIR1 | | | | | | + | | + | Protein required for tolerance to heat shock, member of the Pir1p/Hsp150p/Pir3p family |
| other | ELO1 | + | + | | | + | | | | Fatty acid elongation protein involved in elongation of tetradecanoic acid (14 |
| other | PLB3 | + | | | | | | | | Phospholipase B (lysophospholipase) |
| other | YGR086C | | | | | | | | + | Protein of unknown function; induced by high salt and low pH |
| other | YHB1 | | | | | | | + | + | Flavohemoglobin involved in protection from nitrosative stress, distantly related to animal hemoglobins |
| other | PIG1 | | | | | | + | | | Protein that interacts with Gsy2p; possible regulatory subunit for the PP1 family protein phosphatase Glc7p |
| other | CST13 | | | + | + | | | + | + | Protein required for optimal growth and germination rate |
| other | YRF1-7 | | | + | | | | + | + | Protein with near identity to other subtelomerically-encoded protein, including Ygr296p |
| other | YLR465C | | | | | | | | + | Protein of unknown function, questionable ORF |

TABLE 4-continued

Binding of Cell Cycle Activators to Functional Categories

| Functional Category | Gene | SBF | MBF | Fkh1 | Fkh2 | Mcm1/Fkh2/Ndd1 | Mcm1 | Ace2 | Swi5 | YPD Title Line ™ © 2001 Proteome, Inc. Reprinted with permission. Last Updated: [Jul. 26, 2000] |
|---|---|---|---|---|---|---|---|---|---|---|
| other | YLR194C | | | | | | | | + | Protein of unknown function |
| other | MDJ2 | | | | | | | + | + | Protein involved in import and folding of mitochondrial proteins; has similarity to E. coli DnaJ and other DnaJ-like proteins, function partially overlaps that of Mdj1p |
| other | YLR463C | | | | | | | | + | Protein of unknown function with similarity to other subtelomerically-coded proteins |
| other | YRF1-4 | | | | | | | | + | Protein with similarity to other subtelomerically-coded Y'-helicase proteins |
| other | YJL225C | | | | | | | | + | Protein with near identity to other subtelomerically-encoded proteins including Yil177p, Yhr219p, and Yhl079p |
| other | YRF1-5 | | | | | | | | + | Y'helicase with near identity to other subtelomerically-encoded proteins including Yer189p, Yml133p, and Yjl225p |
| other | YER189W | + | + | | + | | | + | + | Protein with similarity to subtelomerically-encoded proteins including Yil177p, Yhl049p, and Yjl225p |
| other | YLR464W | | | | | | | | + | Protein with similarity to other subtelomerically-coded proteins |
| other | YBL111C | | | | | | | | + | Protein of unknown function; subtelomerically encoded |
| other | YBL113C | | | | | | | | + | Protein of unknown function; subtelomerically encoded |
| other | YEL077C | | | | | | | | + | Hypothetical ORF |
| other | YFL064C | | | | | | | | + | Protein with similarity to other subtelomerically-encoded proteins including Yhl049p, Yil177p, Yjl225p, Yer189p, Yel075p, and Yer190p |
| other | YRF1-6 | + | | | | | + | | + | Protein with near identity to other subtelomerically-encoded proteins |
| other | YBL112C | | | | | | | | + | Hypothetical ORF |
| other | YLR462W | | | | | | | | + | Protein of unknown function |
| other | TSL1 | + | + | + | | | | + | + | Component of the trehalose-6-phosphate synthase/phosphatase complex; alternate third subunit with Tps3p |
| other | YRF1-2 | + | + | | + | | | + | + | Protein with similarity to other subtelomerically-encoded proteins including Yil177p |
| other | YML133C | | | | | | | | + | Protein with similarity to other subtelomerically-encoded proteins including Yer189p, and Yjl225p |
| other | YIL177C | | | | | | | | + | Protein with similarity to subtelomerically-encoded proteins including Yjl225p, Yfl068p, and Yhl093p |
| other | YRF1-3 | | | | + | | | | + | Protein with similarity to other subtelomerically-encoded proteins including Yer190p |
| other | YHR149C | + | + | | | | | | | Protein of unknown function |
| other | YBR071W | + | + | + | | | | | | Protein with weak similarity to Herpesvirus saimiri EERF2 |
| other | SPT21 | + | + | | | | | | | Protein that amplifies the magnitude of transcriptional regulation at various loci |
| other | YDR528W | | | | | + | | | | Protein of unknown function |
| other | PRY3 | | | + | + | | | + | + | Protein with similarity to plant pathenogenesis-related |

TABLE 4-continued

Binding of Cell Cycle Activators to Functional Categories

| Functional Category | Gene | SBF | MBF | Fkh1 | Fkh2 | Mcm1/ Fkh2/ Ndd1 | Mcm1 | Ace2 | Swi5 | YPD Title Line ™ © 2001 Proteome, Inc. Reprinted with permission. Last Updated: [Jul. 26, 2000] |
|---|---|---|---|---|---|---|---|---|---|---|
| | | | | | | | | | | proteins, may have a role in mating efficiency |
| other | YJR030C | | + | | | | | | | Protein of unknown function |
| other | PDR16 | + | | | | | | | | Protein involved in lipid biosynthesis and multidrug resistance |
| other | SAT2 | + | + | + | | | | | | Protein involved in osmotolerance |
| other | YGR151C | + | | | | | | | | Protein of unknown function |
| other | SVS1 | + | | | | | | | | Serine- and threonine-rich protein required for vanadate resistance |

Previous Evidence

The genome-wide location data described here identifies the promoters bound in vivo by all known yeast cell cycle transcription factors (Table 5). Some of these factor-promoter interactions were suggested previously using different methods, and a summary of all the targets genes identified by the current study for which previous evidence exists is provided here. The previously reported evidence is separated into four categories:

1. In vivo binding, which includes chromatin immuno-precipitation and in vivo footprinting.
2. In vitro binding, which includes gel retardation assays and DNAse I footprinting.
3. Genetic analysis, which includes the effects of genetic manipulations (such as mutations or overproduction) on target genes.
4. Sequence analysis, which includes the identification of DNA binding motifs in the promoters of target genes.

A genome-wide location analysis technique has recently been used to identify the set of cell cycle genes controlled by MBF and SBF (Iyer, V. R., et al., Nature 409, 533-8 (2001)). A list of all the target genes identified by the current study that were also identified by Iyer, V. R., et al., Nature 409, 533-8 (2001) is provided here. The overlap between the genes identified by Iyer et al. and this study is approximately 75%.

TABLE 5

| | | Evidence | | | |
|---|---|---|---|---|---|
| Gene | Transcription factor | In vivo binding | In vitro binding | Genetic analysis | Sequence analysis |
| ACE2 | Mcm1 | | | Althoefer et al., 1995 | |
| | Fkh2 | | Pic et al., 2000 | | Pic et al., 2000 |
| ASH1 | Swi5 | | | Bobola et al., 1996 | |
| CDC21 | Swi6 | | Verma et al., 1991 Dirick et al., 1992 | Dirick et al., 1992 | |
| | Mbp1 | | Schwob and Nasmyth 1993 Verma et al., 1991 Dirick et al., 1992 | Koch et al., 1993 | McIntosh et al., 1988 McIntosh et al., 1991 |
| CDC46 | Mcm1 | | | McInerny et al., 1997 | McInerny et al., 1997 |
| CDC6 | Mbp1 | | Verma et al., 1991 | | Zhou and Jong, 1993 |
| | Swi6 | | Verma et al., 1991 | Patti et al., 1995 | |
| | Mcm1 | | | McInerny et al., 1997 | McInerny et al., 1997 |
| CLB2 | Mcm1 | Althoefer et al., 1995 Koranda et al., 2000 | Kumar et al., 2000 | Althoefer et al., 1995 | Kuo et al., 1994 Althoefer et al., 1995 |
| | Fkh1 | Koranda et al., 2000 Kumar et al., 2000 | | Hollnhorst et al., 2000 Zhu et al., 2000 Kumar et al., 2000 | |
| | Fkh2 | Koranda et al., 2000 Zhu et al., 2000 Kumar et al., 2000 | Kumar et al., 2000 | Hollnhorst et al., 2000 Pic et al., 2000; Zhu et al., 2000 Kumar et al., 2000 | Pic et al., 2000 |
| | Ndd1 | Koranda et al., 2000 | | Loy et al., 1999 | |
| CLB5 | Mbp1 | | Schwob and Nasmyth 1993 | Koch et al., 1993 | |
| | Swi6 | | Schwob and Nasmyth 1993 | Schwob and Nasmyth 1993 | |
| CLN1 | Swi4 | | Partridge et al., 1997 | Nasmyth and Dirick 1991 Ogas et al., 1991 | Ogas et al., 1991 |
| | Swi6 | | Partridge et al., 1997 | Nasmyth and Dirick 1991 Dirick et al., 1992 | |

TABLE 5-continued

| Gene | Transcription factor | Evidence | | | |
|---|---|---|---|---|---|
| | | In vivo binding | In vitro binding | Genetic analysis | Sequence analysis |
| CLN2 | Swi4 | Koch et al., 1996 | Nasmyth and Dirick 1991 | Nasmyth and Dirick 1991 Ogas et al., 1991 | Ogas et al., 1991 Koch et al., 1996 |
| | Swi6 | | Nasmyth and Dirick 1991 | Nasmyth and Dirick 1991 Dirick et al., 1992 | |
| CLN3 | Mcm1 | | | McInerny et al., 1997 | Kuo et al., 1994 McInerny et al., 1997 |
| CTS1 | Swi5 | | Knapp et al., 1996 Dohrmann et al., 1996 | | |
| | Ace2 | | Knapp et al., 1996 Dohrmann et al., 1996 | McBride et al., 1999 | Dohrmann et al., 1996 |
| EGT2 | Swi5 | | | Kovacech et al., 1996 McBride et al., 1999 | Kovacech et al., 1996; |
| | Ace2 | | | Kovacech et al., 1996 McBride et al., 1999 | |
| FAR1 | Mcm1 | | | Ohelen et al., 1996 | Kuo et al., 1994 |
| GAS1 | Swi4 | | | Igual et al., 1996 | Igual et al., 1996 |
| GLS1 | Swi4 | | | Igual et al., 1996 | Igual et al., 1996 |
| HO | Swi4 | Cosma et al., 1999 | Ogas et al. 1991 Partridge et al., 1997 | | |
| | Swi6 | | Ogas et al., 1991 | | |
| KRE6 | Swi4 | | | Igual et al., 1996 | Igual et al., 1996 |
| MFA1 | Mcm1 | | | Elble and Tye 1991 | |
| MFA2 | Mcm1 | | | | Kuo et al., 1994 |
| MNN1 | Swi4 | | | Igual et al., 1996 | Igual et al., 1996 |
| OCH1 | Swi4 | | | | Igual et al., 1996 |
| PCL1 | Swi4 | | Ogas et al., 1991 | Ogas et al., 1991 | |
| | Swi6 | | Ogas et al., 1991 | | |
| PCL2 | Swi5 | | Aerne et al., 1998 | Aerne et al., 1998 McBride et al., 1999 | Aerne et al., 1998 |
| | Ace2 | | | McBride et al., 1999 | |
| PCL9 | Swi5 | | Aerne et al., 1998 | Tennyson et al., 1998 Aerne et al., 1998 McBride et al., 1999 | |
| RNR1 | Swi6 | | | Dirick et al., 1992 | |
| | Mbp1 | | | | Lowdens et al., 1991 |
| SIC1 | Swi5 | | Knapp et al., 1996 | Knapp et al., 1996 Toyn et al., 1996 McBride et al., 1999 | |
| STE2 | Mcm1 | Ganter et al., 1993 Koranda et al., 2000 | Primig et al., 1991 | Hwang-Shum et al., 1991 | Kuo et al., 1994 |
| STE6 | Mcm1 | | | | McInerny et al., 1997 |
| SWI4 | Mcm1 | | McInerny et al., 1997 | McInerny et al., 1997 Foster et al., 1993 | McInerny et al., 1997 |
| | Swi6 | | | | |
| SWI5 | Mcm1 | Althoefer et al., 1995 Koranda et al., 2000 Kumar et al., 2000 | Lydall et al., 1991 Kumar et al., 2000 | Althoefer et al., 1995 | Althoefer et al.,1995 |
| | Fkh1 | Koranda et al., 2000 | | Koranda et al., 2000 Zhu et al., 2000 Kumar et al., 2000 | |
| | Fkh2 | Koranda et al., 2000 Zhu et al., 2000 Kumar et al., 2000 | Koranda et al., 2000 Pic et al., 2000 Kumar et al., 2000 | Koranda et al., 2000 Pic et al., 2000 Zhu et al., 2000 Kumar et al., 2000 | Pic et al., 2000 |
| | Ndd1 | Koranda et al., 2000 | | Loy et al., 1999 | |
| YJL051W | Fkh2 | Zhu et al., 2000 | | | |

Swi4 Regulated Genes

| SAT2 | YKL044W | CLB2 |
| --- | --- | --- |
| YBR071W | CWP1 | CWP2 |
| PCL2 | PRY2 | GAS1 |
| HO | UTH1 | HCM1 |
| GIC2 | YLR084C | PSA1 |
| YDR451C | GLS1 | GIN4 |
| UTR2 | YOX1 | RNR1 |
| MSB2 | CLN1 | SWI4 |

-continued

| BUD9 | PDR16 | YER189W |
| --- | --- | --- |
| YGR151C | PCL1 | YER190W |
| RSR1 | YNL300W | CLB6 |
| YGR153W | YOL011W | CDC6 |
| YGR189C | HTA3 | ELO1 |
| YGR221C | YOL114C | LAP4 |
| SCW4 | SRL1 | EXG1 |
| GIC1 | YOR248W | SPT21 |
| SIM1 | YOR315W | SCW10 |

-continued

| | | |
|---|---|---|
| CIS3 | NDD1 | YNL339C |
| SWE1 | HHO1 | |
| YKL008C | SVS1 | |

Mbp1 Regulated Genes

| | | |
|---|---|---|
| ERP3 | CDC21 | YER190W |
| DUN1 | UFE1 | CLB6 |
| RAD51 | OPY2 | CDC6 |
| YHR149C | HCM1 | ELO1 |
| YJR030C | YDR545W | EXG1 |
| RAD27 | RNR1 | SPT2 |
| CDC45 | SWI4 | YNR009W |
| YMR215W | YER189W | YPL283C |

Alpha Factor Synchronization

Time course expression data for the cell cycle after alpha factor synchronization of yeast cells is from Spellman, P. T., et al., *Mol Biol Cell* 9, 3273-97 (1998).

Regulation of Late G1 Genes

Previous molecular and genetic analysis of a small number of genes suggests that SBF (Swi4 and Swi6) and MBF (Mbp1 and Swi6) are important activators of late G1 genes (Koch and Nasmyth, 1994). Our results confirm this model: Swi4 Mbp1 and Swi6 bound predominantly to promoters of late G1 genes (the significance of the bias toward late G1 genes was tested using a hypergeometric distribution and was $p<10^{-18}$, $p<10^{-14}$ and $p<10^{-20}$ respectively).

Swi6 as a Cofactor for Swi4 (SBF) and Mbp1 (MBF)

Based on studies of several genes, Swi6 has been shown to function as a subunit of both SBF and MBF (Dirick et al. *Nature*, 357:508-513 (1992)). The genome-wide location analysis data indicates that Swi6 binds to almost all of the promoter regions bound by Mbp1 and Swi4 (FIG. 2A), indicating that it is a co-factor of these two regulators throughout the genome.

Regulation of Genes Encoding Cyclins and Cyclin Regulators

The targets of SBF and MBF included key cell cycle regulators (Table 5). SBF and MBF were found to bind the promoters of CLN1, CLB6 and PCL1, SBF binds the promoters of CLN2 and PCL2 and MBF binds the promoter of CLB6. The location analysis also shows that SBF participates in the regulation of G2/M cyclin (Clb2) activity at three levels. First, as suggested previously (Iyer et al. *Nature*, 409:533-536 (2001)) it binds and presumably directly regulates CLB2. Second, SBF regulates the transcription of the transcription factor Ndd1, which in turn also regulates CLB2 transcription. Thus, SBF and Ndd1 collaborate to regulate transcription of the CLB2 gene, whose product is necessary to enter mitosis. Third, SBF and MBF regulate SWE1 and GIN4. Swe1 is an inhibitor of Cdc28-Clb2 which delays entry into mitosis in response to bud emergence defects (Sia, R. A., et al., "Cdc28 tyrosine phosphorylation and the morphogenesis checkpoint in budding yeast," *Mol Biol Cell* 7, 1657-66 (1996)), and Gin4 regulates Swe1 (Barral, Y., et al., "Nim1-related kinases coordinate cell cycle progression with the organization of the peripheral cytoskeleton in yeast," *Genes Dev* 13, 176-87 (1999)).

Regulation of Stage-Specific Functions

SBF and MBF participate in the regulation of genes essential for cellular functions specific to late G1. SBF regulates genes involved in the morphological changes associated with cell budding and MBF controls genes involved in DNA replication and repair (Table 5), confirming a previous study (Iyer et al. *Nature*, 409:533-536 (2001)). We also found that SBF is bound to the promoters of several histone genes (HTA1, HTA2, HTA3, HTB1, HTB2 and HHO1), which makes it likely that SBF contributes to the increase in histone gene transcription observed at S phase.

Redundancy of Activators

Neither SWI4 nor MBP1 is essential for cell viability, but a SWI4/MBP1 double mutant is lethal, suggesting that some redundancy exists between Swi4 and Mbp1 (Mendenhall, M. D., and Hodge, A. E., "Regulation of Cdc28 cyclin-dependent protein kinase activity during the cell cycle of the yeast *Saccharomyces cerevisiae*," *Microbiol Mol Biol Rev* 62, 1191-243 (1998)). We found that most of the cell cycle genes involved in budding are bound by SBF alone and that most cell cycle genes involved in DNA replication are bound by MBF alone. In these cases, it does not appear that SBF and MBF play redundant regulatory roles in wild type cells. Iyer et al. *Nature*, 409:533-536 (2001) also reported that Swi4 and Mbp1 bind to different genes involved in distinct cellular functions. However, 34% of all genes bound by SBF or MBF are bound by both factors, indicating that regulation of these genes in a population of wild type cells is normally under the control of both factors and demonstrating that there is substantial redundancy in the regulation of these cell cycle controlled genes in normal cells.

Promoter Binding Motifs

The large number of targets we found enabled us to search for putative DNA binding motifs. To this end we ran AlignACE (Hughes, J. D., et al, *J Mol Biol* 296, 1205-14 (2000)), a program that uses a Gibbs sampling algorithm to find common regulatory elements among a collection of promoters. We found a refined version of the known binding sites of Swi4 and of Mbp1. Although these motifs are highly enriched in the set of target genes identified by our location analysis (p<10–14 and p<10–20 respectively), they also occur in the promoters of many genes that show no evidence of binding to these factors in vivo, suggesting that the presence of this sequence alone is not a predictor of factor binding.

Fkh1 and Fkh2

Fkh1 and Fkh2 are two members of the Forkhead family of proteins that share 82% similarity in amino acid sequence (Kumar et al. *Curr. Biol.*, 10:0896-906 (2000)). Genetic analysis has suggested that these two genes are involved in cell cycle control in pseudohyphal growth, and in silencing of HMRa (Hollenhorst et al. *Genetics*, 154:1533-1548 (2000)). Their contribution to the regulation of cell cycle genes appears to be in G2/M, since it has been shown that Fkh1, together with Mcm1, recruits Ndd1 and thereby regulates the G2/M specific transcription of CLB2, SWI5 and YJL051 W (Zhu et al. *Nature*, 406:90-94 (2000); Koranda et al., *Nature*, 406:94-98 (2000); Kumar et al. *Curr. Biol.*, 10:896-906 (2000); Pic et al. *Embo J*, 19:3750-3761 (2000)). Fkh1 appears to have similar roles in regulating G2/M genes as it is also found bound to the CLB2 promoter (Kumar et al. *Curr. Biol.*, 10:896-906 (2000)).

Regulation of Genes Throughout Cell Cycle

Our results confirm that Fkh1 and Fkh2 are involved in regulating genes expressed in G2/M, but indicate that these proteins also regulate genes expressed in other cell cycle stages. Fkh2 binds predominantly to promoters of genes expressed in G2/M (p<10−9), but it is also enriched in G1 (p<10−4) and S/G2 (p<10−3). Fkh1 target genes are expressed in G1 (p<10−2), S (p<10−3), S/G2 (p<10−5) and G2/M (p<10−4). The association of Fkh1 or Fkh2 with Mcm1 is limited to genes expressed in G2/M; in other stages Fkh1 and Fkh2 bind to promoters in the absence of Mcm1.

Regulation of Genes Encoding Cyclins and Cyclin Regulators

The targets of Fkh1 and Fkh1 include several key cell cycle regulators (Table 5). Fkh1 bound to the promoter of the CLB4 gene, which encodes a S/G2 cyclin (Fitch, I., et al., *Mol Biol Cell* 3, 805-18 (1992)), and Fkh2 bound to the promoter of HSL7, which encodes a regulator of Swe1 that is necessary for the transition into mitosis (Shulewitz, M. J., et al., *Mol Cell Biol* 19, 7123-37 (1999)). Fkh1 and Fkh2 also bind to promoters of genes involved in exit from mitosis; these include APC1, which encodes for a component of the anaphase-promoting complex (Zachariae, W., and Nasmyth, K. *Genes Dev* 13, 2039-58 (1999)), and TEM1, which encodes a protein required for activation of Cdc14p and the mitotic exit pathway (Krishnan, R., et al. *Genetics* 156, 489-500 (2000)).

Regulation of Chromatin

Fkh1 was found to bind various genes that encode proteins associated with chromatin structure and its regulation; these include histones (HHF1 and HHT1), telomere length regulators (TEL2 and CTF18), a component of the chromatin remodeling complexes Swi/Snf and RSC (ARP7), and histone deacetylase (HOS3).

Redundancy of Activators

Genetic analysis has suggested that Fkh1 and Fkh2 have distinct roles in cell cycle progression, but redundant roles in pseudohyphal growth (Hollenhorst et al. *Genetics*, 154:1533-1548 (2000)). We found that Fkh1 and Fkh2 bind to the promoters of 38 and 56 cell cycle genes, respectively, and that 16 of these genes were bound by both proteins. Among the G2/M genes that are targets of Fkh2, three genes (CLB2, ACE2 and BUD4) are also targets of Fkh1.

Promoter Binding Motifs

In order to identify the binding motifs for Fkh1 and Fkh2, we ran AlignACE (Hughes, J. D., et al, *J Mol Biol* 296, 1205-14 (2000)) on the set of promoters bound by each factor. The program identified the known Forkhead binding motif (GTAAACAA (SEQ ID NO: 31)) in the two sets of promoters (p<10−9). However, this sequence was absent from most of the promoters bound by Fkh1 and Fkh2, suggesting that additional sequence elements contribute to the binding sites for these proteins. The promoters of Fkh1 targets, but not Fkh2 targets, are enriched for several additional motifs.

Mcm1 and its Cofactors, Fkh2 and Ndd1

Regulation of G2/M and M/G1 Genes

Previous studies have demonstrated that Mcm1 is involved in the regulation of cell cycle genes that are expressed both in G2/M and in M/G1. Mcm1 collaborates with Ndd1 and Fkh1 or Fkh2 to regulate G2/M genes (Zhu et al. *Nature*, 406:90-94 (2000); Koranda et al., *Nature*, 406:94-98 (2000); Kumar et al. *Curr. Biol.*, 10:896-906 (2000); Pic et al. *Embo J*, 19:3750-3761 (2000)). Mcm1 also regulates M/G1 genes, but less is known about its functions in this stage of the cell cycle (McInerny et al. *Genes Dell.*, 11:1277-1288 (1997)). Our results suggest that differential regulation of Mcm1 target genes in G2/M and M/G1 is governed by Mcm1's association with different regulatory partners. Mcm1 binds predominantly to promoters of genes in G2/M (p<10−14) and in M/G1 (p<10−6). In contrast, Mcm1's cofactors Ndd1 and Fkh2 bind to promoters of G2/M genes (p<10−21 and p<10−15 respectively) but were absent from promoters of M/G1 genes.

Regulation of Entry into and Exit from Mitosis

The location analysis indicates that the G2/M activators (Mcm1/Fkh2/Ndd1) regulate genes necessary for both entry into and exit from mitosis (Table 5). The G2/M activators regulate transcription of CLB2, whose product is necessary to enter mitosis. They also set the stage for exit from mitosis at several levels. First, they regulate the transcription of SWI5 and ACE2, which encode key M/G1 transcriptional activators. Second they bind the promoter of CDC20, an activator of the anaphase promoting complex (APC), which targets the APC to degrade Pds1 and thus initiate chromosome separation (Visintin et al. *Science*, 278:450-463 (1997)). Cdc20-activated APC also participates in the degradation of Clb5 (Shirayama et al. *Nature*, 402:203-207 (1999)), and thus enables Cdc14 to promote the transcription and activation of Sic1 (Shirayama et al. *Nature*, 402:203-207 (1999)) and to initiate degradation of Clb2 (Jaspersen et al., *Mol. Biol. Cell*, 9:2803-2817 (1998); Visintin et al., (1998)). Finally these activators regulate transcription of SPO12, which encodes a protein that also functions to regulate mitotic exit (Grether et al., *Mol. Biol. Cell*, 10.3689-2703 (1999)).

The involvement of Mcm1 in the regulation of genes important for the transition through START has been suggested previously (McInerny et al. *Genes Del.*, 11:1277-1288 (1997); Ohelen, L. J., Mol Cell Biol 16, 2830-7 (1996)), and our data confirm this notion. Mcm1 in the absence of Ndd1 and Fkh2 binds the promoters of SWI4, a late G1 transcription factor, CLN3, a G1 cyclin that is necessary for the activation of G1 transcription machinery (Dirick et al. *Embo. J*, 14:4803-4813 (1995)) and FAR1, which encodes an inhibitor of the G1 cyclins (Valdivieso, M. H., et al. *Mol Cell Biol* 13, 1013-22 (1993)).

Regulation of Stage-Specific Functions

Mcm1, in the absence of Ndd1 and Fkh2, participates in the regulation of genes essential for cellular functions specific to late mitosis and early G1. It binds to and apparently regulates genes encoding proteins involved in pre-replication complex formation (MCM3, MCM6, CDC6 and CDC46) and in mating (STE2, STE6, FAR1, MFA1, MFA2, AGA1 and AGA2).

Promoter Binding Motifs

In order to identify DNA binding motifs for Mcm1, we ran AlignACE (Hughes, J. D., et al, *J Mol Biol* 296, 1205-14 (2000)) on the set of promoters bound by the combination of Mcm1 Fkh2 and Ndd1 and on the promoters bound by Mcm1 alone. We found that all the promoters of the first group contain a motif with a Mcm1 binding site adjacent to a Fkh binding site. This combined motif was highly specific (p<10−34) to these promoters. Almost all the promoters from the second group (89%) contain a Mcm1 binding motif which was also highly specific for these promoters (p<10−27). Interestingly the Mcm1 motif found in these two groups of promoters was slightly different, with several more nucleotides conserved in the motif found in the promoters of the genes bound by Mcm1 alone.

Ace2 and Swi5

Ace2 and Swi5 have been shown to control certain genes expressed in late mitosis and early G1 phases of the cell cycle (McBride et al. *J. Biol. Chem.*, 274:21029-21036 (1999)). Our results confirm that Ace2 and Swi5 bound predominantly to promoters of M/G1 genes (p<10−3 and p<10−14, respectively).

Regulation of Genes Encoding Cyclins and Other Cell Cycle Regulators

The targets of Ace2 and Swi5 included cell cycle regulators (Table 5), Ace2 bound to the promoter of PCL9, whose product is the only cyclin known to act in M/G1 (Aerne, B. L., Mol Biol Cell 9, 945-56 (1998)). Both Ace2 and Swi5 bound to promoters of two of the G1 cyclin genes (PCL2 and CLN3), and Swi5 bound to the gene encoding the cyclin regulator Sic1, which inhibits Clb-CDK activity, allowing exit from mitosis.

Regulation of Stage-Specific Functions

Ace2 and Swi5 were bound to the promoters of several genes whose products are involved in cell wall biogenesis and cytokinesis (Table 5). Swi5 bound to the promoters of 17 Y' genes, which are a subgroup of a larger group of sub-telomeric genes that share DNA sequence similarity and whose expression peaks in early G1 (Spellman, P. T., et al., Mol Biol Cell 9, 3273-97 (1998)).

Redundancy of Activators

Genetic analysis has suggested that ACE2 and SWI5 are redundant; a deletion of either ACE2 or SWI5 does not abolish transcription of most of their target genes (McBride et al. J. Biol. Chem., 274:21029-21036 (1999)). Our results indicate that the functional overlap seen in mutants reflects partial functional redundancy. Ace2 and Swi5 bind to the promoters of 30 and 55 cell cycle genes respectively, and the promoters of 17 of these genes are bound by both factors. This result suggests that the redundancy is limited to a subset of the target genes in wild type cells. Among the targets that are unique to one or the other factor are genes whose transcription is abolished only in the absence of both Ace2 and Swi5, suggesting that in the absence of one factor, the other one can fill its place. However, in wild type cells only one factor is normally bound to these promoters.

Promoter Binding Motifs

In order to identify the binding motifs of Ace2 and Swi5 we ran AlignACE (Hughes, J. D., et al, J Mol Biol 296, 1205-14 (2000)) on the group of promoters bound by each factor. We were able to identify motifs similar to the published binding sites of these factors that were enriched in the set of promoters bound by Ace2 and Swi5 (p<10-6 and p<10-18 respectively). These motifs were found only in about 50% of the promoters, suggesting Ace2 and Swi5 can bind DNA through additional binding sites; several candidates are shown in the figure below.

Redundancy

The location analysis data demonstrate that each of the nine cell cycle transcription factors binds to critical cell cycle genes, yet cells with a single deletion of MBP1, SWI4, SWI6, FKH1, FKH2, ACE2 or SWI5 are viable; only MCM1 and NDD1 are essential for yeast cell survival. The conventional explanation for this observation is that each non-essential gene product shares its function with another, and the location data support this view, up to a point. Swi4 and Mbp1 are identical in 50% of their DNA binding domains (Koch et al. Science, 261.1551-1557 (1993)), Fkh1 and Fkh2 are 72% identical in their DNA binding domains (Kumar et al. Curr. Biol., 10:896-906 (2000)), and Swi5 and Ace2 are 83% identical in their DNA binding domains (McBride et al. J. Biol. Chem. 274:21029-21036 (1999)). Each of these pairs of proteins recognize similar DNA motifs, so it is likely that functional redundancy rescues cells with mutations in individual factors. Until now, however, it was not possible to determine whether each of the pairs of factors had truly redundant functions in normal cells, or whether they can rescue function in mutants that lack the other factor.

Our data demonstrate that each of the cell cycle factor pairs discussed above do bind overlapping sets of genes in wild type cells, revealing that the two members of each of the pairs are partially redundant in normal cell populations. Mbp1 and Swi4 share 34% of their target genes, Fkh1 and Fkh2 share 22%, and Ace2 and Swi5 share 25%. It is also clear, however, that this redundancy doesn't apply in wild type cells to many genes that are normally bound by one member of these pairs. The partial overlap in genes under the control of pairs of regulators explains why one gene of a pair can rescue defects in the other, yet each member of the pair can be responsible for distinct functions in wild type cells.

Why might cells have evolved to have pairs of cell cycle transcriptional regulators with partially redundant functions? This configuration provides cells with two useful parameters particularly relevant to cell cycle function. Pairs of regulators with overlapping function may help ensure that the cell cycle is completed efficiently, even when one activator is not fully functional, which is critical since the inability to complete the cycle leads to death. At the same time, devoting each of the pair to distinct functional groups of genes ensures coordinate regulation of that function.

DNA Binding Motifs

Genome-wide location analysis identifies the set of promoters that are bound by the same transcription factor. The availability of a large number of putative targets is ideal for DNA binding motif searching to identify common DNA regulatory elements. In order to identify the consensus binding sites for cell cycle transcription factors, we used the AlignACE program (Hughes, J. D., et al, J Mol Biol 296, 1205-14 (2000)).

Several general insights evolved from our analysis. First, the DNA binding motif alone is not a sufficient predictor of protein binding, since these motifs are generally found in many sites in the genome other than the promoters that are bound in vivo. Similar observations have been reported by us and others in previous studies (Ren, B., et al., Science 290, 2306-9 (2000); Iyer et al. Nature, 409:533-536 (2001)). This indicates that there is a need for additional empirical data combined and perhaps improved search algorithms in order for investigators to accurately predict genuine binding sites. Second, the binding sites identified here for Mbp1, Swi4 and Mcm1 are found in most but not all of the promoters of their target genes. This suggests that variations of the consensus sequence that are not easily recognized by search algorithms may also serve for binding, or that the factor of interest is modified or associated with binding partners that generate a new binding preference. In this context, it is interesting that the Mcm1 binding motif is somewhat different in the promoters of its G2/M targets than in its M/G1 targets, probably reflecting the influence of its binding partners. Finally, we have identified multiple binding motifs for forkhead factors, Ace2 and Swi5, suggesting that these proteins can recognize different motifs or that motif recognition depends on modifications or partnering with as yet unidentified proteins.

Summary

Using the Genome Wide Location Analysis technique, we identified targets of all known cell cycle transcription activators identified genome-wide.

These results reveal how multiple activators collaborate to regulate temporal expression of genes in the cell cycle.

Each activator group regulates at least one activator for the next phase.

Each activator group regulates genes involved in phase entry and CDK/cyclin regulators that set the stage for exiting that phase.

Specific activators are associated with specific cell cycle functions.

We also identified consensus DNA binding motifs for each of the nine activators profiled.

Finally, partial redundancy between pairs of activators may serve to ensure that the cell cycle is completed efficiently while allowing each activator to regulate distinct functional groups of genes.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method comprising:
   a) crosslinking DNA binding protein of a cell to genomic DNA of the cell, thereby producing crosslinked genomic DNA;
   b) sonicating said crosslinked genomic DNA to produce a population of genomic fragments;
   c) separating DNA fragments to which a protein of interest is bound from said population of genomic fragments; and
   d) amplifying said DNA fragments by:
      i. blunting said DNA fragments to produce blunt ends;
      ii. ligating adaptors to said blunt ends; and
      iii. amplifying said DNA fragments using a primer that binds to said adaptors;
      to produce an amplified population of nucleic acids.

2. The method of claim 1, further comprising analyzing said amplified population of nucleic acids to identify a site to which said protein of interest binds.

3. The method of claim 1, further comprising labeling said amplified population of nucleic acids, either during or after said amplifying step d) to produce labeled DNA fragments.

4. The method of claim 1, further comprising: e) contacting said labeled DNA fragments with a nucleic acid array under conditions in which nucleic acid hybridization occurs.

5. The method of claim 4, further comprising reading said nucleic acid array to determine a binding pattern.

6. The method of claim 3, wherein said amplified population of DNA fragments are labeled during said amplifying.

7. The method of claim 3, wherein said amplified population of DNA fragments are labeled after said amplifying.

8. The method of claim 1, wherein said blunting employs T4 DNA polymerase.

9. The method of claim 1, wherein said genomic DNA is genomic DNA of a mammalian cell.

10. The method of claim 1, wherein said crosslinking step a) comprises crosslinking DNA binding protein of a living cell to genomic DNA of the living cell.

11. The method of claim 1, wherein said crosslinking step a) does not comprise crosslinking DNA binding protein of a living cell to genomic DNA of the living cell.

* * * * *